(12) United States Patent
Lan et al.

(10) Patent No.: US 9,388,133 B2
(45) Date of Patent: Jul. 12, 2016

(54) PYRROLE SULFONAMIDE DERIVATIVE, PREPARATION METHOD FOR SAME, AND MEDICAL APPLICATION THEREOF

(71) Applicant: Jiangsu Hansoh Pharmaceutical Co., Ltd., Lianyungang, Jiangsu (CN)

(72) Inventors: Jiong Lan, Jiangsu (CN); Piaoyang Sun, Jiangsu (CN); Lei Chen, Jiangsu (CN); Wei Peng, Jiangsu (CN); Xing Liu, Jiangsu (CN); Qing Dong, Jiangsu (CN)

(73) Assignee: Jiangsu Hansoh Pharmaceutical Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 14/443,908

(22) PCT Filed: Nov. 6, 2013

(86) PCT No.: PCT/CN2013/086628
§ 371 (c)(1),
(2) Date: May 19, 2015

(87) PCT Pub. No.: WO2014/075575
PCT Pub. Date: May 22, 2014

(65) Prior Publication Data
US 2015/0307449 A1    Oct. 29, 2015

(30) Foreign Application Priority Data

Nov. 19, 2012   (CN) .......................... 2012 1 0468283

(51) Int. Cl.
*C07D 207/48*    (2006.01)

(52) U.S. Cl.
CPC .................................. *C07D 207/48* (2013.01)

(58) Field of Classification Search
None
See application file for complete search history.

(56) References Cited

FOREIGN PATENT DOCUMENTS

| CN | 1036762 A | 11/1989 |
|----|-----------|---------|
| CN | 101300229 A | 11/2008 |
| CN | 101962388 A | 2/2011 |
| WO | 2005041961 A1 | 5/2005 |
| WO | 2006134460 A1 | 12/2006 |
| WO | 2007026916 A1 | 3/2007 |
| WO | 2009041447 A1 | 4/2009 |
| WO | 2010021149 A1 | 2/2010 |

OTHER PUBLICATIONS

Luo et. al., Protonated Form: The Potent Form of Potassium-Competitive Acid Blockers. PLOS ONE, 2014, 9, 1-13.*
Andersson et al., Potassium-competitive acid blockage: a new therapeutic strategy in acid-related diseases. Pharmacology & Therapeutics. 2005, 108, 294-307.*
Shafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Cerfontain et al, "Sulfonation of Three Symmetrical 2,6-Dialkylphenols, 2,6-Dichlorophenol, Phenol, and 2,6-Dimethylanisole. Sulfation and Sulfonation Product Distributions and Mechanisms," J. Org. Chem., vol. 49, pp. 4917-4923 (1984).
Arikawa et al, "Discovery of a Novel Pyrrole Derivative 1-[5-(2-Fluorophenyl)-1-(pyridin-3-ylsulfonyl)-1H-pyrrol-3-yl]-N-methylmethanamine Fumarate (TAK-438) as a Potassium-Competitive Acid Blocker (P-CAB)," Journal of Medicinal Chemistry, vol. 55, pp. 4446-4456 (2012).
Vloon et al, "Synthesis and Biological Properties of Side-Chain-Modified Bleomycins," J. Med. Chem., vol. 30, pp. 20-24 (1987).
Krief et al, "Novel Synthesis of gamma-Selenobutyrates from Geminally Diactivated Cyclopropane Derivatives," Tetrahedron Letters, vol. 28, No. 36, pp. 4225-4228 (1987).

(Continued)

*Primary Examiner* — Rebecca Anderson
*Assistant Examiner* — Po-Chih Chen
(74) *Attorney, Agent, or Firm* — Panitch Schwarze Belisario & Nadel LLP

(57) ABSTRACT

The present invention relates to a pyrrole sulfonamide derivative, a preparation method for the same, and medical applications thereof. Specifically, the present invention relates to a novel pyrrole sulfonamide derivative as represented by formula (I), a preparation method for the derivative, a pharmaceutical composition comprising the derivative, and uses of the same as therapeutic agents, and particularly as gastric acid secretion inhibitors and potassium-competitive acid blockers (P-CABs), wherein each substituent of formula (I) is as defined in the description.

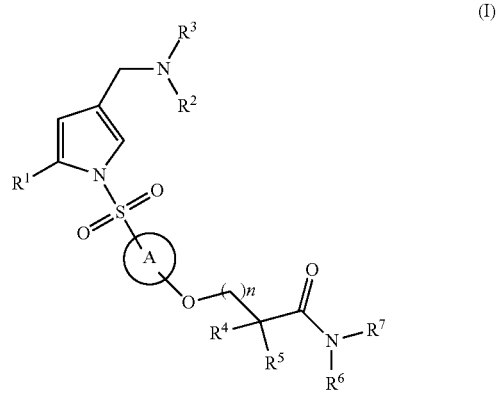

(I)

21 Claims, No Drawings

(56) References Cited

OTHER PUBLICATIONS

Takagi et al, "Palladium-Catalyzed Cross-Coupling Reaction of Bis(pinacolato)diboron with 1-Alkenyl Halides or Triflates: Convenient Synthesis of Unsymmetrical 1,3-Dienes via the Borylation-Coupling Sequence," Journal of the American Chemical Society, vol. 124, No. 27, pp. 8001-8006 (2002).

Int'l Search Report issued Feb. 20, 2014 in Int'l Application No. PCT/CN2013/086628.

* cited by examiner

PYRROLE SULFONAMIDE DERIVATIVE, PREPARATION METHOD FOR SAME, AND MEDICAL APPLICATION THEREOF

CROSS-REFERENCE TO RELATED APPLICATIONS

This application is a Section 371 of International Application No. PCT/CN2013/086628, filed on Nov. 6, 2013, which was published in the Chinese language on May 22, 2014, under International Publication No. WO 2014/075575 A1, and the disclosure of which is incorporated herein by reference.

FIELD OF THE INVENTION

The present invention relates to novel pyrrole sulfonamide derivatives, a preparation method thereof, a pharmaceutical composition comprising the same and use of the derivatives as therapeutic agents, particularly as gastric acid secretion inhibitors and potassium-competitive acid blockers (P-CABs).

BACKGROUND OF THE INVENTION

Peptic ulcer is a common disease, with the disease incidence in different areas at different stages being different, and it is about 10-20% of the number of total population generally. With social development and the change of lifestyle of people, the disease incidence of peptic ulcer caused by smoking, drinking, emotional stress, pharmaceutical stimulation and the like is gradually increased, which is seriously affecting work and life of the people. The exact pathogenesis is still not clear in the field of medicine at present, but inhibition of gastric acid secretion has been recognized as a preferred method for treating such diseases.

Since the first proton pump inhibitor (PPI) came into the market in 1988, there have been a number of PPI products coming into the market up to now. After years of clinical application, PPIs have been the preferred medicaments for treating gastric acid-related diseases. A proton pump, also called a gastric acid pump, is H adenosine triphosphatase ($H^+/K^+$-ATPase) essentially, is a final common pathway of gastric secretion of H exists on cell membranes of secretory tubules of gastric parietal cells and can perform $H^+$ and $K^+$ exchange by means of ATP degradation and specifically pump $H^+$ into gastral cavity to form a strong acidic state in the stomach. The proton pump is a heterodimer and consists of transmembrane a and subunits. The a subunit has 10 helical transmembrane segments (M1-M10), is mainly responsible for catalytic activity of an enzyme and supply of ATP binding sites which are also binding sites for cations, and is also called a catalytic subunit; and the functional expression of the enzyme needs the participation of the single-pass transmembrane subunit. PPIs are weak alkaline and lipophilic compounds, can rapidly pass through the cell membranes of the gastric wall, are accumulated in the strong acidic secretory tubules, are converted to sulfonamide compounds under the catalytic action of $H^+$, and are covalently bound to sulfhydryl on cysteine residues of an $H^+/K^+$-ATPase transmembrane region to form disulfide bonds, thereby inactivating the proton pumps and further inhibiting central or peripheral mediated gastric acid secretion.

The first generation of PPIs has an obvious effect of inhibiting gastric acid secretion stimulated by basic and nocturnal gastric acid, pentagastrin, test meal and the like. However, due to the limitations of pharmacokinetics and pharmacodynamics, including the effects of bioavailability and drug administration time on drug effects, slow onset of action of nocturnal acid breakthrough, instability in acidic conditions (the PPIs often need to be prepared into bowel preparations, and in such situations, the effects can only be seen after several hours), dependence on a CYP450 enzyme (the plasma concentrations of the PPIs of different patients are greatly different, which may cause great differences in acid inhibition effects of the different patients) and other factors, the treatment effects and the clinical application are affected. Compared with the first generation of PPIs, the new generation of PPIs has obvious advantages in treatment of gastroesophageal reflux disease (GERD) and other acid-related diseases.

As a novel type of acid inhibitors, potassium-competitive acid blockers (P-CABs) can inhibit the activity of the $H^+/K^+$-ATPase by competitively binding of $H^+$, and the mechanism of action is obviously different from that of PPIs, so that the P-CABs may be called acid pump blockers. The P-CABs have the characteristics of lipophilicity, weak alkalinity, high dissociation constant and stability at low pH value. In an acidic environment, the P-CABs are immediately ionized, the ionized form is to inhibit the $H^+/K^+$-ATPase by ionic binding and prevent $H^+$ transportation and acid secretion into the gastral cavity, the activation of microcapsules, microtubules and the acid concentrated on gastric parietal cells is not required, the pH value in the stomach can be rapidly increased, and the enzymatic activity after dissociation is recovered. Rapid absorption can be realized after oral administration to human and animals, and the peak plasma concentrations can be achieved. Clinical and animal experiments also show that, compared with the PPIs or the H2 receptor blockers, the P-CABs are faster in onset of action and stronger in the action of increasing the pH, wherein part of the P-CABs preparations have entered phase II and phase III clinical researches. The P-CABs have the following potential advantages: rapid onset of action, wherein the maximum effect can be achieved within 1 h; and linear correlation between plasma concentration and oral administration dosage, suggesting that such medicaments can achieve the best acid inhibition state relatively easily.

At present, a series of patent applications of potassium-competitive acid blockers (P-CABs) are disclosed, wherein the patent applications comprise WO2005041961, WO2006134460, WO2009041447 or WO2010021149 and the like.

Although a series of potassium-competitive acid blockers (P-CABs) have been disclosed at present, novel compounds with better drug effects still need to be developed, and after continuous efforts, in the present invention, compounds represented by formula (I) are designed and it is found that a compound with such a structure exhibits excellent effect and function.

SUMMARY OF THE INVENTION

The object of the present invention is to provide a compound of formula (I), or a tautomer, mesomer, racemate, enantiomer, diastereoisomer or mixture thereof, or a pharmaceutically acceptable salt thereof:

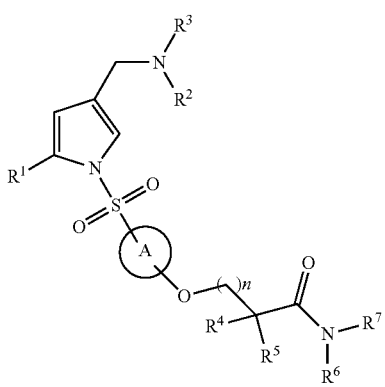

(I)

wherein:

R¹ is selected from the group consisting of cycloalkyl, heterocyclyl, aryl and heteroaryl, wherein the cycloalkyl, heterocyclyl, aryl and heteroaryl are each optionally substituted by one or more groups selected from the group consisting of halogen, cyano, alkyl, haloalkyl, hydroxyalkyl, cycloalkyl, alkoxy, heterocyclyl, aryl, heteroaryl, carboxyl and alkoxycarbonyl;

R² is selected from the group consisting of hydrogen atom, alkyl, cycloalkyl, heterocyclyl, aryl and heteroaryl, wherein the alkyl, cycloalkyl, heterocyclyl, aryl and the heteroaryl are each optionally substituted by one or more groups selected from the group consisting of halogen, cyano, hydroxy, amino, alkyl, haloalkyl, hydroxyalkyl, alkoxy, cycloalkyl, heterocyclyl, aryl, heteroaryl, carboxyl and alkoxycarbonyl;

R3 is selected from the group consisting of hydrogen atom and alkyl;

ring A is selected from the group consisting of aryl and heteroaryl, wherein the aryl and heteroaryl are each optionally substituted by one or more groups selected from the group consisting of halogen, cyano, alkyl, haloalkyl, hydroxyalkyl, cycloalkyl, alkoxy, heterocyclyl, aryl, heteroaryl, carboxyl and alkoxycarbonyl;

R4 and R5 are each independently selected from the group consisting of hydrogen atom, halogen, cyano, hydroxy, alkyl, haloalkyl, alkoxy, haloalkoxy, cycloalkyl, heterocyclyl, aryl and heteroaryl;

or R4 and R5 are taken together to form a cycloalkyl or heterocyclyl;

R6 and R7 are each independently selected from the group consisting of hydrogen atom, alkyl, cycloalkyl, heterocyclyl, aryl and heteroaryl, wherein the alkyl, cycloalkyl, heterocyclyl, aryl and heteroaryl are each independently and optionally substituted by one or more groups selected from the group consisting of halogen, cyano, hydroxy, amino, oxo, alkyl, haloalkyl, hydroxyalkyl, alkoxy, cycloalkyl, heterocyclyl, aryl, heteroaryl, carboxyl and alkoxycarbonyl; and n is 0, 1 or 2.

Preferably, R1 is selected from the group consisting of C3-C20 cycloalkyl, heterocyclyl containing 3 to 20 ring atoms, 6 to 14-membered aryl and 5 to 14-membered heteroaryl, wherein the cycloalkyl, heterocyclyl, aryl and heteroaryl are each optionally substituted by one or more groups selected from the group consisting of halogen, cyano, C1-C20 alkyl, C1-C20 haloalkyl, C1-C20 hydroxyalkyl, C3-C20 cycloalkyl, C1-C20 alkoxy, heterocyclyl containing 3 to 20 ring atoms, 6 to 14-membered aryl, 5 to 14-membered heteroaryl, carboxyl and alkoxycarbonyl;

R2 is selected from the group consisting of hydrogen atom, C1-C20 alkyl, C3-C20 cycloalkyl, heterocyclyl containing 3 to 20 ring atoms, 6 to 14-membered aryl and 5 to 14-membered heteroaryl, wherein the alkyl, cycloalkyl, heterocyclyl, aryl and heteroaryl are each optionally substituted by one or more groups selected from the group consisting of halogen, cyano, hydroxy, amino, C1-C20 alkyl, C1-C20 haloalkyl, C1-C20 hydroxyalkyl, C1-C20 alkoxy, C3-C20 cycloalkyl, heterocyclyl containing 3 to 20 ring atoms, 6 to 14-membered aryl, 5 to 14-membered heteroaryl, carboxyl and alkoxycarbonyl;

R3 is selected from the group consisting of hydrogen atom and C1-C20 alkyl;

ring A is selected from the group consisting of 6 to 14-membered aryl and 5 to 14-membered heteroaryl, wherein the aryl and heteroaryl are each optionally substituted by one or more groups selected from the group consisting of halogen, cyano, C1-C20 alkyl, C1-C20 haloalkyl, C1-C20 hydroxyalkyl, C3-C20 cycloalkyl, C1-C20 alkoxy, heterocyclyl containing 3 to 20 ring atoms, 6 to 14-membered aryl, 5 to 14-membered heteroaryl, carboxyl and alkoxycarbonyl;

R4 and R5 are each independently selected from the group consisting of hydrogen atom, halogen, cyano, hydroxy, C1-C20 alkyl, C1-C20 haloalkyl, C1-C20 alkoxy, C1-C20 haloalkoxy, C3-C20 cycloalkyl, heterocyclyl containing 3 to 20 ring atoms, 6 to 14-membered aryl and 5 to 14-membered heteroaryl;

or R4 and R5 are taken together to form a C3-C20 cycloalkyl or heterocyclyl containing 3 to 20 ring atoms;

R6 and R7 are each independently selected from the group consisting of hydrogen atom, C1-C20 alkyl, C3-C20 cycloalkyl, heterocyclyl containing 3 to 20 ring atoms, 6 to 14-membered aryl and 5 to 14-membered heteroaryl, wherein the alkyl, cycloalkyl, heterocyclyl, aryl and heteroaryl are each independently and optionally substituted by one or more groups selected from the group consisting of halogen, cyano, hydroxy, amino, oxo, C1-C20 alkyl, C1-C20 haloalkyl, C1-C20 hydroxyalkyl, C1-C20 alkoxy, C3-C20 cycloalkyl, heterocyclyl containing 3 to 20 ring atoms, 6 to 14-membered aryl, 5 to 14-membered heteroaryl, carboxyl and alkoxycarbonyl; and n is 0, 1 or 2.

More preferably, R1 is selected from the group consisting of C3-C6 cycloalkyl, heterocyclyl containing 5 to 6 ring atoms, 6 to 10-membered aryl and 5 to 6-membered heteroaryl, wherein the cycloalkyl, heterocyclyl, aryl and heteroaryl are each optionally substituted by one or more groups selected from the group consisting of halogen, cyano, C1-C6 alkyl, C1-C6 haloalkyl, C1-C6 hydroxyalkyl, C3-C6 cycloalkyl, C1-C6 alkoxy, heterocyclyl containing 5 to 6 ring atoms, 6 to 10-membered aryl, 5 to 6-membered heteroaryl, carboxyl and alkoxycarbonyl;

R2 is selected from the group consisting of hydrogen atom, C1-C6 alkyl, C3-C6 cycloalkyl, heterocyclyl containing 5 to 6 ring atoms, 6 to 10-membered aryl and 5 to 6-membered heteroaryl, wherein the alkyl, cycloalkyl, heterocyclyl, aryl and heteroaryl are each optionally substituted by one or more groups selected from the group consisting of halogen, cyano, hydroxy, amino, C1-C6 alkyl, C1-C6 haloalkyl, C1-C6 hydroxyalkyl, C1-C6 alkoxy, C3-C6 cycloalkyl, heterocyclyl containing 5 to 6 ring atoms, 6 to 10-membered aryl, 5 to 6-membered heteroaryl, carboxyl and alkoxycarbonyl;

R3 is selected from the group consisting of hydrogen atom and C1-C20 alkyl;

ring A is selected from the group consisting of 6 to 10-membered aryl and 5 to 6-membered heteroaryl, wherein the aryl and heteroaryl are each optionally substituted by one or more groups selected from the group consisting of halogen, cyano, C1-C6 alkyl, C1-C6 haloalkyl, C1-C6 hydroxyalkyl, C3-C6 cycloalkyl, C1-C6 alkoxy, heterocyclyl containing 5 to 6 ring atoms, 6 to 10-membered aryl, 5 to 6-membered heteroaryl, carboxyl and alkoxycarbonyl;

R4 and R5 are each independently selected from the group consisting of hydrogen atom, halogen, cyano, hydroxy, C1-C20 alkyl, C1-C6 haloalkyl, C1-C6 alkoxy, C1-C6 haloalkoxy, C3-C6 cycloalkyl, heterocyclyl containing 5 to 6 ring atoms, 6 to 10-membered aryl and 5 to 6-membered heteroaryl; or R4 and R5 are taken together to form a C3-C6 cycloalkyl or heterocyclyl containing 5 to 6 ring atoms;

R6 and R7 are each independently selected from the group consisting of hydrogen atom, C1-C6 alkyl, C3-C6 cycloalkyl, heterocyclyl containing 5 to 6 ring atoms, 6 to 10-membered aryl and 5 to 6-membered heteroaryl, wherein the alkyl, cycloalkyl, heterocyclyl, aryl and heteroaryl are each independently and optionally substituted by one or more groups selected from the group consisting of halogen, cyano, hydroxy, amino, oxo, C1-C6 alkyl, C1-C6 haloalkyl, C1-C6 hydroxyalkyl, C1-C6 alkoxy, C3-C6 cycloalkyl, heterocyclyl containing 5 to 6 ring atoms, 6 to 10-membered aryl, 5 to 6-membered heteroaryl, carboxyl and alkoxycarbonyl; and n is 0, 1 or 2.

In an embodiment of the present invention, a compound of formula (I), or a tautomer, mesomer, racemate, enantiomer, diastereomer, or mixture thereof, or a pharmaceutically acceptable salt thereof is selected from a compound of formula (II), or a tautomer, mesomer, racemate, enantiomer, diastereomer, or mixture thereof, or a pharmaceutically acceptable salt thereof:

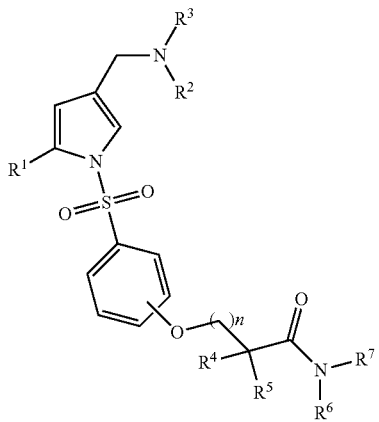

(II)

wherein:

R1 is selected from the group consisting of cycloalkyl, heterocyclyl, aryl and heteroaryl, wherein the cycloalkyl, heterocyclyl, aryl and heteroaryl are each optionally substituted by one or more groups selected from the group consisting of halogen, cyano, alkyl, haloalkyl, hydroxyalkyl, cycloalkyl, alkoxy, heterocyclyl, aryl, heteroaryl, carboxyl and alkoxycarbonyl;

R2 is alkyl;

R3 is selected from the group consisting of hydrogen atom and alkyl;

R4 and R5 are each independently selected from the group consisting of hydrogen atom, halogen, cyano, hydroxy, alkyl, haloalkyl, alkoxy, haloalkoxy, cycloalkyl, heterocyclyl, aryl and heteroaryl;

or R4 and R5 are taken together to form a cycloalkyl or heterocyclyl;

R6 and R7 are each independently selected from the group consisting of hydrogen atom, alkyl, cycloalkyl, heterocyclyl, aryl and heteroaryl, wherein the alkyl, cycloalkyl, heterocyclyl, aryl and heteroaryl are each independently and optionally substituted by one or more groups selected from the group consisting of halogen, cyano, hydroxy, amino, oxo, alkyl, haloalkyl, hydroxyalkyl, alkoxy, cycloalkyl, heterocyclyl, aryl, heteroaryl, carboxyl and alkoxycarbonyl; and n is 0, 1 or 2.

Preferably, R1 is selected from the group consisting of C3-C20 cycloalkyl, heterocyclyl containing 3 to 20 ring atoms, 6 to 14-membered aryl and 5 to 14-membered heteroaryl, wherein the cycloalkyl, heterocyclyl, aryl and heteroaryl are each optionally substituted by one or more groups selected from the group consisting of halogen, cyano, C1-C20 alkyl, C1-C20 haloalkyl, C1-C20 hydroxyalkyl, C3-C20 cycloalkyl, C1-C20 alkoxy, heterocyclyl containing 3 to 20 ring atoms, 6 to 14-membered aryl, 5 to 14-membered heteroaryl, carboxyl and alkoxycarbonyl;

R2 is C1-C20 alkyl;

R3 is selected from the group consisting of hydrogen atom and C1-C20 alkyl;

R4 and R5 are each independently selected from the group consisting of hydrogen atom, halogen, cyano, hydroxy, C1-C20 alkyl, C1-C20 haloalkyl, C1-C20 alkoxy, C1-C20 haloalkoxy, C3-C20 cycloalkyl, heterocyclyl containing 3 to 20 ring atoms, 6 to 14-membered aryl and 5 to 14-membered heteroaryl;

or R4 and R5 are taken together to form a C3-C20 cycloalkyl or heterocyclyl containing 3 to 20 ring atoms;

R6 and R7 are each independently selected from the group consisting of hydrogen atom, C1-C20 alkyl, C3-C20 cycloalkyl, heterocyclyl containing 3 to 20 ring atoms, 6 to 14-membered aryl and 5 to 14-membered heteroaryl, wherein the alkyl, cycloalkyl, heterocyclyl, aryl and heteroaryl are each independently and optionally substituted by one or more groups selected from the group consisting of halogen, cyano, hydroxy, amino, oxo, C1-C20 alkyl, C1-C20 haloalkyl, C1-C20 hydroxyalkyl, C1-C20 alkoxy, C3-C20 cycloalkyl, heterocyclyl containing 3 to 20 ring atoms, 6 to 14-membered aryl, 5 to 14-membered heteroaryl, carboxyl and alkoxycarbonyl; and n is 0, 1 or 2.

More preferably, R1 is selected from the group consisting of C3-C6 cycloalkyl, heterocyclyl containing 5 to 6 ring atoms, 6 to 10-membered aryl and 5 to 6-membered heteroaryl, wherein the cycloalkyl, heterocyclyl, aryl and heteroaryl are each optionally substituted by one or more groups selected from the group consisting of halogen, cyano, C1-C6 alkyl, C1-C6 haloalkyl, C1-C6 hydroxyalkyl, C3-C6 cycloalkyl, C1-C6 alkoxy, heterocyclyl containing 5 to 6 ring atoms, 6 to 10-membered aryl, 5 to 6-membered heteroaryl, carboxyl and alkoxycarbonyl;

R2 is C1-C6 alkyl;

R3 is selected from the group consisting of hydrogen atom and C1-C6 alkyl;

R4 and R5 are each independently selected from the group consisting of hydrogen atom, halogen, cyano, hydroxy, C1-C6 alkyl, C1-C6 haloalkyl, C1-C6 alkoxy, C1-C6 haloalkoxy, C3-C6 cycloalkyl, heterocyclyl containing 5 to 6 ring atoms, 6 to 10-membered aryl and 5 to 6-membered heteroaryl;

or R4 and R5 are taken together to form a C3-C6 cycloalkyl or heterocyclyl containing 5 to 6 ring atoms;

R6 and R7 are each independently selected from the group consisting of hydrogen atom, C1-C6 alkyl, C3-C6 cycloalkyl, heterocyclyl containing 5 to 6 ring atoms, 6 to 10-membered aryl and 5 to 6-membered heteroaryl, wherein the alkyl, cycloalkyl, heterocyclyl, aryl and heteroaryl are each independently and optionally substituted by one or more groups selected from the group consisting of halogen, cyano, hydroxy, amino, oxo, C1-C6 alkyl, C1-C6 haloalkyl, C1-C6 hydroxyalkyl, C1-C6 alkoxy, C3-C6 cycloalkyl, heterocyclyl containing 5 to 6 ring atoms, 6 to 10-membered aryl, 5 to 6-membered heteroaryl, carboxyl and alkoxycarbonyl; and n is 0, 1 or 2.

In another embodiment of the present invention, in the compound of formula (I), or a tautomer, mesomer, racemate, enantiomer, diastereomer, or mixture thereof, or a pharmaceutically acceptable salt thereof, R1 is 6 to 14-membered aryl or C3-C20 cycloalkyl, wherein the aryl is optionally substituted by one or more halogens.

In another embodiment of the present invention, in the compound of formula (I), or a tautomer, mesomer, racemate, enantiomer, diastereomer, or mixture thereof, or a pharmaceutically acceptable salt thereof, R1 is phenyl or cyclohexenyl, wherein the phenyl is optionally substituted by one or more halogens.

In another embodiment of the present invention, in the compound of formula (I), or a tautomer, mesomer, racemate, enantiomer, diastereomer, or mixture thereof, or a pharmaceutically acceptable salt thereof, R4 is hydrogen atom.

In another embodiment of the present invention, in the compound of formula (I), or a tautomer, mesomer, racemate, enantiomer, diastereomer, or mixture thereof, or a pharmaceutically acceptable salt thereof, R5 is hydrogen atom.

In another embodiment of the present invention, in the compound of formula (I), or a tautomer, mesomer, racemate, enantiomer, diastereomer, or mixture thereof, or a pharmaceutically acceptable salt thereof, R4 and R5 are taken together to form a C3-C20 cycloalkyl, preferably cyclopropyl.

In another embodiment of the present invention, in the compound of formula (I), or a tautomer, mesomer, racemate, enantiomer, diastereomer, or mixture thereof, or a pharmaceutically acceptable salt thereof, R6 and R7 are each independently selected from the group consisting of hydrogen atom, C1-C20 alkyl and C3-C20 cycloalkyl, wherein the alkyl and cycloalkyl are each independently and optionally substituted by one or more groups selected from the group consisting of halogen, hydroxy, amino, C1-C20 alkoxy, C3-C20 cycloalkyl, heterocyclyl containing 3 to 20 ring atoms, 6 to 14-membered aryl, 5 to 14-membered heteroaryl, carboxyl and alkoxycarbonyl.

The typical compounds of the present invention include, but are not limited to:

| Example No. | Structure and name of compound |
|---|---|
| 1 | 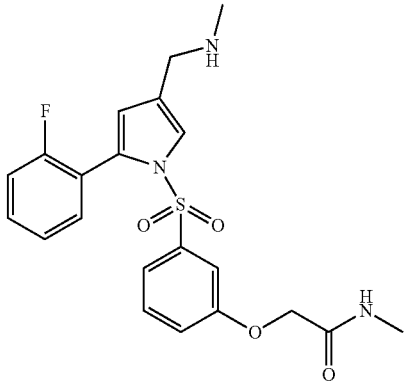 [SMILES: CNCc1cc(-c2ccccc2F)n(S(=O)(=O)c2cccc(OCC(=O)NC)c2)c1]<br>2-(3-((2-(2-fluorophenyl)-4-((methylamino)methyl)-1H-pyrrol-1-yl)sulfonyl)phenoxy)-N-methylacetamide |
| 2 | 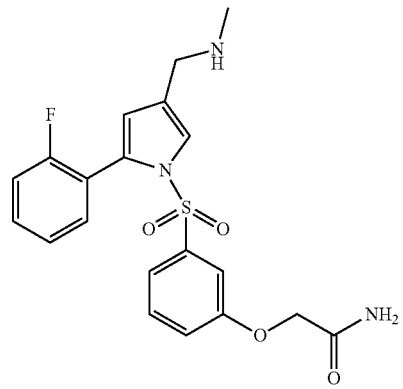 [SMILES: CNCc1cc(-c2ccccc2F)n(S(=O)(=O)c2cccc(OCC(N)=O)c2)c1]<br>2-(3-((2-(2-fluorophenyl)-4-((methylamino)methyl)-1H-pyrrol-1-yl)sulfonyl)phenoxy)acetamide |
| 3 | 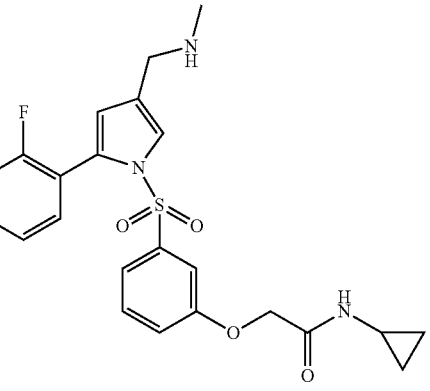<br>N-cyclopropyl-2-(3-((2-(2-fluorophenyl)-4-((methylamino)methyl)-1H-pyrrol-1-yl)sulfonyl)phenoxy)acetamide |

| Example No. | Structure and name of compound |
|---|---|
| 4 | 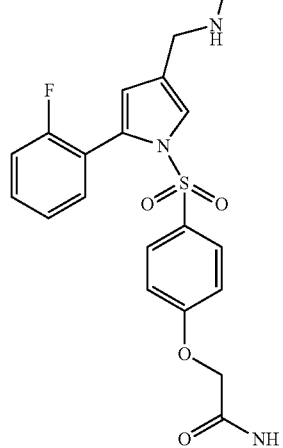<br>2-(4-((2-(2-fluorophenyl)-4-((methylamino)methyl)-1H-pyrrol-1-yl)sulfonyl)phenoxy)-N-methylacetamide |
| 5 | 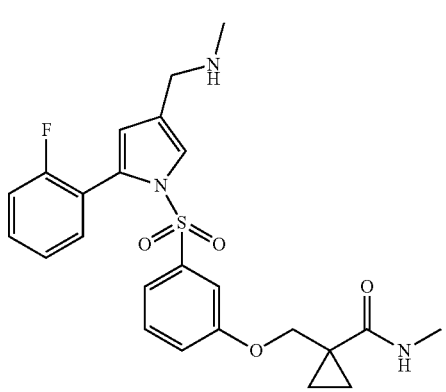 [SMILES: CNCc1cc(-c2ccccc2F)n(S(=O)(=O)c2cccc(OCC3(C(=O)NC)CC3)c2)c1]<br>1-((3-((2-(2-fluorophenyl)-4-((methylamino)methyl)-1H-pyrrol-1-yl)sulfonyl)phenoxy)methyl)-N-methylcyclopropylcarboxamide |
| 6 | 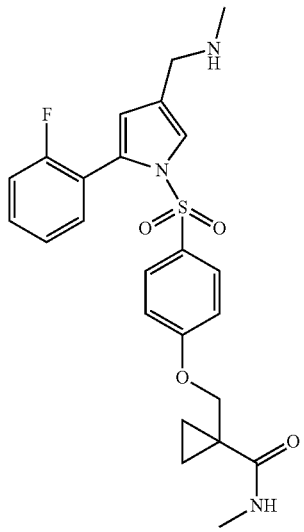 [SMILES: CNCc1cc(-c2ccccc2F)n(S(=O)(=O)c2ccc(OCC3(C(=O)NC)CC3)cc2)c1]<br>1-((4-((2-(2-fluorophenyl)-4-((methylamino)methyl)-1H-pyrrol-1-yl)sulfonyl)phenoxy)methyl)-N-methylcyclopropylcarboxamide |

| Example No. | Structure and name of compound |
|---|---|
| 7 | 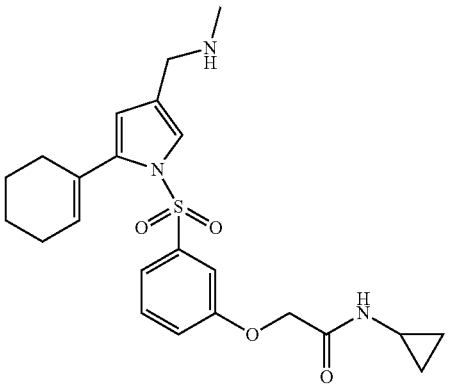 [SMILES: CNCc1cc(C2=CCCCC2)n(S(=O)(=O)c2cccc(OCC(=O)NC3CC3)c2)c1]<br>2-(3-((2-(cyclohex-1-en-1-yl)-4-((methylamino)methyl)-1H-pyrrol-1-yl)sulfonyl)phenoxy)-N-cyclopropylacetamide |
| 8 | 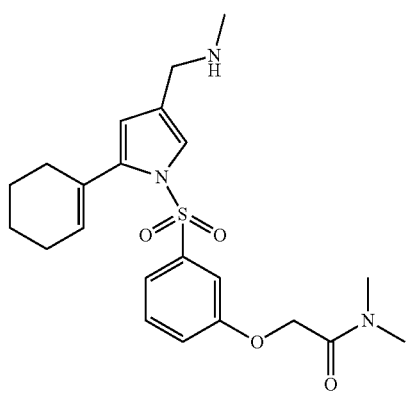 [SMILES: CNCc1cc(C2=CCCCC2)n(S(=O)(=O)c2cccc(OCC(=O)N(C)C)c2)c1]<br>2-(3-((2-(cyclohex-1-en-1-yl)-4-((methylamino)methyl)-1H-pyrrol-1-yl)sulfonyl)phenoxy)-N,N-dimethylacetamide |
| 9 | 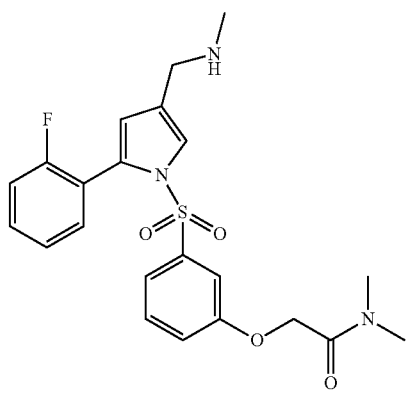 [SMILES: CNCc1cc(-c2ccccc2F)n(S(=O)(=O)c2cccc(OCC(=O)N(C)C)c2)c1]<br>2-(3-((2-(2-fluorophenyl)-4-((methylamino)methyl)-1H-pyrrol-1-yl)sulfonyl)phenoxy)-N,N-dimethylacetamide |

-continued

| Example No. | Structure and name of compound |
|---|---|
| 10 | 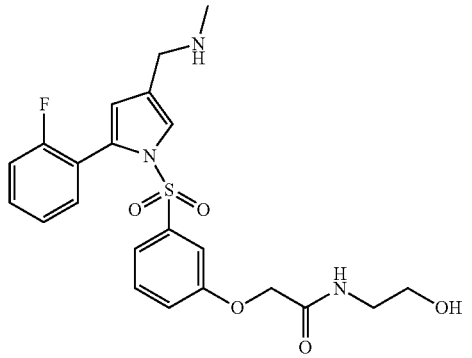 [SMILES: CNCc1cc(-c2ccccc2F)n(S(=O)(=O)c2cccc(OCC(=O)NCCO)c2)c1]<br>2-(3-((2-(2-fluorophenyl)-4-((methylamino)methyl)-1H-pyrrol-1-yl)sulfonyl)phenoxy)-N-(2-hydroxyethyl)acetamide |
| 11 | 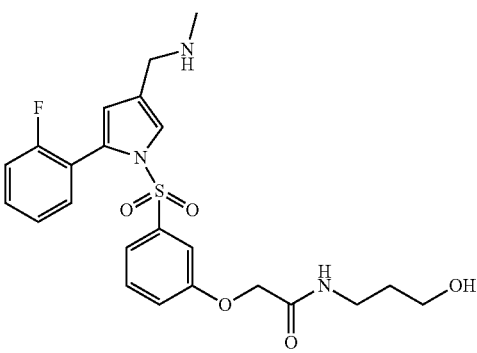 [SMILES: CNCc1cc(-c2ccccc2F)n(S(=O)(=O)c2cccc(OCC(=O)NCCCO)c2)c1]<br>2-(3-((2-(2-fluorophenyl)-4-((methylamino)methyl)-1H-pyrrol-1-yl)sulfonyl)phenoxy)-N-(3-hydroxyphenyl)acetamide | or a tautomer, mesomer, racemate, enantiomer, diastereomer, or mixture thereof, or a pharmaceutically acceptable salt thereof.

The present invention relates to a compound of formula (I-A), or a tautomer, mesomer, racemate, enantiomer, diastereomer, or mixture thereof, or a pharmaceutically acceptable salt thereof:

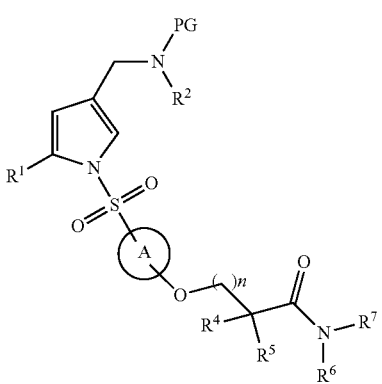

wherein:

R1 is selected from the group consisting of cycloalkyl, heterocyclyl, aryl and heteroaryl, wherein the cycloalkyl, heterocyclyl, aryl and heteroaryl are each optionally substituted by one or more groups selected from the group consisting of halogen, cyano, alkyl, haloalkyl, hydroxyalkyl, cycloalkyl, alkoxy, heterocyclyl, aryl, heteroaryl, carboxyl and alkoxycarbonyl;

R2 is selected from the group consisting of hydrogen atom, alkyl, cycloalkyl, heterocyclyl, aryl and heteroaryl, wherein the alkyl, cycloalkyl, heterocyclyl, aryl and heteroaryl are each optionally substituted by one or more groups selected from the group consisting of halogen, cyano, hydroxy, amino, alkyl, haloalkyl, hydroxyalkyl, alkoxy, cycloalkyl, heterocyclyl, aryl, heteroaryl, carboxyl and alkoxycarbonyl; preferably, R2 is alkyl;

ring A is selected from the group consisting of aryl and heteroaryl, wherein the aryl and heteroaryl are each optionally substituted by one or more groups selected from the group consisting of halogen, cyano, alkyl, haloalkyl, hydroxyalkyl, cycloalkyl, alkoxy, heterocyclyl, aryl, heteroaryl, carboxyl and alkoxycarbonyl; the ring A is preferably aryl, and more preferably phenyl;

R4 and R5 are each independently selected from the group consisting of hydrogen atom, halogen, cyano, hydroxy, alkyl, haloalkyl, alkoxy, haloalkoxy, cycloalkyl, heterocyclyl, aryl and heteroaryl;

or R4 and R5 are taken together to form a cycloalkyl or heterocyclyl; R6 and R7 are each independently selected from the group consisting of hydrogen atom, alkyl, cycloalkyl, heterocyclyl, aryl and heteroaryl, wherein the alkyl, cycloalkyl, heterocyclyl, aryl and heteroaryl are each independently and optionally substituted by one or more groups selected from the group consisting of halogen, cyano, hydroxy, amino, oxo, alkyl, haloalkyl, hydroxyalkyl, alkoxy, cycloalkyl, heterocyclyl, aryl, heteroaryl, carboxyl and alkoxycarbonyl; and n is 0, 1 or 2; and PG is an amino-protecting group, preferably tert-butoxycarbonyl.

Preferably, R1 is selected from the group consisting of C3-C20 cycloalkyl, heterocyclyl containing 3 to 20 ring atoms, 6 to 14-membered aryl and 5 to 14-membered heteroaryl, wherein the cycloalkyl, heterocyclyl, aryl and heteroaryl are each optionally substituted by one or more groups selected from the group consisting of halogen, cyano, C1-C20 alkyl, C1-C20 haloalkyl, C1-C20 hydroxyalkyl, C3-C20 cycloalkyl, C1-C20 alkoxy, heterocyclyl containing 3 to 20 ring atoms, 6 to 14-membered aryl, 5 to 14-membered heteroaryl, carboxyl and alkoxycarbonyl;

R2 is selected from the group consisting of hydrogen atom, C1-C20 alkyl, C3-C20 cycloalkyl, heterocyclyl containing 3 to 20 ring atoms, 6 to 14-membered aryl and 5 to 14-membered heteroaryl, wherein the alkyl, cycloalkyl, heterocyclyl, aryl and heteroaryl are each optionally substituted by one or more groups selected from the group consisting of halogen, cyano, hydroxy, amino, C1-C20 alkyl, C1-C20 haloalkyl, C1-C20 hydroxyalkyl, C1-C20 alkoxy, C3-C20 cycloalkyl, heterocyclyl containing 3 to 20 ring atoms, 6 to 14-membered aryl, 5 to 14-membered heteroaryl, carboxyl and alkoxycarbonyl; preferably, R2 is C1-C20 alkyl;

ring A is selected from the group consisting of 6 to 14-membered aryl and 5 to 14-membered heteroaryl, wherein the aryl and heteroaryl are each optionally substituted by one or more groups selected from the group consisting of halogen, cyano, C1-C20 alkyl, C1-C20 haloalkyl, C1-C20 hydroxyalkyl, C3-C20 cycloalkyl, C1-C20 alkoxy, heterocyclyl containing 3 to 20 ring atoms, 6 to 14-membered aryl, 5 to 14-membered heteroaryl, carboxyl and alkoxycarbonyl; the ring A is preferably 6 to 14-membered aryl and more preferably phenyl;

R4 and R5 are each independently selected from the group consisting of hydrogen atom, halogen, cyano, hydroxy, C1-C20 alkyl, C1-C20 haloalkyl, C1-C20 alkoxy, C1-C20 haloalkoxy, C3-C20 cycloalkyl, heterocyclyl containing 3 to 20 ring atoms, 6 to 14-membered aryl and 5 to 14-membered heteroaryl;

or R4 and R5 are taken together to form a C3-C20 cycloalkyl or heterocyclyl containing 3 to 20 ring atoms;

R6 and R7 are each independently selected from the group consisting of hydrogen atom, C1-C20 alkyl, C1-C20 alkoxy, C3-C20 cycloalkyl, heterocyclyl containing 3 to 20 ring atoms, 6 to 14-membered aryl and 5 to 14-membered heteroaryl, wherein the alkyl, cycloalkyl, heterocyclyl, aryl and heteroaryl are each independently and optionally substituted by one or more groups selected from the group consisting of halogen, cyano, hydroxy, amino, oxo, C1-C20 alkyl, C1-C20 haloalkyl, C1-C20 hydroxyalkyl, C1-C20 alkoxy, C3-C20 cycloalkyl, heterocyclyl containing 3 to 20 ring atoms, 6 to 14-membered aryl, 5 to 14-membered heteroaryl, carboxyl and alkoxycarbonyl; and n is 0, 1 or 2; and PG is an amino-protecting group, preferably tert-butoxycarbonyl.

More preferably, R1 is selected from the group consisting of C3-C6 cycloalkyl, heterocyclyl containing 5 to 6 ring atoms, 6 to 10-membered aryl and 5 to 6-membered heteroaryl, wherein the cycloalkyl, heterocyclyl, aryl and heteroaryl are each optionally substituted by one or more groups selected from the group consisting of halogen, cyano, C1-C6 alkyl, C1-C6 haloalkyl, C1-C6 hydroxyalkyl, C3-C6 cycloalkyl, C1-C6 alkoxy, heterocyclyl containing 5 to 6 ring atoms, 6 to 10-membered aryl, 5 to 6-membered heteroaryl, carboxyl and alkoxycarbonyl;

R2 is selected from the group consisting of hydrogen atom, C1-C6 alkyl, C3-C6 cycloalkyl, heterocyclyl containing 5 to 6 ring atoms, 6 to 10-membered aryl and 5 to 6-membered heteroaryl, wherein the alkyl, cycloalkyl, heterocyclyl, aryl and heteroaryl are each optionally substituted by one or more groups selected from the group consisting of halogen, cyano, hydroxy, amino, C1-C6 alkyl, C1-C6 haloalkyl, C1-C6 hydroxyalkyl, C1-C6 alkoxy, C3-C6 cycloalkyl, heterocyclyl containing 5 to 6 ring atoms, 6 to 10-membered aryl, 5 to 6-membered heteroaryl, carboxyl and alkoxycarbonyl; preferably, R2 is C1-C6 alkyl;

ring A is selected from the group consisting of 6 to 10-membered aryl and 5 to 6-membered heteroaryl, wherein the aryl and heteroaryl are each optionally substituted by one or more groups selected from the group consisting of halogen, cyano, C1-C6 alkyl, C1-C6 haloalkyl, C1-C6 hydroxyalkyl, C3-C6 cycloalkyl, C1-C6 alkoxy, heterocyclyl containing 5 to 6 ring atoms, 6 to 10-membered aryl, 5 to 6-membered heteroaryl, carboxyl and alkoxycarbonyl; the ring A is preferably 6 to 10-membered aryl, and more preferably phenyl;

R4 and R5 are each independently selected from the group consisting of hydrogen atom, halogen, cyano, hydroxy, C1-C6 alkyl, C1-C6 haloalkyl, C1-C6 alkoxy, C1-C6 haloalkoxy, C3-C6 cycloalkyl, heterocyclyl containing 5 to 6 ring atoms, 6 to 10-membered aryl and 5 to 6-membered heteroaryl;

or R4 and R5 are taken together to form a C3-C6 cycloalkyl or heterocyclyl containing 5 to 6 ring atoms;

R6 and R7 are each independently selected from the group consisting of hydrogen atom, C1-C6 alkyl, C3-C6 cycloalkyl, heterocyclyl containing 5 to 6 ring atoms, 6 to 10-membered aryl and 5 to 6-membered heteroaryl, wherein the alkyl, cycloalkyl, heterocyclyl, aryl and heteroaryl are each independently and optionally substituted by one or more groups selected from the group consisting of halogen, cyano, hydroxy, amino, oxo, C1-C6 alkyl, C1-C6 haloalkyl, C1-C6 hydroxyalkyl, C1-C6 alkoxy, C3-C6 cycloalkyl, heterocyclyl containing 5 to 6 ring atoms, 6 to 10-membered aryl, 5 to 6-membered heteroaryl, carboxyl and alkoxycarbonyl; and n is 0, 1 or 2; and PG is an amino-protecting group, preferably tert-butoxycarbonyl.

In another aspect, the present invention relates to a process for preparing the compound of formula (I), or a tautomer, mesomer, racemate, enantiomer, diastereomer, or mixture thereof, or a pharmaceutically acceptable salt thereof according to claim 1, comprising a step of:

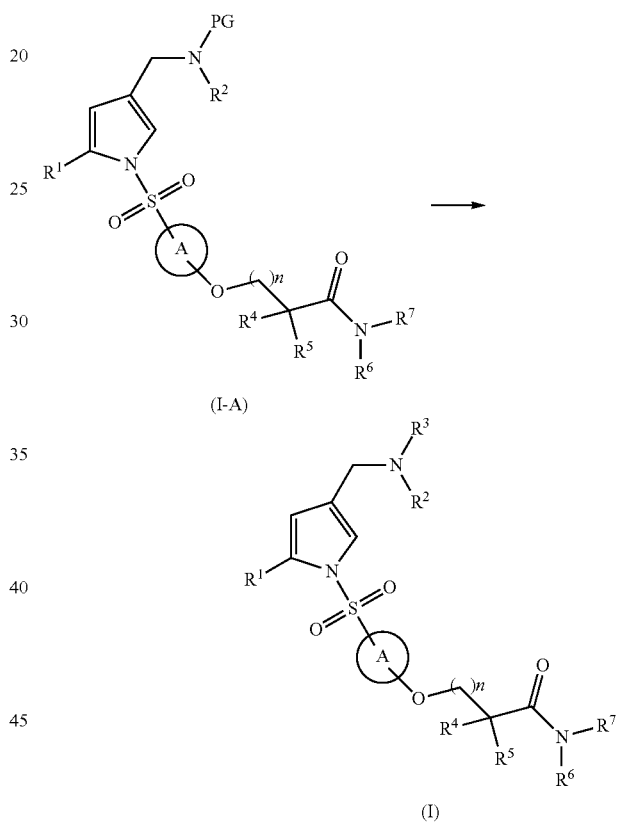

deprotection of the compound of formula (I-A) in a solvent under an acidic condition to obtain a compound of formula (I);

wherein PG is an amino-protecting group, preferably tert-butoxycarbonyl; and R1-R7 are as defined in the compound of formula (I), wherein R3 is preferably hydrogen atom.

In another aspect, the present invention relates to a pharmaceutical composition comprising a therapeutically effective amount of the compound of formula (I), or a tautomer, mesomer, racemate, enantiomer, diastereomer, or mixture thereof, or a pharmaceutically acceptable salt thereof, and a pharmaceutically acceptable carrier, a diluent and an excipient.

In another aspect, the present invention relates to use of the compound of formula (I), or a tautomer, mesomer, racemate, enantiomer, diastereomer, or mixture thereof, or a pharmaceutically acceptable salt thereof or the pharmaceutical composition comprising the same in the preparation of a medicament as a gastric acid secretion inhibitor.

In another aspect, the present invention relates to a method for inhibiting gastric acid secretion, comprising administering to a subject in need thereof a therapeutically effective amount of the compound of formula (I), or a tautomer, mesomer, racemate, enantiomer, diastereomer, or mixture thereof, or a pharmaceutically acceptable salt thereof or the pharmaceutical composition comprising the same.

In another aspect, the present invention relates to the compound of formula (I), or a tautomer, mesomer, racemate, enantiomer, diastereomer, or mixture thereof, or a pharmaceutically acceptable salt thereof or the pharmaceutical composition comprising the same, for use as a gastric acid secretion inhibitor.

In another aspect, the present invention relates to use of the compounds of formula (I), or a tautomer, mesomer, racemate, enantiomer, diastereomer, or mixture thereof, or a pharmaceutically acceptable salt thereof, or the pharmaceutical composition comprising the same in the preparation of a medicament as a H+/K+-adenosine triphosphatase (H+/K+-ATPase) inhibitor.

In another aspect, the present invention relates to a method for inhibiting H+/K+-adenosine triphosphatase (H+/K+-ATPase), comprising administering to a subject in need thereof a therapeutically effective amount of the compound of formula (I), or a tautomer, mesomer, racemate, enantiomer, diastereomer, or mixture thereof, or a pharmaceutically acceptable salt thereof or the pharmaceutical composition comprising the same.

In another aspect, the present invention relates to the compound of formula (I), or a tautomer, mesomer, racemate, enantiomer, diastereomer, or mixture thereof, or a pharmaceutically acceptable salt thereof or the pharmaceutical composition comprising the same, for use as a H+/K+-adenosine triphosphatase (H+/K+-ATPase) inhibitor.

In another aspect, the present invention relates to use of the compound of formula (I), or a tautomer, mesomer, racemate, enantiomer, diastereomer, or mixture thereof, or a pharmaceutically acceptable salt thereof or the pharmaceutical composition comprising the same in the preparation of a medicament as a potassium-competitive acid blocker (P-CAB).

In another aspect, the present invention relates to a method for competitively inhibiting acid secretion by blocking access of potassium ions, comprising administering to a subject in need thereof a therapeutically effective amount of the compound of formula (I), or a tautomer, mesomer, racemate, enantiomer, diastereomer, or mixture thereof, or a pharmaceutically acceptable salt thereof or the pharmaceutical composition comprising the same.

In another aspect, the present invention relates to the compound of formula (I), or a tautomer, mesomer, racemate, enantiomer, diastereomer, or mixture thereof, or a pharmaceutically acceptable salt thereof or the pharmaceutical composition comprising the same, for use as a potassium-competitive acid blocker (P-CAB).

The present invention further relates to use of the compound of formula (I), or a tautomer, mesomer, racemate, enantiomer, diastereomer, or mixture thereof, or a pharmaceutically acceptable salt thereof or the pharmaceutical composition comprising the same in the preparation of a medicament for treating or preventing peptic ulcer, Zollinger-Ellison syndrome, gastritis, erosive esophagitis, reflux esophagitis, symptomatic gastroesophageal reflux disease (symptomatic GERD), Barrett's esophagitis, functional dyspepsia, *helicobacter pylori* infection, gastric cancer, gastric MALT lymphoma, ulcer caused by a nonsteroidal anti-inflammatory drug (NSAID) or hyperacidity or ulcer caused by postoperative stress; or in the preparation of a medicament for inhibiting upper gastrointestinal bleeding caused by peptic ulcer, acute stress ulcer, hemorrhagic gastritis or invasive stress. Among them, the peptic ulcer includes, but is not limited to, gastric ulcer, duodenal ulcer or stomal ulcer; and the symptomatic gastroesophageal reflux disease (symptomatic GERD) includes, but not limited to, non-erosive reflux disease or gastroesophageal reflux disease without oesophagitis.

In another aspect, the present invention relates to a method for treating or preventing peptic ulcer, Zollinger-Ellison syndrome, gastritis, erosive esophagitis, reflux esophagitis, symptomatic gastroesophageal reflux disease (GERD), Barrett's esophagitis, functional dyspepsia, *helicobacter pylori* infection, gastric cancer, gastric MALT lymphoma, ulcer caused by a nonsteroidal anti-inflammatory drug (NSAID) or hyperacidity or ulcer caused by postoperative stress; or a method for inhibiting upper gastrointestinal bleeding caused by peptic ulcer, acute stress ulcer, hemorrhagic gastritis or invasive stress, comprising administering to a subject in need thereof a therapeutically effective amount of the compound of formula (I), or a tautomer, mesomer, racemate, enantiomer, diastereomer, or mixture thereof, or a pharmaceutically acceptable salt thereof or the pharmaceutical composition comprising the same. Among them, the peptic ulcer includes, but is not limited to, gastric ulcer, duodenal ulcer or stomal ulcer; and the symptomatic gastroesophageal reflux disease (symptomatic GERD) includes, but is not limited to, non-erosive reflux disease or gastroesophageal reflux disease without oesophagitis.

In another aspect, the present invention further relates to the compound of formula (I), or a tautomer, mesomer, racemate, enantiomer, diastereomer, or mixture thereof, or a pharmaceutically acceptable salt thereof or the pharmaceutical composition comprising the same, for use as a medicament for treating or preventing peptic ulcer, Zollinger-Ellison syndrome, gastritis, erosive esophagitis, reflux esophagitis, symptomatic gastroesophageal reflux disease (GERD), Barrett's esophagitis, functional dyspepsia, *helicobacter pylori* infection, gastric cancer, gastric MALT lymphoma, ulcer caused by a nonsteroidal antiinflammatory drug (NSAID) or hyperacidity or ulcer caused by postoperative stress; or for use as a medicament for inhibiting upper gastrointestinal bleeding caused by peptic ulcer, acute stress ulcer, hemorrhagic gastritis or invasive stress. Among them, the peptic ulcer includes, but is not limited to, gastric ulcer, duodenal ulcer or stomal ulcer; and the symptomatic gastroesophageal reflux disease (symptomatic GERD) includes, but is not limited to, non-erosive reflux disease or gastroesophageal reflux disease without oesophagitis.

DETAILED DESCRIPTION OF THE INVENTION

Unless otherwise stated, the following terms which are used in the description and the claims have the following meanings.

"Alkyl" refers to a saturated aliphatic hydrocarbon group, namely a straight chain or branched chain group containing 1 to 20 carbon atoms. The alkyl is preferably an alkyl containing 1 to 10 carbon atoms, and more preferably alkyl containing 1 to 6 carbon atoms. Non-limiting examples comprise methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched chain isomers thereof and the like. More preferably, the alkyl is a lower alkyl containing 1 to 6 carbon atoms, and the non-limiting examples comprise methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. The alkyl can be substituted or unsubstituted. When the alkyl is substituted, the substituent can be substituted at any available connection point, and is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, oxo, amino, haloalkyl, hydroxyalkyl, carboxyl and alkoxycarbonyl.

"Cycloalkyl" refers to a saturated or partially unsaturated monocyclic or polycyclic cyclic hydrocarbon substituent, which comprises 3 to 20 carbon atoms, preferably 3 to 12 carbon atoms, and more preferably 3 to 10 carbon atoms, and most preferably 3 to 6 carbon atoms. The non-limiting examples of monocyclic cycloalkyl comprise cyclopropyl, cyclobutyl, cyclopentyl, cyclopentenyl, cyclohexyl, cyclohexenyl, cyclohexadienyl, cycloheptyl, cycloheptatrienyl, cyclooctyl and the like, preferably cyclopropyl and cyclohexenyl. Polycyclic cycloalkyl includes a cycloalkyl having a spiro ring, fused ring and bridged ring.

"Spirocycloalkyl" refers to a 5 to 20-membered polycyclic group with rings connected through one common carbon atom (called a spiro atom), wherein these rings can contain one or more double bonds, but there is no ring having a completely conjugated π electron system. The spirocycloalkyl is preferably 6 to 14-membered, and more preferably 7 to 10-membered. The spirocycloalkyl can be divided into monospirocycloalkyl, dispirocycloalkyl or polyspirocycloalkyl, preferably monospirocycloalkyl and dispirocycloalkyl according to the number of spiro atoms shared between the rings. More preferably, the spirocycloalkyl is a 4-membered/4-membered, 4-membered/5-membered, 4-membered/6-membered, 5-membered/5-membered or 5-membered/6-membered monospirocycloalkyl. Non-limiting examples of the spirocycloalkyl include:

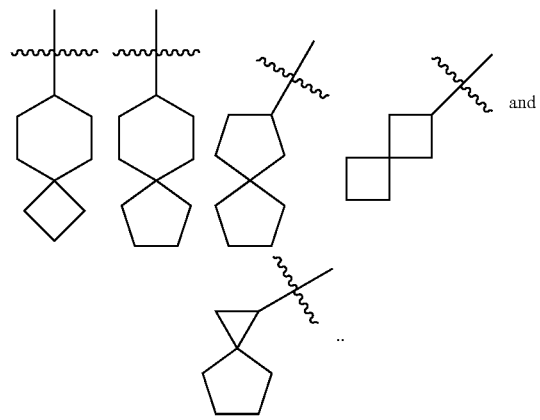

"Fused-cycloalkyl" refers to a 5 to 20-membered full carbon polycyclic group in which each ring in the system shares an adjacent pair of carbon atoms with another ring, wherein one or more rings can contain one or more double bonds, but there is no ring having a completely conjugated π electron system. The fused-cycloalkyl is preferably 6 to 14-membered, and more preferably 7 to 10-membered. According to the number of membered rings, the fused-cycloalkyl can be divided into dicyclo-, tricyclo-, tetracyclo- or polycyclo-fused-cycloalkyl, preferably dicyclo- or tricyclo-fused-cycloalkyl, and more preferably 5-membered/5-membered or 5-membered/6-membered dicyclo-fused-cycloalkyl. Non-limiting examples of the fused-cycloalkyl include:

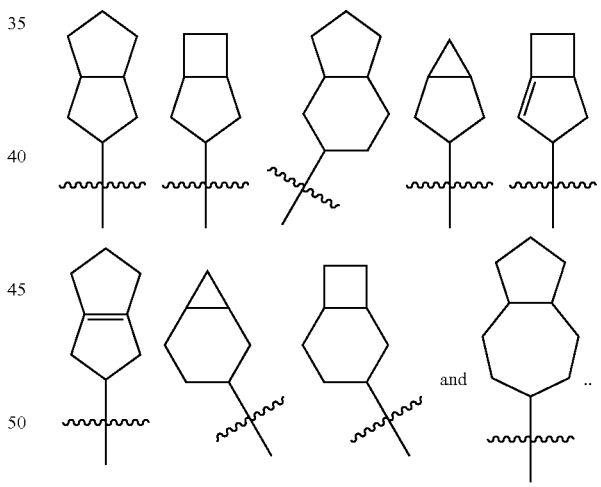

"Bridged-cycloalkyl" refers to a 5 to 20-membered full carbon polycyclic group in which any two rings in the system share two disconnected carbon atoms, wherein these rings can contain one or more double bonds, but there is no ring having a completely conjugated π electron system. The bridged-cycloalkyl is preferably 6 to 14-membered, and more preferably 7 to 10-membered. According to the number of membered rings, the bridged-cycloalkyl can be divided into dicyclo-, tricyclo-, tetracyclo- or polycyclo-bridged-cycloalkyl, preferably dicyclo-, tricyclo- or tetracyclo-bridged-cycloalkyl, and more preferably dicyclo- or tricyclo-bridged-cycloalkyl. Non-limiting examples of the bridged-cycloalkyl comprise:

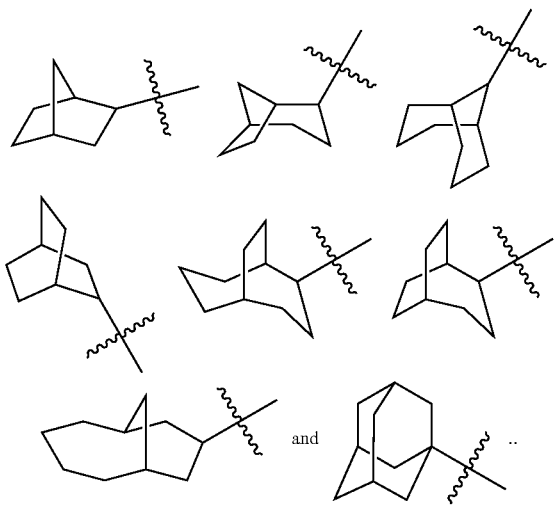

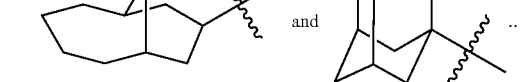

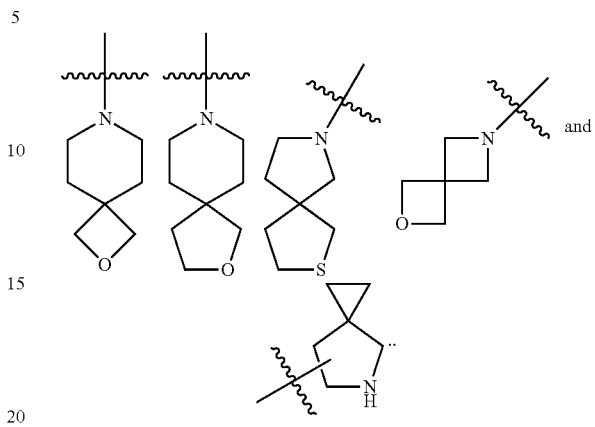

The cycloalkyl can be fused to the ring of aryl, heteroaryl or heterocyclyl, wherein the ring connected with the parent structure is the cycloalkyl, and non-limiting examples include indanyl, tetrahydronaphthyl, benzocycloheptylalkyl and the like. The cycloalkyl can be optionally substituted or unsubstituted. When the cycloalkyl is substituted, the substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, oxo, amino, haloalkyl, hydroxyalkyl, carboxyl and alkoxycarbonyl.

"Heterocyclyl" refers to a saturated or partially unsaturated monocyclic or polycyclic hydrocarbon substituent including 3 to 20 ring atoms, wherein one or more ring atoms are heteroatoms selected from nitrogen, oxygen or $S(O)_m$ (wherein m is an integer selected from 0 to 2), but the cyclic part does not include —O—O—, —O—S— or —S—S—, and remaining ring atoms are carbon. Preferably, the heterocyclyl comprises 3 to 12 ring atoms, wherein 1 to 4 of them are heteroatoms, more preferably, the heterocyclyl ring comprises 3 to 10 ring atoms, and most preferably, the heterocyclyl ring comprises 5 to 6 ring atoms. Non-limiting examples of the monocyclic heterocyclyl comprise pyrrolidinyl, piperidinyl, piperazinyl, morpholinyl, thiomorpholinyl, homopiperazinyl, pyranyl, tetrahydrofuranyl and the like. Polycyclic heterocyclyl includes a heterocyclyl having a spiro ring, fused ring and bridged ring.

"Spiroheterocyclyl" refers to a 5 to 20-membered polycyclic heterocyclyl group with rings connected through one common atom (called a spiro atom) shared between the rings, wherein one or more ring atoms are heteroatoms selected from nitrogen, oxygen or $S(O)_m$ (wherein m is an integer selected from 0 to 2), and remaining ring atoms are carbon. These rings can contain one or more double bonds, but there is no ring having a completely conjugated π electron system. The spiroheterocyclyl is preferably 6 to 14-membered, and more preferably 7 to 10-membered. The spirocycloalkyl can be divided into monospiroheterocyclyl, dispiroheterocyclyl or polyspiroheterocyclyl, preferably monospiroheterocyclyl and dispiroheterocyclyl according to the number of the spiro atoms shared between the rings. More preferably, the spiroheterocyclyl is 4-membered/4-membered, 4-membered/5-membered, 4-membered/6-membered, 5-membered/5-membered or 5-membered/6-membered monospiroheterocyclyl. Non-limiting examples of the spiroheterocyclyl include:

"Fused-heterocyclyl" refers to a 5 to 20-membered polycyclic heterocyclic group in which each ring in the system shares an adjacent pair of atoms with another ring, wherein one or more rings can contain one or more double bonds, but there is no ring having a completely conjugated π electron system, and wherein one or more ring atoms are heteroatoms selected from nitrogen, oxygen or $S(O)_m$ (wherein m is an integer selected from 0 to 2), and remaining ring atoms are carbon. The fused-heterocyclyl is preferably 6 to 14-membered, and more preferably 7-10-membered. According to the number of membered rings, the fused-heterocyclyl can be divided into dicyclo-, tricyclo-, tetracyclo- or polycyclo-fused-heterocyclyl, preferably dicyclo- or tricyclo-fused-heterocyclyl, and more preferably 5-membered/5-membered or 5-membered/6-membered dicyclo-fused-heterocyclyl. Non-limiting examples of the fused-heterocyclyl comprise:

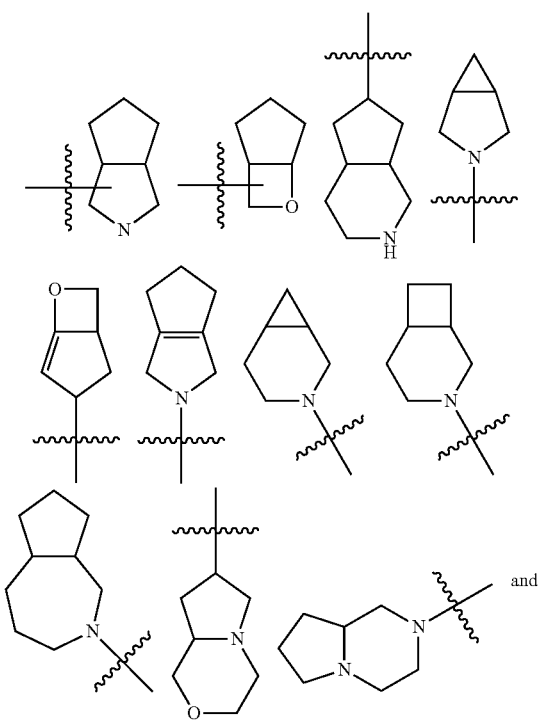

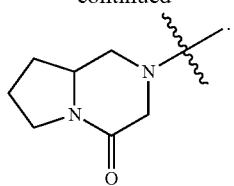

"Bridged-heterocyclyl" refers to a 5 to 14-membered polycyclic heterocyclic group in which any two rings in the system share two disconnected atoms, the rings can contain one or more double bonds, but there is no ring having a completely conjugated π electron system, and one or more ring atoms are heteroatoms selected from nitrogen, oxygen or $S(O)_m$ (wherein m is an integer selected from 0 to 2), and remaining ring atoms are carbon. The bridged-heterocyclyl is preferably 6 to 14-membered, and more preferably 7 to 10-membered. According to the number of membered rings, the bridged-heterocyclyl can be divided into dicyclo-, tricyclo-, tetracyclo- or polycyclo-bridged-heterocyclyl, preferably dicyclo-, tricyclo- or tetracyclo-bridged-heterocyclyl, and more preferably dicyclo- or tricyclo-bridged-heterocyclyl. Non-limiting examples of the bridged-heterocyclyl include:

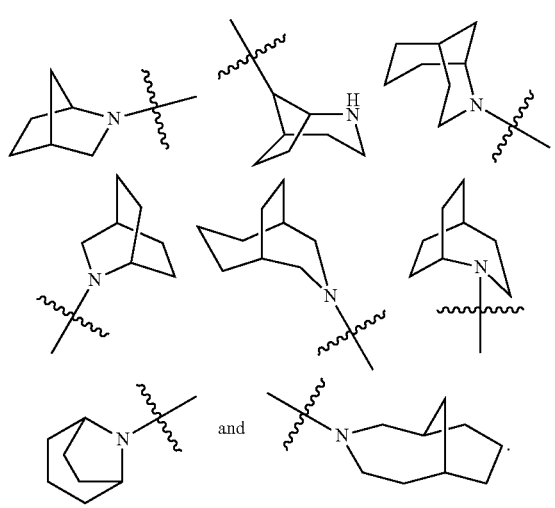

The heterocyclyl can be fused to the ring of aryl, heteroaryl or cycloalkyl, wherein the ring connected with the parent structure is the heterocyclyl, and non-limiting examples include:

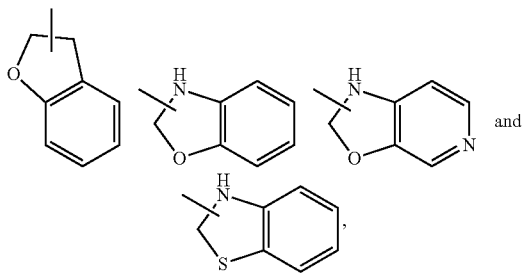

and the like.

The heterocyclyl can be optionally substituted or unsubstituted. When the heterocyclyl is substituted, the substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, oxo, amino, haloalkyl, hydroxyalkyl, carboxyl and alkoxycarbonyl.

"Aryl" refers to a 6 to 14-membered full carbon monocyclic ring or fused polycyclic ring (namely, the rings sharing an adjacent pair of carbon atoms) with a conjugated π electron system. The aryl is preferably 6 to 10-membered, more preferably phenyl and naphthyl, and most preferably phenyl. The aryl can be fused to the ring of heteroaryl, heterocyclyl or cycloalkyl, wherein the ring connected with the parent structure is aryl, and non-limiting examples include:

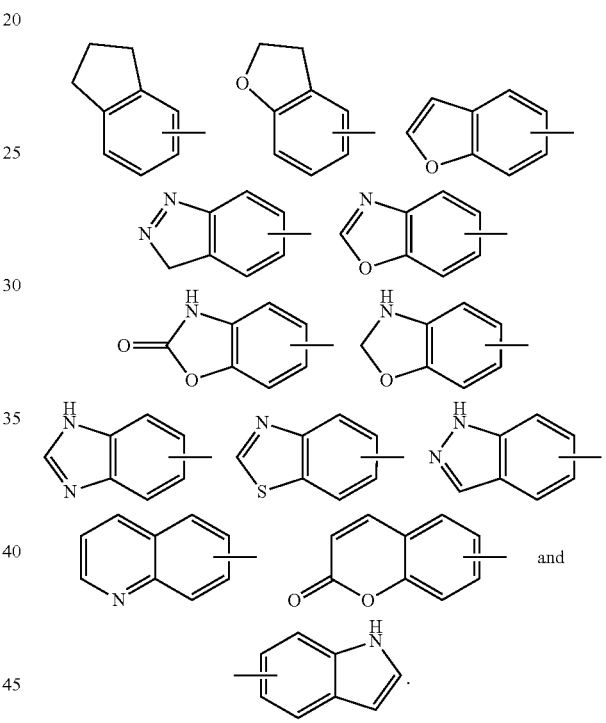

The aryl can be substituted or unsubstituted. When the aryl is substituted, the substituent is preferably one or more groups independently selected from alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, amino, haloalkyl, hydroxyalkyl, carboxyl and alkoxycarbonyl.

"Heteroaryl" refers to a 5 to 14-membered aryl, wherein 1 to 4 heteroatoms are taken as the ring atoms, the remaining ring atoms are carbon, and the heteroatoms comprise oxygen, sulfur and nitrogen. The heteroaryl is preferably 5 to 10-membered. The heteroaryl is preferably 5-membered or 6-membered, such as furyl, thienyl, pyridyl, pyrrolyl, N-alkyl pyrrolyl, pyrimidinyl, pyrazinyl, imidazolyl, tetrazolyl and the like. The heteroaryl can be fused to the ring of aryl, heterocyclyl or cycloalkyl, wherein the ring connected with the parent structure is heteroaryl, and non-limiting examples include:

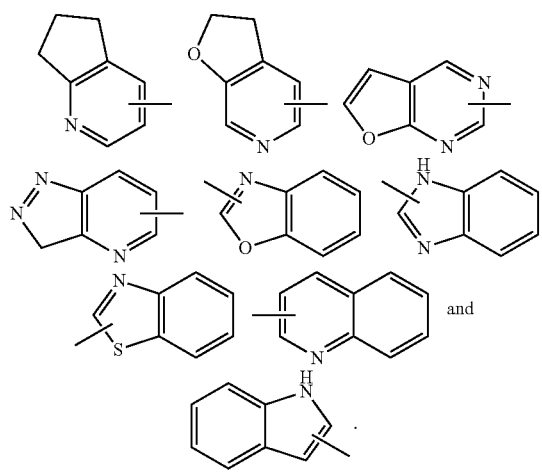

The heteroaryl can be optionally substituted or unsubstituted. When the heteroaryl is substituted, the substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, amino, haloalkyl, hydroxyalkyl, carboxyl and alkoxycarbonyl.

"Alkoxy" refers to an —O-(alkyl) and an —O-(unsubstituted cycloalkyl) group, wherein the alkyl is as defined above. Non-limiting examples include methoxy, ethoxy, propoxy, butoxy, cyclopropyloxy, cyclobutyloxy, cyclopentyloxy, cyclohexyloxy and the like. The alkoxy can be optionally substituted or unsubstituted. When the alkoxy is substituted, the substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, amino, haloalkyl, hydroxyalkyl, carboxyl and alkoxycarbonyl.

"Haloalkyl" refers to an alkyl substituted by one or more halogens, wherein the alkyl is as defined above.

"Hydroxy" refers to a —OH group.

"Hydroxyalkyl" refers to an alkyl substituted by hydroxy, wherein the alkyl is as defined above.

"Halogen" refers to fluorine, chlorine, bromine or iodine.

"Amino" refers to —NH2.

"Cyano" refers to —CN.

"Nitro" refers to —NO2.

"Benzyl" refers to —CH2-phenyl.

"Oxo" refers to =O.

"Carboxyl" refers to —C(O)OH.

"Alkoxycarbonyl" refers to an —C(O)O (alkyl) or (cycloalkyl) group, wherein the alkyl and cycloalkyl are as defined above.

"Amino-protecting group" is used for protecting amino with a group which is easy to remove, thereby keeping amino unchanged when other parts of the molecule undergo a reaction. Non-limiting examples include formyl, alkylcarbonyl, alkoxycarbonyl, benzoyl, aralkylcarbonyl, aralkyloxycarbonyl, trityl, phthaloyl, N, N-dimethylaminomethylene, substituted silyl and the like. These groups can be optionally substituted by 1 to 3 substituents selected from the group consisting of halogen, alkoxy and nitro. The amino-protecting group is preferably tert-butoxycarbonyl.

"Optional" or 'optionally" means that the event or the circumstance which is described subsequently can, but not necessarily, occur, and the description includes the instances in which the event or the circumstance occurs or does not occur. For example, "the heterocyclic group optionally substituted by alkyl" means that an alkyl group can be, but need not be, present, and the description includes situations in which the heterocyclic group is substituted by an alkyl and the heterocyclic group is not substituted by an alkyl.

"Substituted" means that one or more hydrogen atoms, preferably up to 5 and more preferably 1 to 3 hydrogen atoms in the group are each independently substituted by the corresponding number of substituents. Obviously, the substituents are only positioned in their possible chemical positions, and the possible or impossible substitutions can be determined (through experiments or theory) by those skilled in the art without paying excessive efforts. For example, the combination of amino or hydroxy group having free hydrogen and carbon atoms having unsaturated bonds (such as olefinic) may be unstable.

"Pharmaceutical composition" refers to a mixture of one or more of the compounds described herein or the physiological/pharmaceutical salts or prodrugs and other chemical components, as well as other components, such as a physiological/pharmaceutical carrier and an excipient. The object of the pharmaceutical composition is to promote the drug administration to an organism, thereby being conducive to the absorption of active ingredients and realizing biological activity.

Synthesis Method of Compounds of the Invention

In order to complete the synthesis object of the present invention, the present invention applies the following synthesis technical solution:

A process of preparing a compound of formula (II) of the invention, or a tautomer, racemate, enantiomer, diastereomer, or mixture thereof, or a pharmaceutically acceptable salt thereof, comprising the following steps of:

Scheme 1:

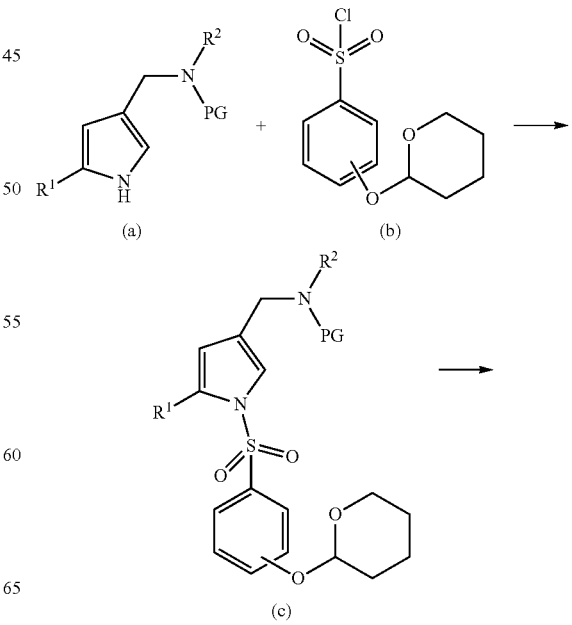

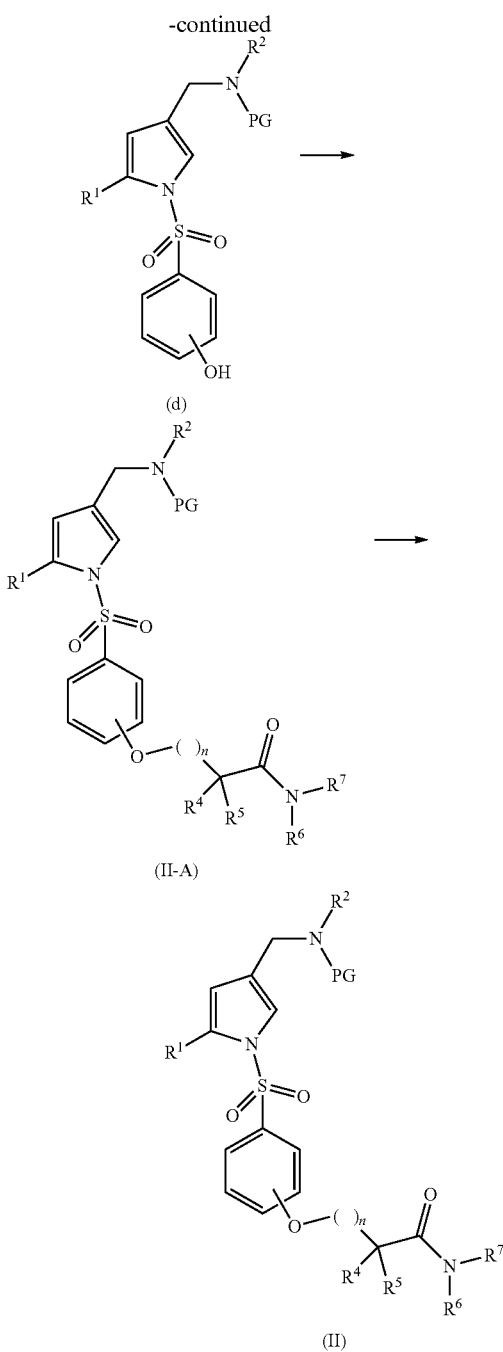

reacting a pyrrole compound (a) with a benzenesulfonyl chloride (b) in a solvent under an alkaline condition via a nucleophilic substitution reaction to obtain a benzenesulfonyl-substituted pyrrole compound (c); deprotecting the compound (c) in a solvent under an acidic condition to obtain a compound (d);

either reacting the compound (d) with a haloacetamide compound in a solvent under an alkaline condition via a nucleophilic reaction to obtain a benzenesulfonyl-substituted pyrrole compound (II-A); or reacting the compound (d) with a hydroxy-substituted amide compound in a solvent under the catalysis of a catalyst via a condensation reaction to obtain a benzenesulfonyl-substituted pyrrole compound (II-A); and deprotecting the benzenesulfonyl-substituted pyrrole compound (II-A) in a solvent under an acidic condition to obtain a compound of formula (II), wherein n and R1-R7 are as defined in the compound of formula (II), wherein R3 is preferably hydrogen atom; PG is an amino-protecting group, preferably tert-butoxycarbonyl.

The structure of the haloacetamide compound is as follows:

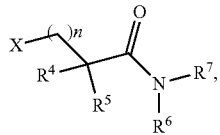

wherein X is halogen, n and $R^4$-$R^7$ are as defined in the compound of formula (II);

The structure of the hydroxy-substituted amide compound is as follows:

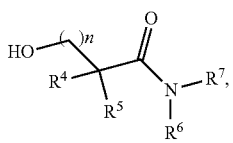

wherein n and $R^4$-$R^7$ are as defined in the compound of formula (II).

The reagent for providing an acidic condition includes, but is not limited to trifluoroacetic acid, formic acid, acetic acid, hydrochloric acid, sulfuric acid, methanesulfonic acid and p-toluenesulfonic acid.

The reagent for providing an alkaline condition includes an organic base and an inorganic base, wherein the organic base includes, but is not limited to, triethylamine, N,N-diisopropylethylamine, n-butyl lithium and potassium tert-butoxide, and the inorganic base includes, but is not limited to, sodium hydride, sodium carbonate, sodium bicarbonate, potassium carbonate, potassium bicarbonate or cesium carbonate.

The reductant includes, but is not limited to, sodium borohydride, sodium triacetoxyborohydride, sodium cyanoborohydride or lithium aluminum hydride.

The used solvent includes but not limited to tetrahydrofuran, dichloromethane, 1,4-dioxane, water, methanol, ethanol, dimethyl sulfoxide or N,N-dimethylformamide.

PREFERRED EMBODIMENTS

The following examples serve to illustrate the invention, but these examples should not be considered as limiting the scope of the present invention.

If specific conditions for the experimental method are not specified in the examples of the present invention, they are generally in accordance with conventional conditions or recommended conditions of the raw materials and the product manufacturer. The reagents without a specific source indicated are commercially available, conventional reagents.

EXAMPLES

The structures of compounds were identified by nuclear magnetic resonance (NMR) or mass spectrometry (MS). NMR was determined by a Bruker AVANCE-400 NMR machine, the solvents for determination were deuterated dimethylsulfoxide (DMSO-d6), deuterated chloroform (CDCl$_3$)

and deuterated methanol (CD₃OD), the internal standard was tetramethylsilane (TMS), and the chemical shift is given out by taking $10^{-6}$ (ppm) as unit.

MS was determined by a FINNIGAN LCQAd (ESI) mass spectrometer (manufacturer: Thermo; model: Finnigan LCQ advantage MAX).

High performance liquid chromatography (HPLC) was determined on an Agilent 1200DAD high pressure liquid chromatographic instrument (Sunfire C18 150×4.6 mm chromatographic column) and a Waters 2695-2996 high pressure liquid chromatographic instrument (Gimini C18 150×4.6 mm chromatographic column).

The thin layer chromatographic silica gel plate used was a Yantai Huanghai HSGF254 or Qingdao GF254 silica gel plate. The dimension of the plates used in thin layer chromatography (TLC) was 0.15 mm to 0.2 mm, and the dimension of the plates used in product purification was 0.4 mm to 0.5 mm.

Yantai Huanghai silica gel of 200-300 meshes was generally used as a carrier for column chromatography.

The known starting raw materials of the present invention can be synthesized by adopting or according to the known methods in the art, or be purchased from ABCR GmbH & Co. KG, Acros Organnics, Aldrich Chemical Company, Accela ChemBio Inc, Darui Chemical Co., Ltd. and other companies.

Unless otherwise stated in the examples, the reaction is performed under an argon atmosphere or a nitrogen atmosphere.

The argon atmosphere or the nitrogen atmosphere means that a reaction flask is equipped with about a 1 L argon or nitrogen balloon.

A hydrogen atmosphere means that a reaction flask is equipped with about a 1 L hydrogen balloon.

Pressurization and hydrogenation reactions were performed with a Parr 3916EKX type hydrogenation spectrometer and a clear blue QL-500 type hydrogen generator or an HC2-SS type hydrogenation spectrometer.

During the hydrogenation reaction, the reaction system was generally vacuumed and filled with hydrogen, with the above operation repeated three times.

Microwave reaction was performed with a CEM Discover-S 908860 type microwave reactor.

Unless otherwise specified in the examples, a solution in the reaction refers to an aqueous solution.

Unless otherwise stated in the examples, the reaction temperature was room temperature.

The room temperature was the most appropriate reaction temperature, and the range of the temperature was 20° C. to 30° C.

The reaction process was monitored by thin layer chromatography (TLC), and the system of developing solvent included: A: dichloromethane and methanol, B: n-hexane and ethyl acetate, C: petroleum ether and ethyl acetate, D: acetone. The ratio of the volume of the solvent was adjusted according to the polarity of the compounds.

The elution system for purification of the compounds by column chromatography and thin layer chromatography included: A: dichloromethane and methanol system, B: n-hexane and ethyl acetate system, C: n-hexane and acetone, D: n-hexane, E: ethyl acetate. The volume of the solvent was adjusted according to the polarity of the compounds, and sometimes a little alkaline reagent, such as triethylamine, or acidic reagent, was also added.

Example 1

2-(3-((2-(2-Fluorophenyl)-4-((methylamino)methyl)-1H-pyrrol-1-yl)sulfonyl)phenoxy)-N-methylacetamide

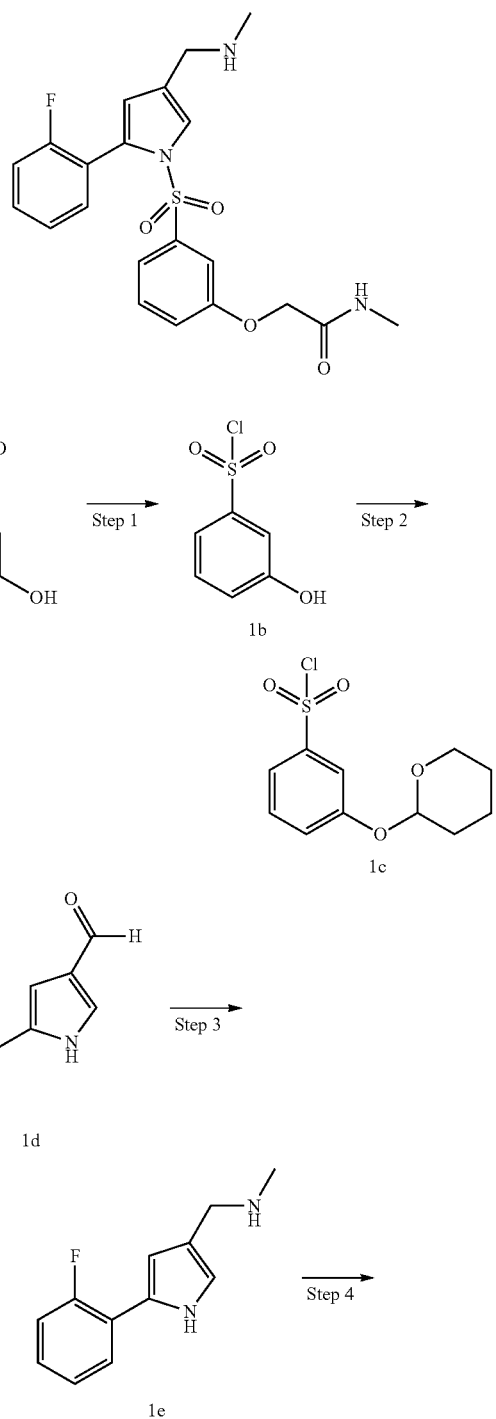

29
-continued

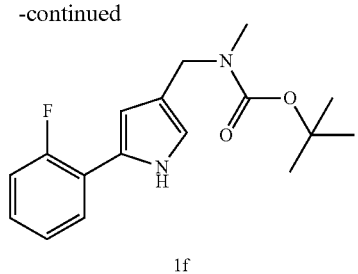

1f

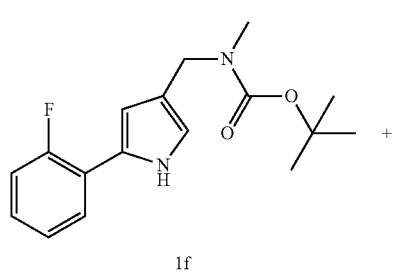

1f

+

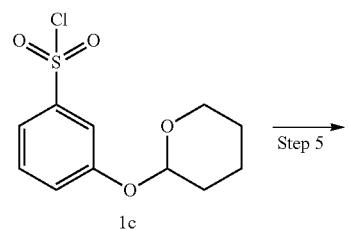

1c

Step 5 →

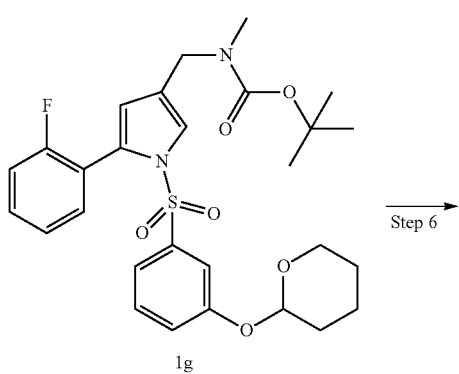

1g

Step 6 →

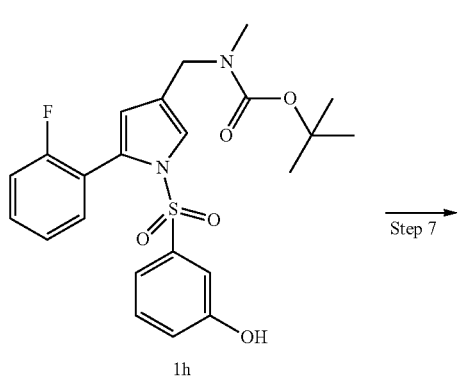

1h

Step 7 →

30
-continued

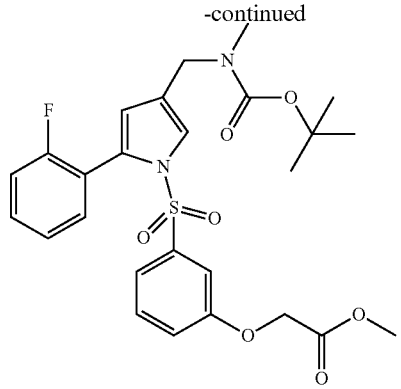

1i

Step 8 →

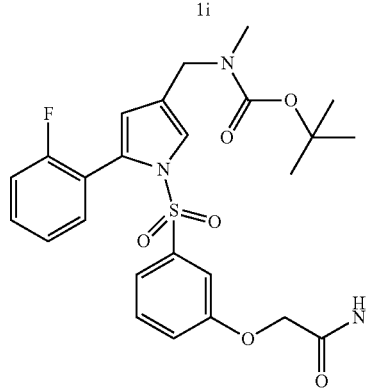

1j

Step 9 →

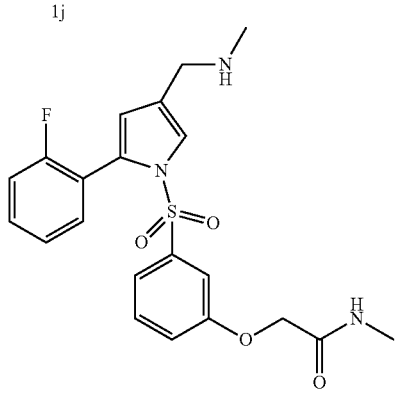

1

Step 1

3-Hydroxyphenyl-1-sulfonyl chloride

3-Hydroxybenzenesulfonic acid 1a (5.6 g, 0.03 mol, prepared by a known method disclosed in "*Journal of Organic Chemistry*, 1984, 49(25), 4917-4923") was dissolved in 60 mL of thionyl chloride, followed by addition of 0.25 mL of N,N-dimethylformamide. The reaction solution was uniformly stirred, and then heated up to 60° C. and reacted for 5 h. The reaction solution was concentrated under reduced pressure. 100 mL of water were added to the resulting residue, and the reaction solution was extracted with ethyl acetate (100 mL×3). The organic phases were combined, dried over anhydrous sodium sulfate, filtered, and the filtrate was concentrated under reduced pressure. The resulting residue was purified by silica gel column chromatography with elution system C to obtain the title product 3-hydroxyphenyl-1-sulfonyl chloride 1b (1.6 g, a light red oil) in 76% yield.

Step 2

3-((Tetrahydro-2H-pyran-2-yl)oxy)phenyl-1-sulfonyl chloride

3-Hydroxyphenyl-1-sulfonyl chloride 1b (1.0 g, 5.2 mmol), 3,4-dihydro-2H-pyrane (0.87 g, 10 mmol) and 4-methylbenzenesulfonic acid pyridine salt (100 mg, 0.4 mmol) were dissolved in 100 mL of dichloromethane, and the reaction solution was stirred for 1 h. The reaction solution was concentrated under reduced pressure. 100 mL of water were added to the resulting residue, and the reaction solution was extracted with dichloromethane (100 mL×3). The organic phases were combined, dried over anhydrous sodium sulfate, filtered, and the filtrate was concentrated under reduced pressure. The resulting residue was purified by silica gel column chromatography with elution system C to obtain the title product 3-((tetrahydro-2H-pyran-2-yl)oxy)phenyl-1-sulfonyl chloride 1c (1.18 g, a colorless oil) in 83% yield.
MS m/z (ESI): 193.1 [M−83]

Step 3

1-(5-(2-Fluorophenyl)-1H-pyrrol-3-yl)-N-methyl-methanamine 5-(2-Fluorophenyl)-1H-pyrrol-3-carboxaldehyde 1d (1.89 g, 10 mmol, prepared by a known method disclosed in "*Journal of Medicinal Chemistry*", 2012, 55(9), 4446-4456) was dissolved in 20 mL of methylamine, and the reaction solution was stirred for 1 h. Sodium borohydride (1.14 g, 30 mmol) was added and continuously stirred for 1 h. 10 mL of water were added to the reaction solution, and the reaction solution was concentrated under reduced pressure to obtain the title product 1-(5-(2-fluorophenyl)-1H-pyrrol-3-yl)-N-methyl-methanamine 1e (2.0 g, a yellow oil), which was used directly in the next step.

Step 4 tert-Butyl ((5-(2-fluorophenyl)-1H-pyrrol-3-yl)methyl)(methyl)carbamate 1-(5-(2-Fluorophenyl)-1H-pyrrol-3-yl)-N-methylmethanamine 1e (4.2 g, 20.6 mmol), di-tert-butyl dicarbonate (9 g, 41.2 mmol) and 11 mL of triethylamine were dissolved in 50 mL of dichloromethane, and the reaction solution was stirred for 2 h. 40 mL of saturated ammonium chloride solution were added, and the reaction solution was extracted with dichloromethane (30 mL×3). The organic phases were combined, dried over anhydrous sodium sulfate, filtered, and the filtrate was concentrated under reduced pressure. The resulting residue was purified by silica gel column chromatography with elution system C to obtain the title product tert-butyl ((5-(2-fluorophenyl)-1H-pyrrol-3-yl)methyl)(methyl)carbamate 1f (4.92 g, a red solid) in 94% yield.
MS m/z (ESI): 249.2 [M−55]

Step 5 tert-Butyl ((5-(2-fluorophenyl)-1-((3-((tetrahydro-2H-pyran-2-yl)oxy)phenyl)sulfonyl)-1H-pyrrol-3-yl)methyl)(methyl)carbamate tert-Butyl ((5-(2-fluorophenyl)-1H-pyrrol-3-yl)methyl)(methyl)carbamate 1f (0.45 g, 1.5 mmol) was dissolved in 10 mL of N,N-dimethylformamide, and the reaction solution was cooled to 0° C. in an ice bath. Sodium hydride (180 mg, 60%) was added, and then the reaction solution was stirred for 1 h. 3-((Tetrahydro-2H-pyran-2-yl)oxy)phenyl-1-sulfonyl chloride 1c (0.82 g, 3.0 mmol) was added and the reaction solution was continuously stirred for 15 min. After removing the ice bath, a saturated ammonium chloride solution was added to quench the reaction, and the reaction solution was extracted with ethyl acetate (50 mL×2). The organic phases were combined, washed with saturated ammonium chloride solution, dried over anhydrous sodium sulfate, filtered, and the filtrate was concentrated under reduced pressure. The resulting residue was purified by silica gel column chromatography with elution system B to obtain the title product tert-butyl ((5-(2-fluorophenyl)-1-((3-((tetrahydro-2H-pyran-2-yl)oxy)phenyl)sulfonyl)-1H-pyrrol-3-yl)methyl)(methyl)carbamate 1g (0.45 g, a red oil) in 56% yield.

Step 6 tert-Butyl ((5-(2-fluorophenyl)-1-((3-hydroxyphenyl)sulfonyl)-1H-pyrrol-3-yl)methyl)(methyl)carbamate tert-Butyl ((5-(2-fluorophenyl)-1-((3-((tetrahydro-2H-pyran-2-yl)oxy)phenyl)sulfonyl)-1H-pyrrol-3-yl)methyl)(methyl)carbamate 1g (0.45 g, 0.83 mmol) was dissolved in 5 mL of methanol, followed by addition of p-toluenesulfonic acid (16 mg, 0.08 mmol), and then the reaction solution was stirred for 3 h. The reaction solution was concentrated under reduced pressure, and the resulting residue was purified by silica gel column chromatography with elution system B to obtain the title product tert-butyl ((5-(2-fluorophenyl)-1-((3-hydroxyphenyl)sulfonyl)-1H-pyrrol-3-yl)methyl)(methyl)carbamate 1h (0.35 g, a red oil) in 92% yield.
MS m/z (ESI): 405.1 [M−55]

Step 7

Methyl 2-(3-((4-(((tert-butoxycarbonyl)(methyl)amino)methyl)-2-(2-fluorophenyl)-1H-pyrrol-1-yl)sulfonyl)phenoxy)acetate tert-Butyl ((5-(2-fluorophenyl)-1-((3-hydroxyphenyl)sulfonyl)-1H-pyrrol-3-yl)methyl)(methyl)carbamate 1h (100 mg, 0.22 mmol), methyl bromoacetate (40 mg, 0.26 mmol) and potassium carbonate (45 mg, 0.33 mmol) were added to 5 mL of acetonitrile, then the reaction solution was heated up to 50° C. and stirred for 16 h. The reaction solution was concentrated under reduced pressure. 50 mL of water were added, and the reaction solution was extracted with ethyl acetate (50 mL×3). The organic phases were combined, dried over anhydrous sodium sulfate, filtered, and the filtrate was concentrated under reduced pressure to obtain the title product methyl 2-(3-((4-(((tert-butoxycarbonyl)(methyl)amino)methyl)-2-(2-fluorophenyl)-1H-pyrrol-1-yl)sulfonyl)phenoxy)acetate 1i (110 mg, a yellow oil), which was used directly in the next step.

Step 8 tert-Butyl ((5-(2-fluorophenyl)-1-((3-(2-(methylamino)-2-oxoethoxy)phenyl)sulfonyl)-1H-pyrrol-3-yl)methyl)(methyl)carbamate Methyl 2-(3-((4-(((tert-butoxycarbonyl)(methyl)amino)methyl)-2-(2-fluorophenyl)-1H-pyrrol-1-yl)sulfonyl)phenoxy)acetate 1i (110 mg, 0.20 mmol) was dissolved in 10 mL of a solution of methylamine in methanol (33%), and the reaction solution was heated up to 40° C. and stirred for 2 h. The reaction solution was concentrated under reduced pressure to obtain the title product tert-butyl ((5-(2-fluorophenyl)-1-((3-(2-(methylamino)-2-oxoethoxy)phenyl)sulfonyl)-1H-pyrrol-3-yl)methyl)(methyl)carbamate 1j (60 mg, a yellow oil), which was used directly in the next step.

Step 9

2-(3-((2-(2-Fluorophenyl)-4-((methylamino)methyl)-1H-pyrrol-1-yl)sulfonyl)phenoxy)-N-methylacetamide tert-Butyl ((5-(2-fluorophenyl)-1-((3-(2-(methylamino)-2-oxoethoxy)phenyl)sulfonyl)-1H-pyrrol-3-yl)methyl)(methyl)carbamate 1j (60 mg, 0.11 mmol) was dissolved in 8 mL of dichloromethane, followed by addition of 2 mL of trifluoracetic acid, and then the reaction solution was stirred for 1 h. 20 mL of saturated sodium bicarbonate solution was added, and the reaction solution was extracted with dichloromethane (30 mL×2). The organic phases were combined, dried over anhydrous sodium sulfate, filtered, and the filtrate was concentrated under reduced pressure. The resulting residue was purified by silica gel column chromatography with elution system A to obtain the title product 2-(3-((2-(2-fluorophenyl)-4-((methylamino)methyl)-1H-pyrrol-1-yl)sulfonyl)phenoxy)-N-methylacetamide 1 (15 mg, a yellow oil), and the yield of the three steps was 16%.

MS m/z (ESI): 432.4 [M+1]

$^1$H NMR (400 MHz, CD$_3$OD) δ 7.60-7.61 (m, 1H), 7.35-7.43 (m, 2H), 7.22-7.24 (m, 1H), 7.02-7.13 (m, 4H), 6.93-6.94 (m, 1H), 6.32 (s, 1H), 4.41 (s, 2H), 3.56 (s, 1H), 3.87 (s, 2H), 2.76 (s, 3H), 2.54 (s, 3H)

Example 2

2-(3-((2-(2-Fluorophenyl)-4-((methylamino)methyl)-1H-pyrrol-1-yl)sulfonyl)phenoxy)acetamide

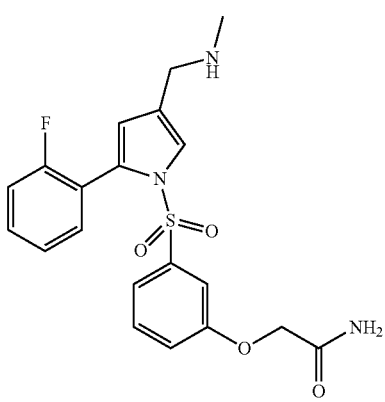

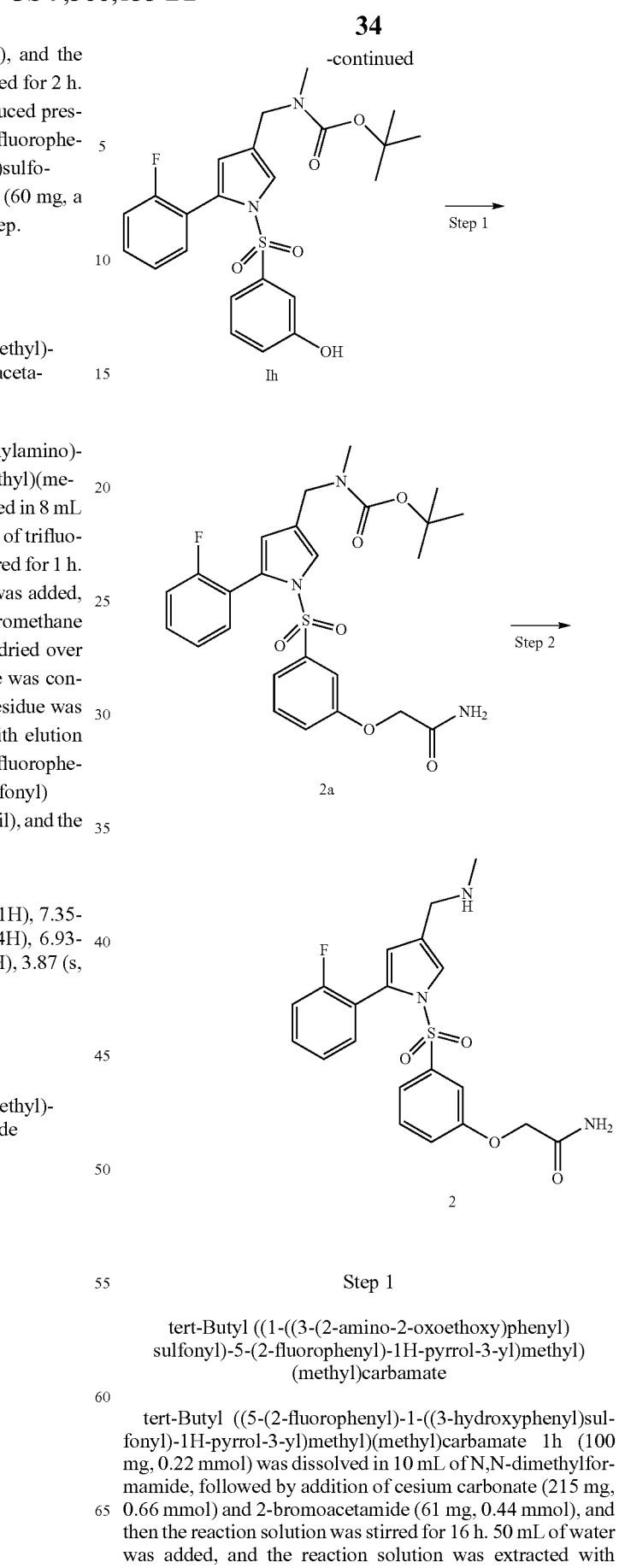

Step 1 tert-Butyl ((1-((3-(2-amino-2-oxoethoxy)phenyl)sulfonyl)-5-(2-fluorophenyl)-1H-pyrrol-3-yl)methyl)(methyl)carbamate tert-Butyl ((5-(2-fluorophenyl)-1-((3-hydroxyphenyl)sulfonyl)-1H-pyrrol-3-yl)methyl)(methyl)carbamate 1h (100 mg, 0.22 mmol) was dissolved in 10 mL of N,N-dimethylformamide, followed by addition of cesium carbonate (215 mg, 0.66 mmol) and 2-bromoacetamide (61 mg, 0.44 mmol), and then the reaction solution was stirred for 16 h. 50 mL of water was added, and the reaction solution was extracted with dichloromethane (50 mL×3). The organic phases were combined, dried over anhydrous sodium sulfate, filtered, and the filtrate was concentrated under reduced pressure. The resulting residue was purified by silica gel column chromatography with elution system B to obtain the title product tert-butyl ((1-((3-(2-amino-2-oxoethoxy)phenyl)sulfonyl)-5-(2-fluorophenyl)-1H-pyrrol-3-yl)methyl)(methyl)carbamate 2a (100 mg, a yellow oil) in 90% yield.

MS m/z (ESI): 462.2 [M+1]

Step 2

2-(3-((2-(2-Fluorophenyl)-4-((methylamino)methyl)-1H-pyrrol-1-yl)sulfonyl)phenoxy)acetamide tert-Butyl ((1-((3-(2-amino-2-oxoethoxy)phenyl)sulfonyl)-5-(2-fluorophenyl)-1H-pyrrol-3-yl)methyl)(methyl) carbamate 2a (100 mg, 0.19 mmol) was dissolved in 20 mL of dichloromethane. The reaction solution was cooled in an ice bath, 5 mL of trifluoroacetic acid were dropwise added, and then the reaction solution was stirred for 2 h. 50 mL of saturated sodium bicarbonate solution were added, and the reaction solution was extracted with dichloromethane (50 mL×3). The organic phases were combined, dried over anhydrous sodium sulfate, filtered, and the filtrate was concentrated under reduced pressure. The resulting residue was purified by silica gel column chromatography with elution system A to obtain the title product 2-(3-((2-(2-fluorophenyl)-4-((methylamino)methyl)-1H-pyrrol-1-yl)sulfonyl)phenoxy) acetamide 2 (60 mg, a yellow oil) in 75% yield.

MS m/z (ESI): 418.2 [M+1]
$^1$H NMR (400 MHz, CDCl$_3$) δ 7.31-7.33 (m, 3H), 7.10-7.13 (m, 2H), 7.03-7.09 (m, 3H), 6.89 (s, 1H), 6.52 (br, 1H), 6.19 (s, 1H), 5.84 (br, 1H), 4.40 (s, 2H), 4.24 (s, 2H), 2.83 (s, 3H)

Example 3

N-Cyclopropyl-2-(3-((2-(2-fluorophenyl)-4-((methylamino)methyl)-1H-pyrrol-1-yl)sulfonyl)phenoxy) acetamide

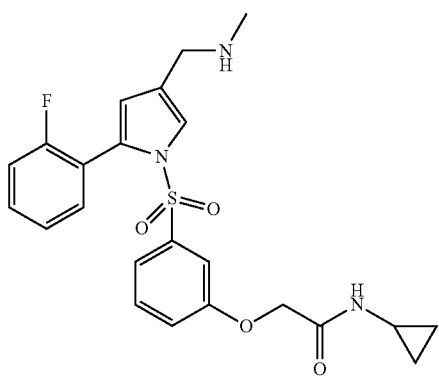

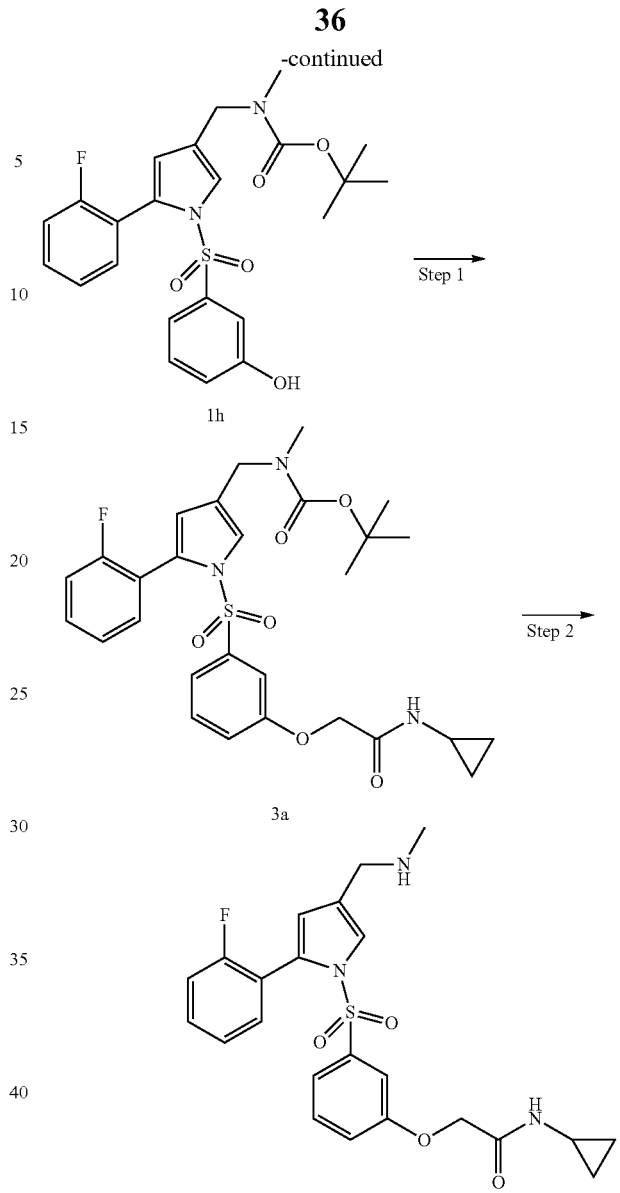

Step 1 tert-Butyl ((1-((3-(2-cyclopropylamino)-2-oxoethoxy)phenyl)sulfonyl)-5-(2-fluorophenyl)-1H-pyrrol-3-yl)methyl)(methyl)carbamate tert-Butyl ((5-(2-fluorophenyl)-1-((3-hydroxyphenyl)sulfonyl)-1H-pyrrol-3-yl)methyl)(methyl)carbamate 1h (100 mg, 0.22 mmol) was dissolved in 20 mL of N,N-dimethylformamide, followed by addition of cesium carbonate (215 mg, 0.66 mmol) and 2-bromo-N-cyclopropyl-acetamide (61 mg, 0.34 mmol, prepared by a known method disclosed in "*Journal of Medicinal Chemistry,* 1987, 30(1), 20-24") and then the reaction solution was stirred for 16 h. 50 mL of water were added, and the reaction solution was extracted with dichloromethane (50 mL×3). The organic phases were combined, dried over anhydrous sodium sulfate, filtered, and the filtrate was concentrated under reduced pressure to obtain the title product tert-butyl ((1-((3-(2-cyclopropylamino)-2-oxoethoxy)phenyl)sulfonyl)-5-(2-fluorophenyl)-1H-pyrrol-3-yl)

methyl)(methyl)carbamate 3a (100 mg, a yellow oil), which was used directly in the next step.

Step 2

N-Cyclopropyl-2-(3-((2-(2-fluorophenyl)-4-((methylamino)methyl)-1H-pyrrol-1-yl)sulfonyl)phenoxy)acetamide tert-Butyl ((1-((3-(2-(cyclopropylamino)-2-oxoethoxy)phenyl)sulfonyl)-5-(2-fluorophenyl)-1H-pyrrol-3-yl)methyl)(methyl)carbamate 3a (122 mg, 0.22 mmol) was dissolved in 8 mL of dichloromethane. The reaction solution was cooled in an ice bath, and 2 mL of trifluoroacetic acid were dropwise added. After removing the ice bath, the reaction solution was stirred at room temperature for 2 h. 20 mL of saturated sodium bicarbonate solution were added, and the reaction solution was extracted with dichloromethane (20 mL×3). The organic phases were combined, dried over anhydrous sodium sulfate, filtered, and the filtrate was concentrated under reduced pressure. The resulting residue was purified by silica gel column chromatography with elution system A to obtain the title product N-cyclopropyl-2-(3-((2-(2-fluorophenyl)-4-((methylamino)methyl)-1H-pyrrol-1-yl)sulfonyl)phenoxy)acetamide 3 (80 mg, a colorless oil) in 80% yield.

MS m/z (ESI): 458.2 [M+1]

$^1$H NMR (400 MHz, CD$_3$OD) δ 7.40-7.42 (m, 3H), 7.17 (m, 1H), 7.07-7.09 (m, 4H), 6.98-6.99 (m, 1H), 6.20 (s, 1H), 4.45 (s, 2H), 4.27 (s, 2H), 2.84 (s, 3H), 2.72-2.75 (m, 1H), 0.76-0.78 (m, 2H), 0.57-0.58 (m, 2H)

Example 4

2-(4-((2-(2-Fluorophenyl)-4-((methylamino)methyl)-1H-pyrrol-1-yl)sulfonyl)phenoxy)-N-methylacetamide

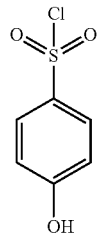

4a

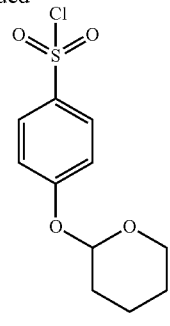

4b

-continued

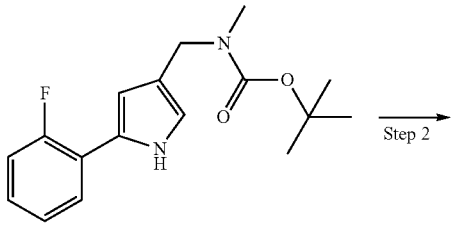

4b

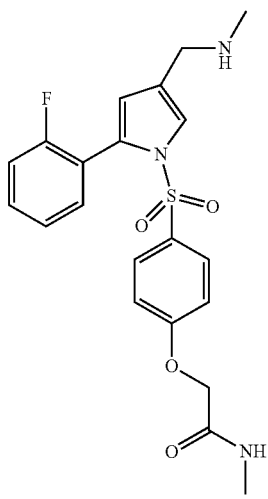

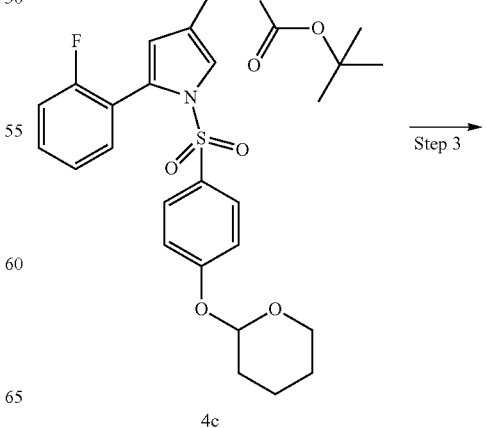

1f

4c

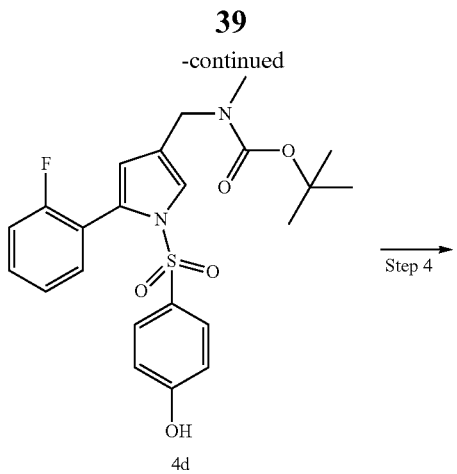

4d

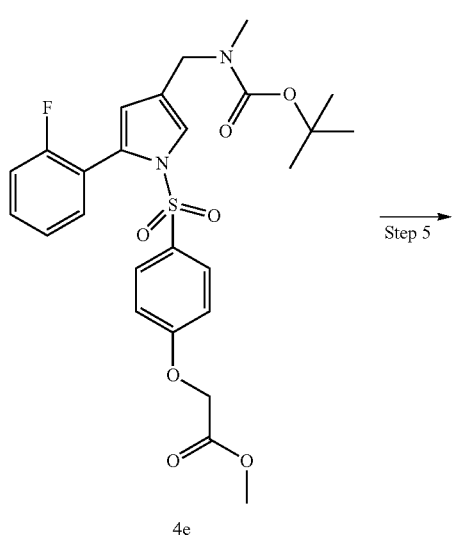

4e

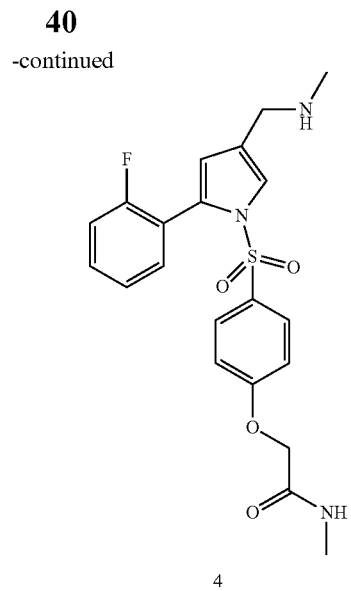

4

Step 1

4-((Tetrahydro-2H-pyran-2-yl)oxy)phenyl-1-sulfonyl chloride

4-Hydroxyphenyl-1-sulfonyl chloride 4a (4.0 g, 20.8 mmol, prepared by a known method disclosed in '*Przemysl Chemiczny*, 1980, 59(9), 495-498') was dissolved in 150 mL of dichloromethane, followed by addition of 3,4-dihydro-2H-pyrane (3.5 g, 41.5 mmol) and 4-methylbenzenesulfonic acid pyridine salt (400 mg, 1.6 mmol) and the reaction solution was stirred for 1 h. The reaction solution was concentrated under reduced pressure, and the resulting residue was purified by silica gel column chromatography with elution system B to obtain the title product 4-((tetrahydro-2H-pyran-2-yl)oxy) phenyl-1-sulfonyl chloride 4b (3.5 g, a colorless oil) in 60% yield.

Step 2 tert-Butyl ((5-(2-fluorophenyl)-1-((4-((tetrahydro-2H-pyran-2-yl)oxy)phenyl)sulfonyl)-1H-pyrrol-3-yl) methyl)(methyl)carbamate tert-Butyl ((5-(2-fluorophenyl)-1H-pyrrol-3-yl)methyl) (methyl)carbamate if (100 mg, 0.33 mmol) was dissolved in 3 mL of N,N-dimethylformamide. The reaction solution was cooled to 0° C. in an ice bath, and sodium hydride (66 mg, 60%) and 4-((tetrahydro-2H-pyran-2-yl)oxy)phenyl-1-sulfonyl chloride 4b (182 mg, 0.66 mmol) were added. After removing the ice bath, the reaction solution was stirred for 1 h. A saturated ammonium chloride solution was added to quench the reaction, and the reaction solution was extracted with dichloromethane (50 mL×3). The organic phases were combined, washed with saturated ammonium chloride solution, dried over anhydrous sodium sulfate, filtered, and the filtrate was concentrated under reduced pressure. The resulting residue was purified by silica gel column chromatography with elution system B to obtain the title product tert-butyl ((5-(2-fluorophenyl)-1-((4-((tetrahydro-2H-pyran-2-yl)oxy) phenyl)sulfonyl)-1H-pyrrol-3-yl)methyl)(methyl)carbamate 4c (115 mg, a colorless oil) in 65% yield.

MS m/z (ESI): 445.2 [M−99]

Step 3 tert-Butyl ((5-(2-fluorophenyl)-1-((4-hydroxyphenyl)sulfonyl)-1H-pyrrol-3-yl)methyl)(methyl)carbamate tert-Butyl ((5-(2-fluorophenyl)-1-((4-((tetrahydro-2H-pyran-2-yl)oxy)phenyl)sulfonyl)-1H-pyrrol-3-yl)methyl)(methyl)carbamate 4c (2.3 g, 4.28 mmol) was dissolved in 30 mL of methanol, followed by addition of p-toluenesulfonic acid (148 mg, 0.86 mmol), and then the reaction solution was stirred for 3 h. The reaction solution was concentrated under reduced pressure, and the resulting residue was purified by silica gel column chromatography with elution system B to obtain the title product tert-butyl ((5-(2-fluorophenyl)-1-((4-hydroxyphenyl)sulfonyl)-1H-pyrrol-3-yl)methyl)(methyl)carbamate 4d (2.0 g, a colorless oil) in 80% yield.

MS m/z (ESI): 405.1 [M−55]

Step 4

Methyl 2-(4-((4-(((tert-butoxycarbonyl)(methyl)amino)methyl)-2-(2-fluorophenyl)-1H-pyrrol-1-yl)sulfonyl)phenoxy)acetate tert-Butyl ((5-(2-fluorophenyl)-1-((4-hydroxyphenyl)sulfonyl)-1H-pyrrol-3-yl)methyl)(methyl)carbamate 4d (100 mg, 0.22 mmol) was dissolved in 3 mL of N,N-dimethylformamide, followed by addition of methyl bromoacetate (40 mg, 0.26 mmol) and potassium carbonate (45 mg, 0.33 mmol). The reaction solution was heated up to 60° C. and stirred for 16 h. The reaction solution was concentrated under reduced pressure, 50 mL of water were added, and the reaction solution was extracted with ethyl acetate (50 mL×3). The organic phases were combined, washed with saturated ammonium chloride solution, dried over anhydrous sodium sulfate, filtered, and the filtrate was concentrated under reduced pressure to obtain the title product methyl 2-(4-((4-(((tert-butoxycarbonyl)(methyl)amino)methyl)-2-(2-fluorophenyl)-1H-pyrrol-1-yl)sulfonyl)phenoxy)acetate 4e (100 mg, a yellow oil), which was used directly in the next step.

Step 5 tert-Butyl ((5-(2-fluorophenyl)-1-((4-(2-(methylamino)-2-oxoethoxy)phenyl)sulfonyl)-1H-pyrrol-3-yl)methyl)(methyl)carbamate Methyl 2-(4-((4-(((tert-butoxycarbonyl)(methyl)amino)methyl)-2-(2-fluorophenyl)-1H-pyrrol-1-yl)sulfonyl)phenoxy)acetate 4e (100 mg, 0.19 mmol) was dissolved in 5 mL of a solution of methylamine in methanol (33%), and the reaction solution was heated up to 40° C. and stirred for 2 h. The reaction solution was concentrated under reduced pressure to obtain the title product tert-butyl ((5-(2-fluorophenyl)-1-((4-(2-(methylamino)-2-oxoethoxy)phenyl)sulfonyl)-1H-pyrrol-3-yl)methyl)(methyl)carbamate 4f (100 mg, a yellow oil), which was used directly in the next step.

Step 6

2-(4-((2-(2-Fluorophenyl)-4-((methylamino)methyl)-1H-pyrrol-1-yl)sulfonyl)phenoxy)-N-methylacetamide tert-Butyl ((5-(2-fluorophenyl)-1-((4-(2-(methylamino)-2-oxoethoxy)phenyl)sulfonyl)-1H-pyrrol-3-yl)methyl)(methyl)carbamate 4f (100 mg, 0.19 mmol) was dissolved in 3 mL of dichloromethane, followed by addition of 1 mL of trifluoroacetic acid and then the reaction solution was stirred for 1 h. 10 mL of saturated sodium bicarbonate solution were added, and the reaction solution was extracted with dichloromethane (20 mL×2). The organic phases were combined, dried over anhydrous sodium sulfate, filtered, and the filtrate was concentrated under reduced pressure. The resulting residue was purified by silica gel column chromatography with elution system A to obtain the title product 2-(4-((2-(2-fluorophenyl)-4-((methylamino)methyl)-1H-pyrrol-1-yl)sulfonyl)phenoxy)-N-methylacetamide 4 (15 mg, a colorless oil), and the yield of the three steps was 16%.

MS m/z (ESI): 432.3 [M+1]

$^1$H NMR (400 MHz, CD$_3$OD) δ 7.60 (s, 1H), 7.38-7.46 (m, 3H), 7.00-7.17 (m, 5H), 6.32 (s, 1H), 4.57 (s, 2H), 3.86 (s, 2H), 2.81 (s, 3H), 2.55 (s, 3H)

Example 5

1-((3-((2-(2-Fluorophenyl)-4-((methylamino)methyl)-1H-pyrrol-1-yl)sulfonyl)phenoxy)methyl)-N-methylcyclopropylcarboxamide

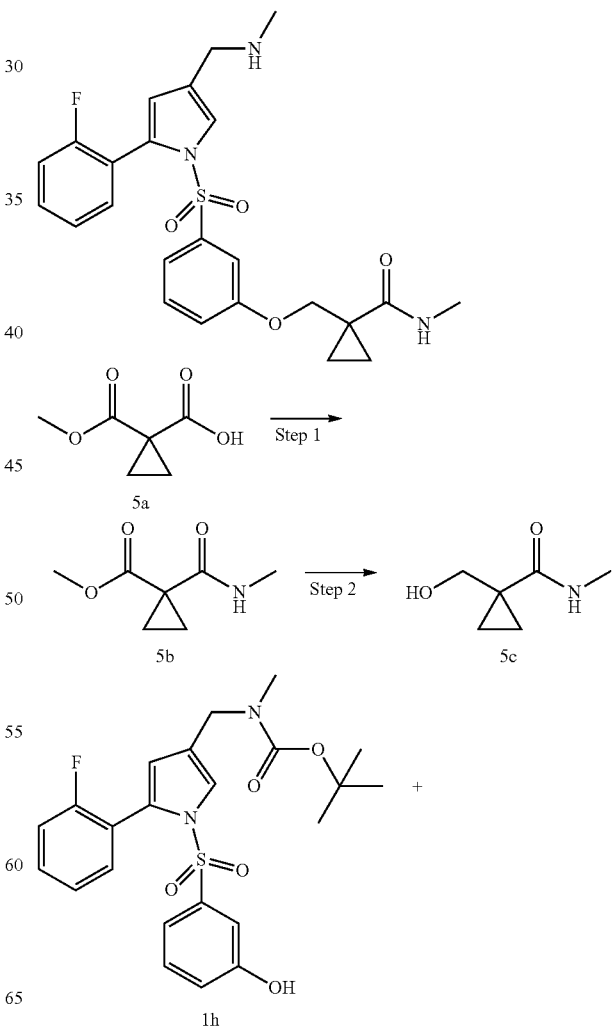

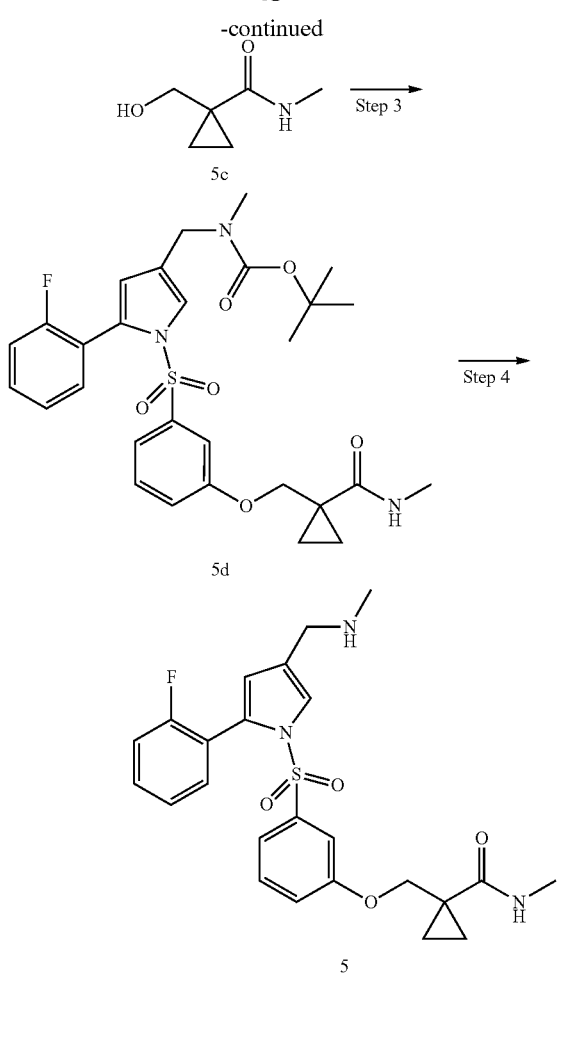

Step 1

Methyl 1-(methylcarbamoyl)cyclopropanecarboxylate 1-(Methoxycarbonyl)cyclopropanecarboxylic acid 5a (2.5 g, 13.9 mmol, prepared by a known method disclosed in "*Tetrahedron Letters,* 1987, 28 (36), 4225-4228") was dissolved in 20 mL of N,N-dimethylformamide, followed by addition of methylamine hydrochloride (1.4 g, 20.8 mmol), N,N-diisopropylethylamine (5.4 g, 41.7 mmol) and 2-(7-azabenzotriazol-1-yl)-N,N,N',N'-tetramethyluronium hexafluorophosphate (7.9 g, 20.8 mmol), and then the reaction solution was stirred for 3 h. 50 mL of saturated sodium bicarbonate solution were added, and the reaction solution was extracted with ethyl acetate (40 mL×3). The organic phases were combined, washed with saturated sodium bicarbonate solution, dried over anhydrous sodium sulfate, filtered, and the filtrate was concentrated under reduced pressure. The resulting residue was purified by silica gel column chromatography with elution system A to obtain the title product methyl 1-(methylcarbamoyl)cyclopropanecarboxylate 5b (700 mg, a colorless oil) in 32% yield.

Step 2

1-(Hydroxymethyl)-N-methyl cyclopropanecarboxamide

Methyl 1-(methylcarbamoyl)cyclopropanecarboxylate 5b (942 mg, 6 mmol) was dissolved in 10 mL of tetrahydrofuran in a dry ice-acetone bath, by addition of a solution of diisobutylaluminum hydride in tetrahydrofuran (1 M, 18 mL), then the reaction solution was stirred for 1 h, followed by addition of 3 mL of water. After removing the dry ice-acetone bath, the reaction solution was continuously stirred at room temperature for 1 h. The reaction solution was filtered, and the filtrate was concentrated under reduced pressure to obtain the title product 1-(hydroxymethyl)-N-methyl cyclopropanecarboxamide 5c (800 mg, a yellow solid), which was used directly in the next step.

Step 3 tert-Butyl ((5-(2-fluorophenyl)-1-((3-((1-(methylcarbamoyl)cyclopropyl)methoxy)phenyl)sulfonyl)-1H-pyrrol-3-yl)methyl)(methyl)carbamate tert-Butyl ((5-(2-fluorophenyl)-1-((3-hydroxyphenyl)sulfonyl)-1H-pyrrol-3-yl)methyl)(methyl)carbamate 1h (100 mg, 0.22 mmol), 1-(hydroxymethyl)-N-methyl cyclopropanecarboxamide 5c (47 mg, 0.33 mmol), diisopropyl azodicarboxylate (150 mg, 0.65 mmol) and triphenylphosphine (171 mg, 0.65 mmol) were added to 3 mL of dichloromethane, and then the reaction solution was stirred for 16 h. The reaction solution was concentrated under reduced pressure, and the resulting residue was purified by thin layer chromatography with elution system B to obtain the title compound tert-butyl ((5-(2-fluorophenyl)-1-((3-((1-(methylcarbamoyl)cyclopropyl)methoxy)phenyl)sulfonyl)-1H-pyrrol-3-yl)methyl)(methyl)carbamate 5d (100 mg, a yellow oil) in 81% yield.

MS m/z (ESI): 472.3 [M−99]

Step 4

1-((3-((2-(2-Fluorophenyl)-4-((methylamino)methyl)-1H-pyrrol-1-yl)sulfonyl)phenoxy)methyl)-N-methylcyclopropylcarboxamide tert-Butyl ((5-(2-fluorophenyl)-1-((3-((1-(methylcarbamoyl)cyclopropyl)methoxy)phenyl)sulfonyl)-1H-pyrrol-3-yl)methyl)(methyl)carbamate 5d (100 mg, 0.18 mmol) was dissolved in 3 mL of dichloromethane, followed by addition of 1 mL of trifluoroacetic acid, and then the reaction solution was stirred for 1 h. 10 mL of saturated sodium bicarbonate solution were added, and the reaction solution was extracted with dichloromethane (20 mL×2). The organic phases were combined, dried over anhydrous sodium sulfate, filtered, and the filtrate was concentrated under reduced pressure. The resulting residue was purified by thin layer chromatography with elution system A to obtain the title product 1-((3-((2-(2-fluorophenyl)-4-((methylamino)methyl)-1H-pyrrol-1-yl)sulfonyl)phenoxy)methyl)-N-methylcyclopropylcarboxamide (20 mg, a yellow oil) in 24% yield.

MS m/z (ESI): 472.2 [M+1]

$^1$H NMR (400 MHz, CD$_3$OD) δ 7.57 (s, 1H), 7.42-7.47 (m, 1H), 7.34-7.38 (dd, 1H), 7.05-7.21 (m, 5H), 6.91 (s, 1H), 6.31-6.33 (m, 1H), 4.02 (s, 2H), 3.78 (s, 2H), 2.75 (s, 3H), 2.49 (m, 3H), 1.21-1.25 (m, 2H), 0.88-0.90 (m, 2H)

Example 6

1-((4-((2-(2-Fluorophenyl)-4-((methylamino)methyl)-1H-pyrrol-1-yl)sulfonyl)phenoxy)methyl)-N-methylcyclopropylcarboxamide

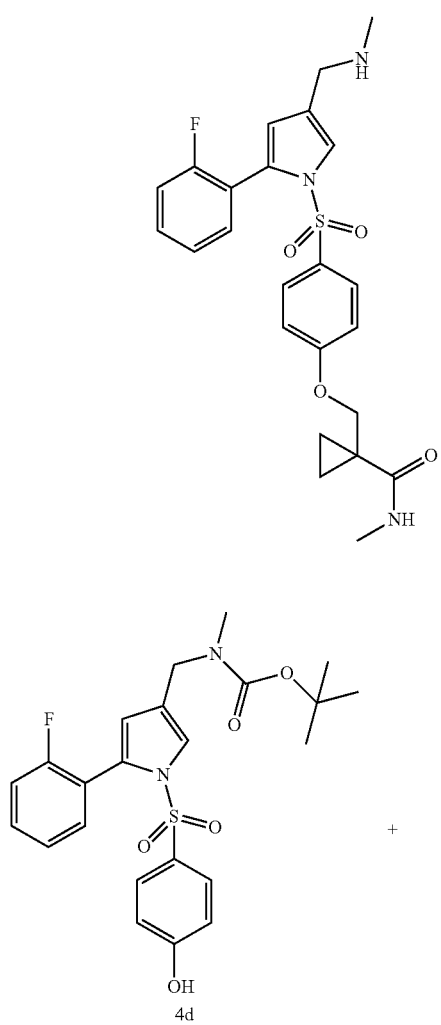

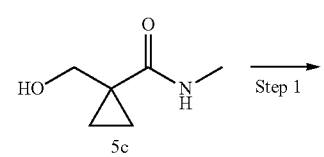

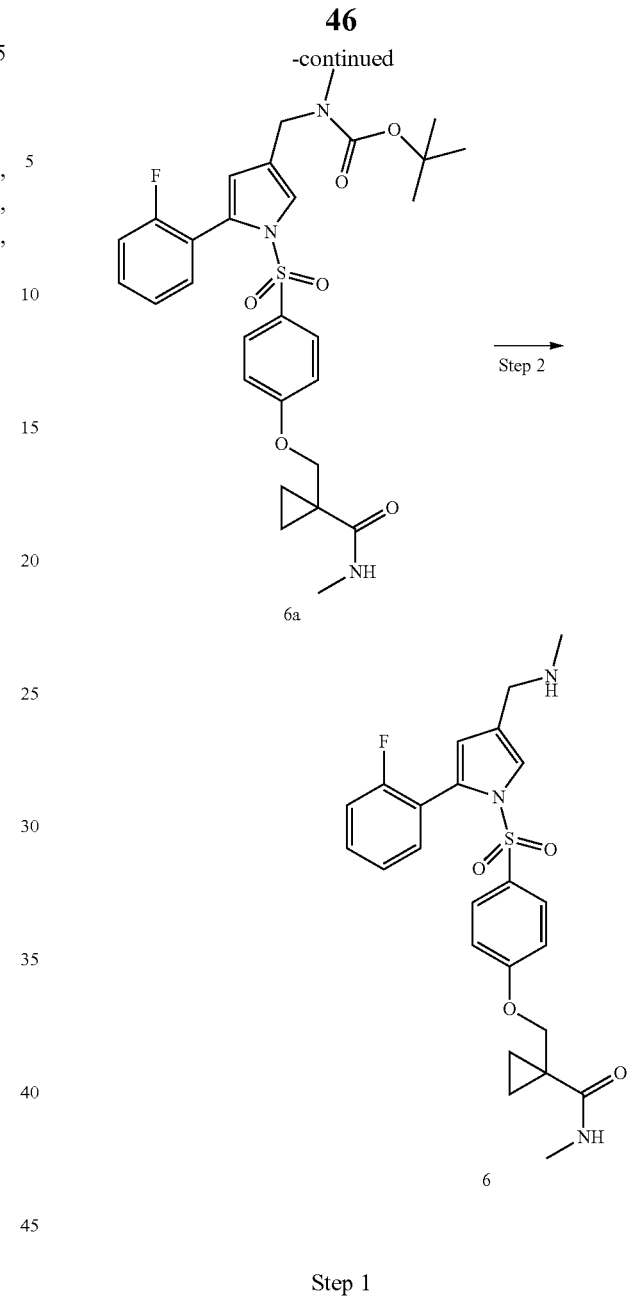

Step 1 tert-Butyl ((5-(2-fluorophenyl)-1-((4-((1-(methylcarbamoyl)cyclopropyl)methoxy)phenyl)sulfonyl)-1H-pyrrol-3-yl)methyl)(methyl)carbamate tert-Butyl ((5-(2-fluorophenyl)-1-((4-hydroxyphenyl)sulfonyl)-1H-pyrrol-3-yl)methyl)(methyl)carbamate 4d (100 mg, 0.22 mmol), 1-(hydroxymethyl)-N-methyl cyclopropanecarboxamide 5c (47 mg, 0.33 mmol), diisopropyl azodicarboxylate (150 mg, 0.65 mmol) and triphenylphosphine (171 mg, 0.65 mmol) were added to 3 mL of dichloromethane and then the reaction solution was stirred for 16 h. The reaction solution was concentrated under reduced pressure, and the resulting residue was purified by thin layer chromatography with elution system B to obtain the title product tert-butyl ((5-(2-fluorophenyl)-1-((4-((1-(methylcarbamoyl)cyclopropyl)methoxy)phenyl)sulfonyl)-1H-pyrrol-3-yl)methyl)(methyl)carbamate 6a (100 mg, a yellow oil) in 81% yield.

MS m/z (ESI): 472.2 [M-99]

Step 2

1-((4-((2-(2-Fluorophenyl)-4-((methylamino)methyl)-1H-pyrrol-1-yl)sulfonyl)phenoxy)methyl)-N-methylcyclopropylcarboxamide tert-Butyl ((5-(2-fluorophenyl)-1-((4-((1-(methylcarbamoyl)cyclopropyl)methoxy)phenyl)sulfonyl)-1H-pyrrol-3-yl)methyl)(methyl)carbamate 6a (100 mg, 0.18 mmol) was dissolved in 3 mL of dichloromethane, followed by addition of 1 mL of trifluoracetic acid and then the reaction solution was stirred for 1 h. 10 mL of saturated sodium bicarbonate solution were added, and the reaction solution was extracted with dichloromethane (20 mL×2). The organic phases were combined, dried over anhydrous sodium sulfate, filtered, and the filtrate was concentrated under reduced pressure. The resulting residue was purified by thin layer chromatography with elution system A to obtain the title product 1-((4-((2-(2-fluorophenyl)-4-((methylamino)methyl)-1H-pyrrol-1-yl)sulfonyl)phenoxy)methyl)-N-methylcyclopropylcarboxamide 6 (30 mg, a yellow oil) in 37% yield.

MS m/z (ESI): 472.3 [M+1]

$^1$H NMR (400 MHz, CD$_3$OD) δ 7.58 (s, 1H), 7.39-7.44 (m, 1H), 7.31-7.35 (m, 2H), 7.10-7.14 (dd, 1H), 7.02-7.06 (m, 2H), 6.90-6.92 (m, 2H), 6.29-6.31 (m, 1H), 4.11 (s, 2H), 3.87 (s, 2H), 2.69 (s, 3H), 2.55 (m, 3H), 1.17-1.20 (m, 2H), 0.85-0.88 (m, 2H)

Example 7

2-(3-((2-(Cyclohex-1-en-1-yl)-4-((methylamino)methyl)-1H-pyrrol-1-yl)sulfonyl)phenoxy)-N-cyclopropylacetamide

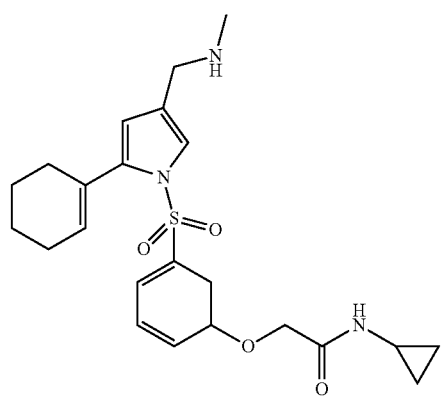

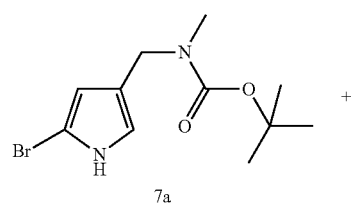
7a

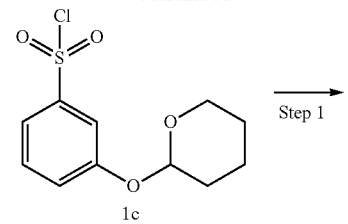
1c

Step 1

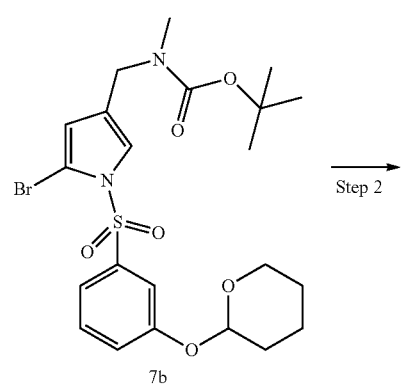
7b

Step 2

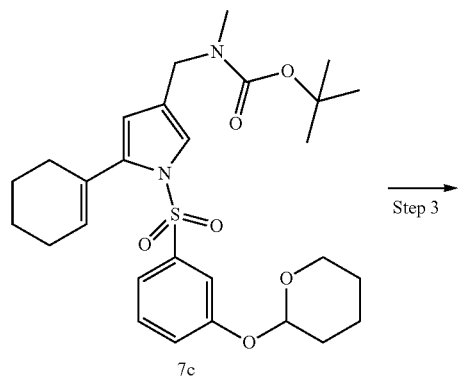
7c

Step 3

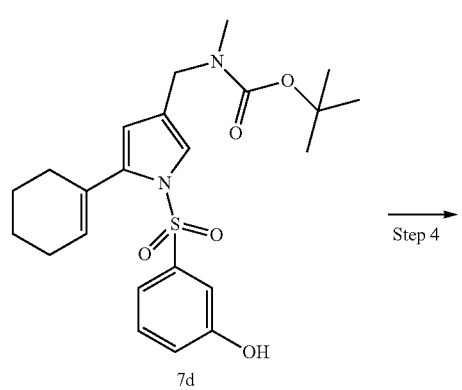
7d

Step 4

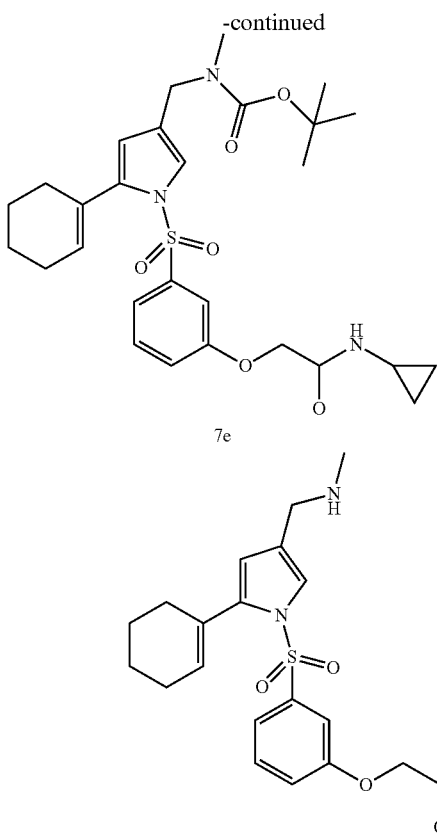

Step 1 tert-Butyl ((5-bromo-1-((3-((tetrahydro-2H-pyran-2-yl)oxy)phenyl)sulfonyl)-1H-pyrrol-3-yl)methyl)(methyl)carbamate tert-Butyl ((5-bromo-1H-pyrrol-3-yl)methyl)(methyl)carbamate 7a (632 mg, 2.2 mmol, prepared by a known method disclosed in "International Patent Application Publication WO2007026916") was dissolved in 25 mL of N,N-dimethylformamide, and then the reaction solution was cooled to 0° C. in an ice bath, followed by addition of sodium hydride (218 mg, 60%). The reaction solution was stirred for 1 h, followed by addition of 3-((tetrahydro-2H-pyran-2-yl)oxy)phenyl-1-sulfonyl chloride 1c (500 mg, 1.8 mmol) and was continuously stirred for 20 min. After removing the ice bath, a saturated ammonium chloride solution was added to quench the reaction, and the reaction solution was extracted with ethyl acetate (50 mL×4). The organic phases were combined, washed with saturated sodium chloride solution, dried over anhydrous sodium sulfate, filtered, and the filtrate was concentrated under reduced pressure. The resulting residue was purified by silica gel column chromatography with elution system C to obtain the title product tert-butyl ((5-bromo-1-((3-((tetrahydro-2H-pyran-2-yl)oxy)phenyl)sulfonyl)-1H-pyrrol-3-yl)methyl)(methyl)carbamate 7b (770 mg, a colorless oil) in 80% yield.

MS m/z (ESI): 388.0 [M−141]

Step 2 tert-Butyl ((5-(cyclohex-1-en-1-yl)-1-((3-((tetrahydro-2H-pyran-2-yl)oxy)phenyl)sulfonyl)-1H-pyrrol-3-yl)methyl)(methyl)carbamate tert-Butyl ((5-bromo-1-((3-((tetrahydro-2H-pyran-2-yl)oxy)phenyl)sulfonyl)-1H-pyrrol-3-yl)methyl)(methyl)carbamate 7b (770 mg, 1.5 mmol), 2-(cyclohex-1-en-1-yl)-4,4,5,5-tetramethyl-1,3,2-dioxaborolane (394 mg, 1.4 mmol, prepared by a known method disclosed in "*Journal of the American Chemical Society*, 2002, 124(27), 8001-8006"), [1,1'-bis(diphenylphosphino)ferrocene]dichloropalladium (53 mg, 0.07 mmol) and potassium carbonate (401 mg, 2.9 mmol) were successively added to 15 mL of a mixed solvent of ethylene glycol dimethyl ether and water (V/V=3:1), then the reaction solution was heated up to 100° C. and stirred for 10 h. 15 mL of water were added, and the reaction solution was extracted with ethyl acetate (50 mL×4). The organic phases were combined, dried over anhydrous sodium sulfate, filtered, and the filtrate was concentrated under reduced pressure. The resulting residue was purified by silica gel column chromatography with elution system C to obtain the title product tert-butyl ((5-(cyclohex-1-en-1-yl)-1-((3-((tetrahydro-2H-pyran-2-yl)oxy)phenyl)sulfonyl)-1H-pyrrol-3-yl)methyl)(methyl)carbamate 7c (554 mg, a light yellow oil) in 72% yield.

MS m/z (ESI): 389.0 [M−141]

Step 3 tert-Butyl ((5-(cyclohex-1-en-1-yl)-1-((3-hydroxyphenyl)sulfonyl)-1H-pyrrol-3-yl)methyl)(methyl)carbamate tert-Butyl ((5-(cyclohex-1-en-1-yl)-1-((3-((tetrahydro-2H-pyran-2-yl)oxy)phenyl)sulfonyl)-1H-pyrrol-3-yl)methyl)(methyl)carbamate 7c (600 mg, 1.1 mmol) was dissolved in 50 mL of dichloromethane, followed by addition of p-toluenesulfonic acid (195 mg, 1.1 mmol), and then the reaction solution was stirred for 3 h. 50 mL of saturated ammonium chloride solution were added, the reaction solution was separated, and the water phase was extracted with dichloromethane (50 mL×3). The organic phases were combined, dried over anhydrous sodium sulfate, filtered, and the filtrate was concentrated under reduced pressure. The resulting residue was purified by silica gel column chromatography with elution system C to obtain the title product tert-butyl ((5-(cyclohex-1-en-1-yl)-1-((3-hydroxyphenyl)sulfonyl)-1H-pyrrol-3-yl)methyl)(methyl)carbamate 7d (384 mg, a colorless oil) in 76% yield.

MS m/z (ESI): 389.0 [M−140]

Step 4 tert-Butyl ((5-(cyclohex-1-en-1-yl)-1-((3-(2-(cyclopropylamino)-2-oxoethoxy)phenyl)sulfonyl)-1H-pyrrol-3-yl)methyl)(methyl)carbamate tert-Butyl ((5-(cyclo ex-1-en-1-yl)-1-((3-hydroxyphenyl)sulfonyl)-1H-pyrrol-3-yl)methyl)(methyl)carbamate 7d (100 mg, 0.22 mmol) was dissolved in 20 mL of N,N-dimethylformamide, followed by addition of cesium carbonate (146 mg, 0.45 mmol) and 2-bromo-N-cyclopropyl-acetamide (79 mg, 0.45 mmol, prepared by a known method disclosed in "*Journal of Medicinal Chemistry*, 1987, 30(1), 20-24"), and then the reaction solution was stirred for 16 h. The reaction solution was concentrated under reduced pressure, and the resulting residue was purified by thin layer chromatography with elution system C to obtain the title product tert-butyl ((5-(cyclohex-1-en-1-yl)-1-((3-(2-(cyclopropylamino)-2-oxoethoxy)phenyl)sulfonyl)-1H-pyrrol-3-yl)methyl)(methyl)carbamate 7e (117 mg, a light yellow oily product) in 98% yield.

MS m/z (ESI): 486.3 [M−55]

Step 5

2-(3-((2-(Cyclohex-1-en-1-yl)-4-((methylamino)methyl)-1H-pyrrol-1-yl)sulfonyl)phenoxy)-N-cyclopropylacetamide tert-Butyl ((5-(cyclohex-1-en-1-yl)-1-((3-(2-(cyclopropylamino)-2-oxoethoxy)phenyl)sulfonyl)-1H-pyrrol-3-yl)methyl)(methyl)carbamate 7e (97 mg, 0.22 mmol) was dissolved in 8 mL of dichloromethane, and the reaction solution was cooled in an ice bath, followed by dropwise addition of 2 mL of trifluoroacetic acid. After removing the ice bath, the reaction solution was stirred at room temperature for 2 h. A saturated sodium bicarbonate solution was added dropwise until the pH of the reaction solution was 7 to 8, and then it was extracted with dichloromethane (20 mL×3). The organic phases were combined, dried over anhydrous sodium sulfate, filtered, and the filtrate was concentrated under reduced pressure. The resulting residue was purified by thin layer chromatography with elution system A to obtain the title product 2-(3-((2-(cyclohex-1-en-1-yl)-4-((methylamino)methyl)-1H-pyrrol-1-yl)sulfonyl)phenoxy)-N-cyclopropylacetamide 7 (67 mg, a light yellow oil) in 85% yield.

MS m/z (ESI): 444.4 [M+1]

$^1$H NMR (400 MHz, CD$_3$OD) δ 7.46 (t, 1H), 7.36 (d, 1H), 7.28 (s, 1H), 7.26 (s, 1H), 7.25 (d, 1H), 4.51 (s, 2H), 3.58 (s, 2H), 2.72 (m, 2H), 2.38 (s, 3H), 2.08 (m, 4H), 1.64 (m, 4H), 0.74 (m, 2H), 0.74 (m, 2H)

Example 8

2-(3-((2-(Cyclohex-1-en-1-yl)-4-((methylamino)methyl)-1H-pyrrol-1-yl)sulfonyl)phenoxy)-N,N-dimethylacetamide

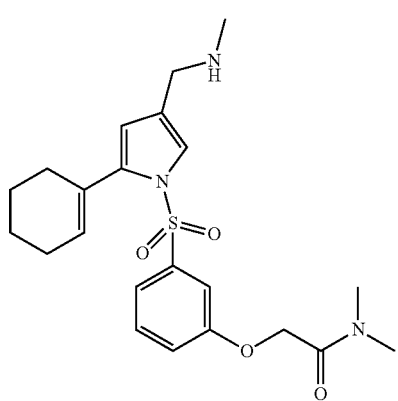

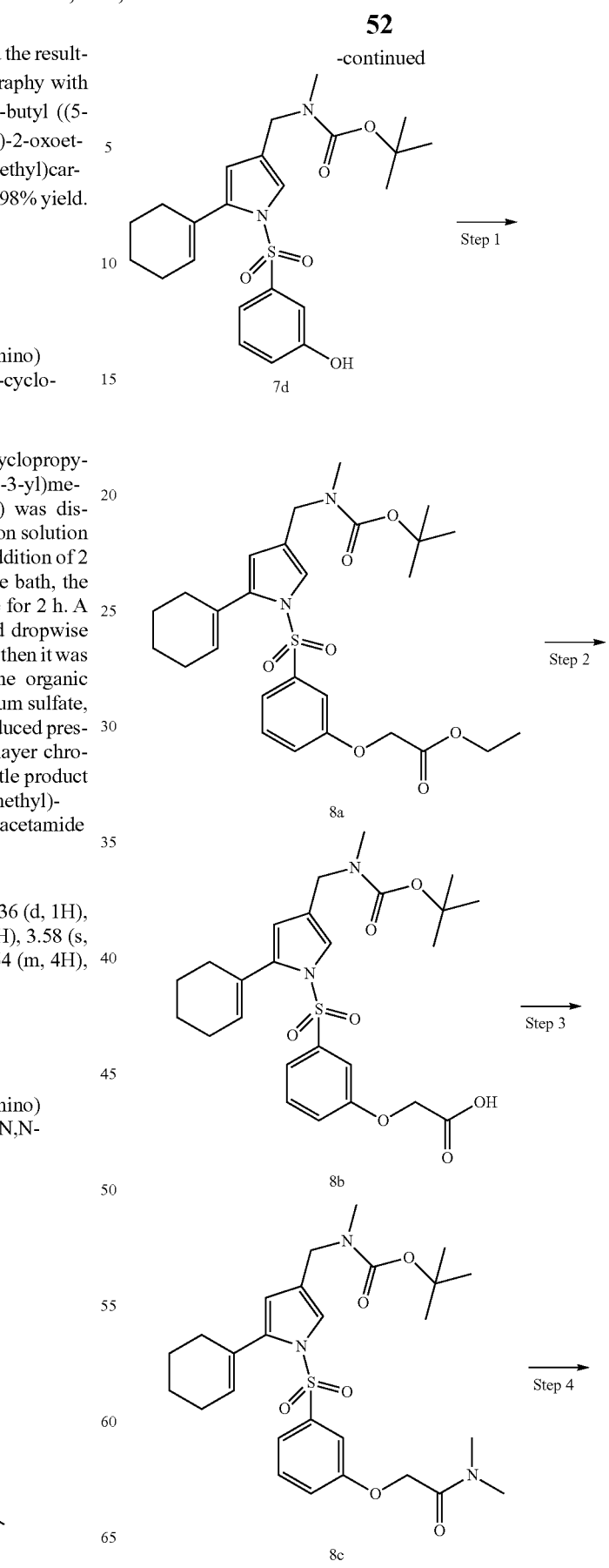

-continued

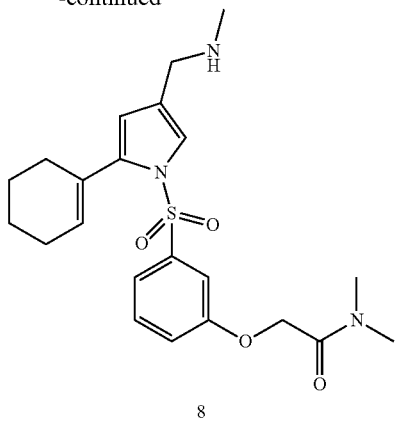

8

Step 1

Ethyl 2-(3-((4-(((tert-Butoxycarbonyl)(methyl)amino)methyl)-2-(cyclohex-1-en-1-yl)-1H-pyrrol-1-yl)sulfonyl)phenoxy)acetate tert-Butyl ((5-(cyclohex-1-en-1-yl)-1-((3-hydroxyphenyl)sulfonyl)-1H-pyrrol-3-yl)methyl)(methyl)carbamate 7d (100 mg, 0.22 mmol) was dissolved in 20 mL of N,N-dimethylformamide, followed by addition of cesium carbonate (146 mg, 0.45 mmol) and ethyl bromoacetate (102 mg, 0.67 mmol), and then the reaction solution was stirred for 3 h. The reaction solution was concentrated under reduced pressure, 50 mL of water was added, and the reaction solution was extracted with ethyl acetate (50 mL×3). The organic phases were combined, dried over anhydrous sodium sulfate, filtered, and the filtrate was concentrated under reduced pressure to obtain the title product ethyl 2-(3-((4-(((tert-butoxycarbonyl)(methyl)amino)methyl)-2-(cyclohex-1-en-1-yl)-1H-pyrrol-1-yl)sulfonyl)phenoxy)acetate 8a (99 mg, a light yellow oil) in 81% yield.

MS m/z (ESI): 477.2 [M−55]

Step 2

2-(3-((4-(((tert-Butoxycarbonyl)(methyl)amino)methyl)-2-(cyclohex-1-en-1-yl)-1H-pyrrol-1-yl)sulfonyl)phenoxy)acetic acid Ethyl 2-(3-((4-(((tert-butoxycarbonyl)(methyl)amino)methyl)-2-(cyclohex-1-en-1-yl)-1H-pyrrol-1-yl)sulfonyl)phenoxy)acetate 8a (97 mg, 0.18 mmol) and lithium hydroxide (100 mg, 4.2 mmol) were added to 25 mL of a mixed solvent of tetrahydrofuran and water (V:V=1:1), and then the reaction solution was stirred for 1 h. The reaction solution was extracted with dichloromethane (50 mL×3), and the organic phases were combined, washed with saturated sodium chloride solution, dried over anhydrous sodium sulfate, filtered, and the filtrate was concentrated under reduced pressure to obtain the title product 2-(3-((4-(((tert-butoxycarbonyl)(methyl)amino)methyl)-2-(cyclohex-1-en-1-yl)-1H-pyrrol-1-yl)sulfonyl)phenoxy)acetic acid 8b (69 mg, a colorless oil) in 75% yield.

MS m/z (ESI): 449.0 [M−55]

Step 3 tert-Butyl ((5-(cyclohex-1-en-1-yl)-1-((3-(2-(dimethylamino)-2-oxoethoxy)phenyl)sulfonyl)-1H-pyrrol-3-yl)methyl)(methyl)carbamate 2-(3-((4-(((tert-butoxycarbonyl)(methyl)amino)methyl)-2-(cyclohex-1-en-1-yl)-1H-pyrrol-1-yl)sulfonyl)phenoxy)acetic acid 8b (69 mg, 0.14 mmol) was dissolved in 15 mL of N,N-dimethylformamide, followed by addition of ethanolamine (16.7 mg, 0.27 mmol), 2-(7-azabenzotriazol-1-yl)-N,N,N',N'-tetramethyluronium hexafluorophosphate (104 mg, 0.27 mmol) and N,N-diisopropylethylamine (53 mg, 0.41 mmol), and then the reaction solution was stirred for 1 h. The reaction solution was concentrated under reduced pressure, and the resulting residue was purified by silica gel column chromatography with elution system C to obtain the title product tert-butyl ((5-(cyclohex-1-en-1-yl)-1-((3-(2-(dimethylamino)-2-oxoethoxy)phenyl)sulfonyl)-1H-pyrrol-3-yl)methyl)(methyl)carbamate 8c (55 mg, a colorless oily product) in 76% yield.

MS m/z (ESI): 476.3 [M−55]

Step 4

2-(3-((2-(Cyclohex-1-en-1-yl)-4-((methylamino)methyl)-1H-pyrrol-1-yl)sulfonyl)phenoxy)-N,N-dimethylacetamide tert-Butyl ((5-(cyclohex-1-en-1-yl)-1-((3-(2-(dimethylamino)-2-oxoethoxy)phenyl)sulfonyl)-1H-pyrrol-3-yl)methyl)(methyl)carbamate 8c (69 mg, 0.13 mmol) was dissolved in 8 mL of dichloromethane, and the reaction solution was cooled in an ice bath, followed by dropwise addition of 2 mL of trifluoroacetic acid. After removing the ice bath, the reaction solution was stirred at room temperature for 2 h. A saturated sodium bicarbonate solution was added dropwise until the pH of the reaction solution was 7 to 8, and then it was extracted with dichloromethane (20 mL×3). The organic phases were combined, dried over anhydrous sodium sulfate, filtered, and the filtrate was concentrated under reduced pressure. The resulting residue was purified by thin layer chromatography with elution system A to obtain the title product 2-(3-((2-(cyclohex-1-en-1-yl)-4-((methylamino)methyl)-1H-pyrrol-1-yl)sulfonyl)phenoxy)-N,N-dimethylacetamide 8 (39 mg, a colorless oil) in 69% yield.

MS m/z (ESI): 432.5 [M+1]

$^1$H NMR (400 MHz, CD$_3$OD) δ 7.44 (t, 1H), 7.34 (d, 1H), 7.28 (s, 1H), 7.25 (s, 1H), 7.23 (d, 1H), 6.02 (s, 1H), 5.40 (m, 1H), 3.59 (s, 2H), 3.07 (s, 3H), 2.96 (s, 3H), 2.38 (s, 3H), 2.09 (m, 4H), 1.68 (m, 4H)

55

Example 9

2-(3-((2-(2-Fluorophenyl)-4-((methylamino)methyl)-1H-pyrrol-1-yl)sulfonyl)phenoxy)-N,N-dimethylacetamide

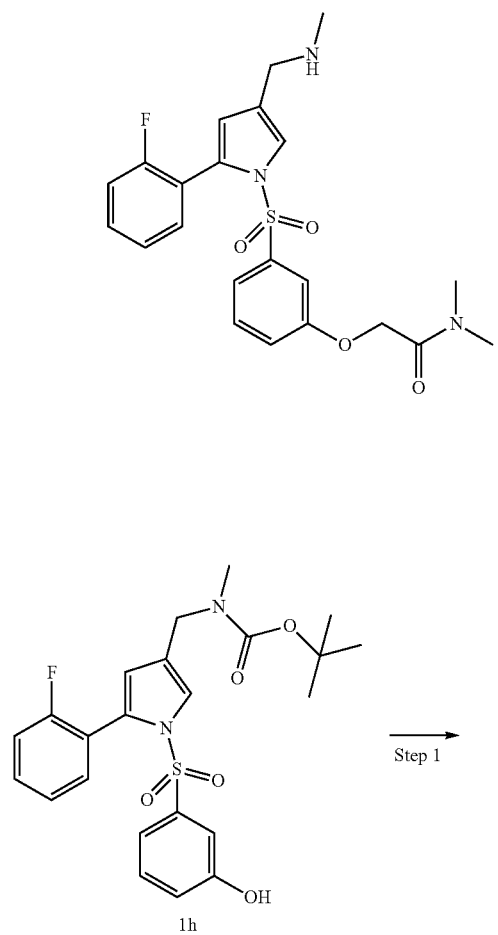

1h

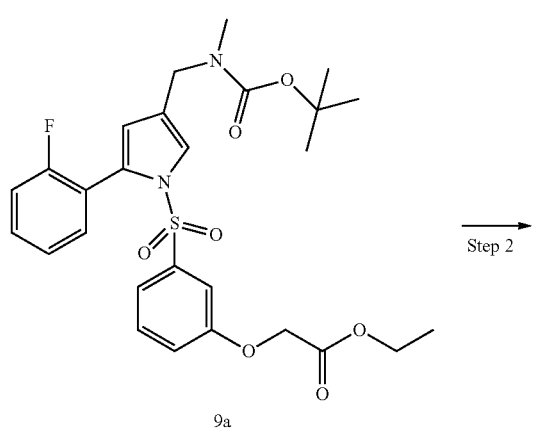

9a

56

-continued

9b

9c

9

Step 1

Ethyl 2-(3-((4-(((tert-butoxycarbonyl)(methyl)amino)methyl)-2-(2-fluorophenyl)-1H-pyrrol-1-yl)sulfonyl)phenoxy)acetate tert-Butyl ((5-(2-fluorophenyl)-1-((3-hydroxyphenyl)sulfonyl)-1H-pyrrol-3-yl)methyl)(methyl)carbamate 1h (100 mg, 0.22 mmol) was dissolved in 20 mL of N,N-dimethylformamide, followed by addition of cesium carbonate (146 mg, 0.45 mmol) and ethyl bromoacetate (102 mg, 0.67 mmol), and then the reaction solution was stirred for 3 h. The reaction solution was concentrated under reduced pressure, 50 mL of water were added, and the reaction solution was extracted with ethyl acetate (50 mL×3). The organic phases were combined, dried over anhydrous sodium sulfate, filtered, and the filtrate was concentrated under reduced pressure to obtain the title product ethyl 2-(3-((4-(((tert-butoxycarbonyl)(methyl) amino)methyl)-2-(2-fluorophenyl)-1H-pyrrol-1-yl)sulfonyl) phenoxy)acetate 9a (84 mg, a brown oil) in 70% yield.

MS m/z (ESI): 491.3 [M−55]

Step 2

2-(3-((4-(((tert-Butoxycarbonyl)(methyl)amino)me-thyl)-2-(2-fluorophenyl)-1H-pyrrol-1-yl)sulfonyl) phenoxy)acetic acid Ethyl 2-(3-((4-(((tert-butoxycarbonyl)(methyl)amino)me-thyl)-2-(2-fluorophenyl)-1H-pyrrol-1-yl)sulfonyl)phenoxy) acetate 9a (170 mg, 0.31 mmol) and lithium hydroxide (71 mg, 3.0 mmol) were added to 20 mL of a mixed solvent of tetrahydrofuran and water (V/V=1:1) and then the reaction solution was stirred for 3 h. 1M of hydrochloric acid was added dropwise until the pH of the reaction solution was 5, and then it was extracted with ethyl acetate (30 mL×2). The organic phases were combined, washed with saturated sodium chloride solution, dried over anhydrous sodium sulfate, filtered, and the filtrate was concentrated under reduced pressure to obtain the title product 2-(3-((4-(((tert-butoxycar-bonyl)(methyl)amino)methyl)-2-(2-fluorophenyl)-1H-pyr-rol-1-yl)sulfonyl)phenoxy)acetic acid 9b (160 mg, a yellow oil), which was used directly in the next step.

MS m/z (ESI): 517.1 [M−1]

Step 3 tert-Butyl ((1-((3-(2-(Dimethylamino)-2-oxoethoxy) phenyl)sulfonyl)-5-(2-fluorophenyl)-1H-pyrrol-3-yl) methyl)(methyl)carbamate 2-(3-((4-(((tert-Butoxycarbonyl)(methyl)amino)methyl)-2-(2-fluorophenyl)-1H-pyrrol-1-yl)sulfonyl)phenoxy)acetic acid 9b (170 mg, 0.33 mmol) was added to a solution of methylamine in tetrahydrofuran (2 N, 5 mL), followed by addition of 2-(7-azabenzotriazol-1-yl)-N,N,N',N'-tetram-ethyluronium hexafluorophosphate (104 mg, 0.91 mmol) and then the reaction solution was stirred for 3 h. 20 mL of water and 20 mL of ethyl acetate were added, and the reaction solution was layered, the water phase was extracted with ethyl acetate (20 mL×1). The organic phases were combined, washed with saturated sodium chloride solution, dried over anhydrous sodium sulfate, filtered, and the filtrate was concentrated under reduced pressure. The resulting residue was purified by thin layer chromatography with elution system C to obtain the title product tert-butyl ((1-((3-(2-(dimethy-lamino)-2-oxoethoxy)phenyl)sulfonyl)-5-(2-fluorophenyl)-1H-pyrrol-3-yl)methyl)(methyl)carbamate 9c (50 mg, a white solid) in 28% yield.

MS m/z (ESI): 446.3 [M−99]

Step 4

2-(3-((2-(2-Fluorophenyl)-4-((methylamino)methyl)-1H-pyrrol-1-yl)sulfonyl)phenoxy)-N,N-dimethylac-etamide tert-Butyl ((1-((3-(2-(dimethylamino)-2-oxoethoxy)phe-nyl)sulfonyl)-5-(2-fluorophenyl)-1H-pyrrol-3-yl)methyl) (methyl)carbamate 9c (54 mg, 0.10 mmol) was dissolved in 4 mL of dichloromethane, and the reaction solution was cooled in an ice bath, followed by dropwise addition of a solution of hydrogen chloride in 1,4-dioxane (4 N, 4 mL). After remov-ing the ice bath, the reaction solution was stirred at room temperature for 3h. A saturated sodium bicarbonate solution was added dropwise until the pH of the reaction solution was 7 to 8, 5 mL of water were added, and then the reaction solution was extracted with ethyl acetate (10 mL×3). The organic phases were combined, dried over anhydrous sodium sulfate, filtered, and the filtrate was concentrated under reduced pressure to obtain the title product 2-(3-((2-(2-fluo-rophenyl)-4-((methylamino)methyl)-1H-pyrrol-1-yl)sulfo-nyl)phenoxy)-N,N-dimethylacetamide 9 (20 mg, a yellow solid) in 45% yield.

MS m/z (ESI): 446.2 [M+1]

$^1$H NMR (400 MHz, DMSO-$d_6$) δ 2.43 (s, 3H), 2.83 (s, 3H), 2.97 (s, 3H), 3.87 (s, 2H), 4.86 (s, 2H), 6.34 (m, 1H), 6.87 (br, 1H), 6.97-7.14 (m, 2H), 7.24 (d, 2H), 7.21 (d, 1H), 7.44 (s, 2H), 7.69 (s, 1H)

Example 10

2-(3-((2-(2-Fluorophenyl)-4-((methylamino)methyl)-1H-pyrrol-1-yl)sulfonyl)phenoxy)-N-(2-hydroxy-ethyl)acetamide

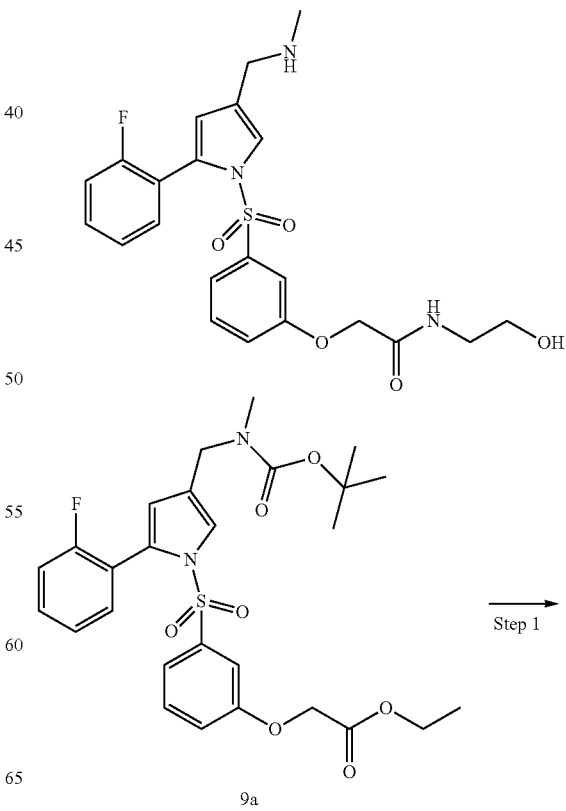

-continued

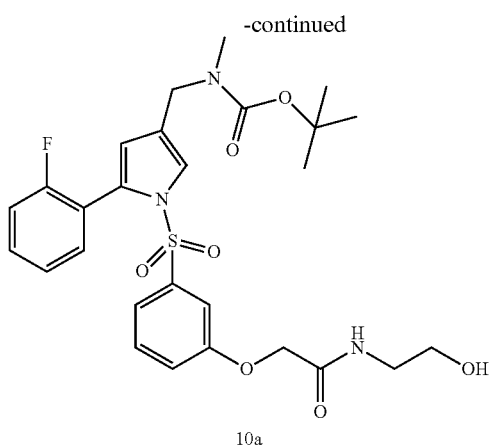

10a

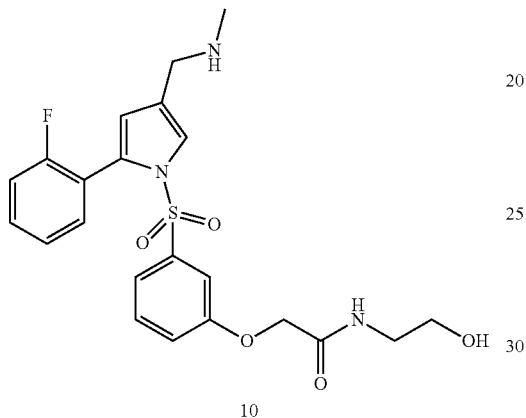

10

Step 1 tert-Butyl ((5-(2-fluorophenyl)-1-((3-(2-((2-hydroxyethyl)amino)-2-oxoethoxy)phenyl)sulfonyl)-1H-pyrrol-3-yl)methyl)(methyl)carbamate Ethyl 2-(3-((4-(((tert-butoxycarbonyl)(methyl)amino)methyl)-2-(2-fluorophenyl)-1H-pyrrol-1-yl)sulfonyl)phenoxy)acetate 9a (100 mg, 0.18 mmol) was dissolved in 10 mL of isopropanol, followed by addition of one drop of ethanolamine, and then the reaction solution was heated up to 50° C. and stirred for 24 h. The reaction solution was concentrated under reduced pressure, and the resulting residue was purified by thin layer chromatography with elution system C to obtain the title product tert-butyl ((5-(2-fluorophenyl)-1-((3-(2-((2-hydroxyethyl)amino)-2-oxoethoxy)phenyl)sulfonyl)-1H-pyrrol-3-yl)methyl)(methyl)carbamate 10a (85 mg, a yellow solid) in 84%. yield MS m/z (ESI): 462.3 [M−99]

Step 2

2-(3-((2-(2-Fluorophenyl)-4-((methylamino)methyl)-1H-pyrrol-1-yl)sulfonyl)phenoxy)-N-(2-hydroxyethyl)acetamide tert-Butyl ((5-(2-fluorophenyl)-1-((3-(2-((2-hydroxyethyl)amino)-2-oxoethoxy) phenyl)sulfonyl)-1H-pyrrol-3-yl)methyl)(methyl)carbamate 10a (83 mg, 0.15 mmol) was added to a solution of hydrogen chloride in 1,4-dioxane (4 N, 20 mL), and then the reaction solution was stirred for 2 h. The pH of the reaction solution was adjusted to 7 to 8 with a saturated sodium bicarbonate solution, and it was extracted with dichloromethane (50 mL×2). The organic phases were combined, dried over anhydrous sodium sulfate, filtered, and the filtrate was concentrated under reduced pressure. The resulting residue was purified by thin layer chromatography with elution system A to obtain the title product 2-(3-((2-(2-fluorophenyl)-4-((methylamino)methyl)-1H-pyrrol-1-yl)sulfonyl)phenoxy)-N-(2-hydroxyethyl)acetamide 10 (34 mg, a yellow oil) in 50% yield.

MS m/z (ESI): 462.3 [M+1]

$^1$H NMR (400 MHz, DMSO-$d_6$) δ 2.43 (s, 3H), 3.06-3.31 (m, 3H), 3.42 (t, 2H), 3.86 (br, 2H), 4.49 (br, 2H), 6.38 (m, 1H), 6.94-7.13 (m, 3H), 7.13-7.37 (m, 3H), 7.39-7.60 (m, 2H), 7.67 (br, 1H), 8.18 (br, 1H)

Example 11

2-(3-((2-(2-Fluorophenyl)-4-((methylamino)methyl)-1H-pyrrol-1-yl)sulfonyl)phenoxy)-N-(3-hydroxyphenyl)acetamide

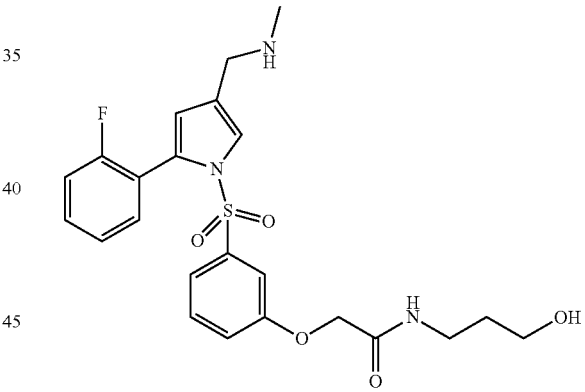

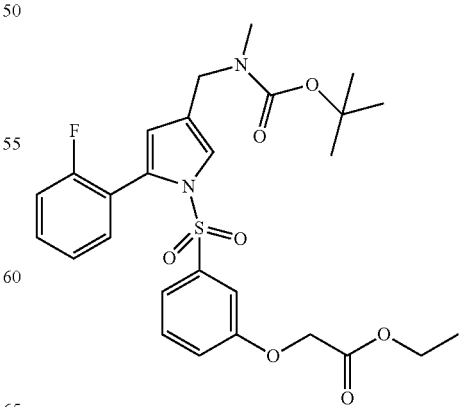

9a

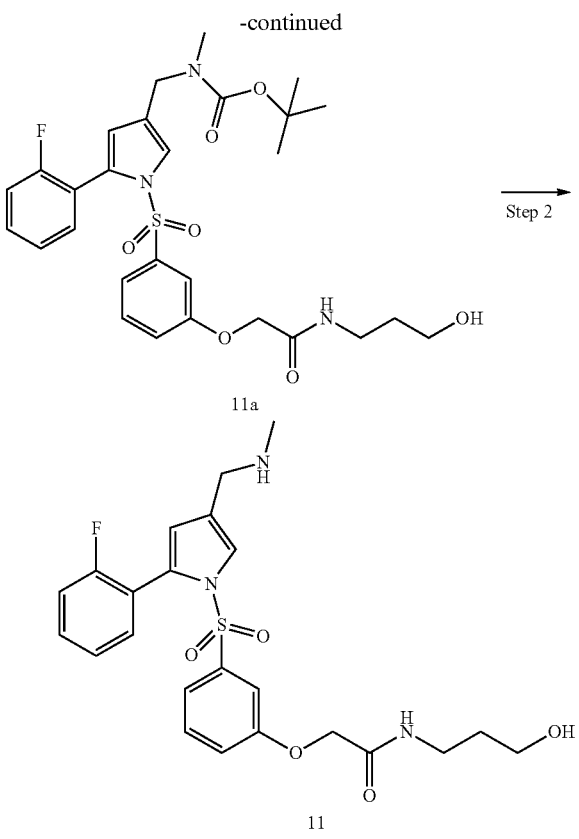

Step 1 tert-Butyl ((5-(2-Fluorophenyl)-1-((3-(2-((3-hydroxypropyl)amino)-2-oxoethoxy)phenyl)sulfonyl)-1H-pyrrol-3-yl)methyl)(methyl)carbamate

Ethyl 2-(3-(((4-(((tert-butoxycarbonyl)(methyl)amino)methyl)-2-(2-fluorophenyl)-1H-pyrrol-1-yl)sulfonyl)phenoxy)acetate 9a (100 mg, 0.18 mmol) was dissolved in 10 mL of isopropanol, followed by addition of two drops of propanolamine, then the reaction solution was heated up to 50° C. and stirred for 24 h. The reaction solution was concentrated under reduced pressure, and the resulting residue was purified by thin layer chromatography with elution system C to obtain the title product tert-butyl ((5-(2-fluorophenyl)-1-((3-(2-((3-hydroxypropyl)amino)-2-oxoethoxy)phenyl)sulfonyl)-1H-pyrrol-3-yl)methyl)(methyl)carbamate 11a (99 mg, a light yellow solid) in 96% yield.

MS m/z (ESI): 476.4 [M−99]

Step 2

2-(3-((2-(2-Fluorophenyl)-4-((methylamino)methyl)-1H-pyrrol-1-yl)sulfonyl)phenoxy)-N-(3-hydroxyphenyl)acetamide tert-Butyl ((5-(2-fluorophenyl)-1-((3-(2-((3-hydroxypropyl)amino)-2-oxoethoxy)phenyl)sulfonyl)-1H-pyrrol-3-yl)methyl)(methyl)carbamate 11a (99 mg, 0.17 mmol) was dissolved in 5 mL of dichloromethane, and the reaction solution was cooled in an ice bath, followed by dropwise addition of a solution of hydrogen chloride in 1,4-dioxane (4 N, 2 mL), and then the reaction solution was stirred for 3 h. The pH of the reaction solution was adjusted to 7 to 8 with the saturated sodium bicarbonate solution, and it was extracted with dichloromethane (50 mL×2). The organic phases were combined, dried over anhydrous sodium sulfate, filtered, and the filtrate was concentrated under reduced pressure. The resulting residue was purified by thin layer chromatography with elution system A to obtain the title product 2-(3-((2-(2-fluorophenyl)-4-((methylamino)methyl)-1H-pyrrol-1-yl)sulfonyl)phenoxy)-N-(3-hydroxypropyl)acetamide 11 (80 mg, a light yellow oil) in 97% yield.

MS m/z (ESI): 476.1 [M+1]

$^1$H NMR (400 MHz, DMSO-$d_6$) δ 1.58 (br, 2H), 1.99 (br, 1H), 2.42 (br, 3H), 3.18 (br, 3H), 3.41 (br, 3H), 3.85 (br, 2H), 4.04 (br, 1H), 4.49 (br, 2H), 6.34 (m, 1H), 6.99 (br, 1H), 7.08 (s, 1H), 7.05 (s, 1H), 7.22 (d, J=8.03 Hz, 2H), 7.30 (br, 1H), 7.50 (br, 2H), 7.66 (br, 1H), 8.22 (br, 1H)

Test Example 1

$H^+/K^+$-ATPase Biological Evaluation

The following in-vitro screening test was used for determining the inhibition effect of the compounds of the present invention on enzyme activity of $H^+/K^+$-ATPase.

Experimental Materials and Instruments:

1. microsomes of porcine gastric mucosa (rich in $H^+/K^+$-ATPase) (self-manufactured)
2. ATP (sigma-aldrich, A1852-1VL)
3. Malachite green (Sigma-Aldrich, 213020-25G)
4. Ammonium molybdate (Sigma-Aldrich, 277908-5G).

The experimental steps are briefly described as follows:

I. Preparation of Reagents

1. The compounds were prepared into appropriate concentrations of 10000, 1000, 100, 10, 1 and 0.1 nM with 100% DMSO;
2. Buffer solution 1: 50 mmol/L of HEPES-Tris, 5 mmol/L of magnesium chloride, pH of 6.5;
3. Buffer solution 2: 50 mmol/L of HEPES-Tris, 5 mmol/L of magnesium chloride, pH of 6.5, 10 mmol/L of potassium chloride, pH=6.5;
4. ATP: ATP was diluted with the buffer solution 1 to 2 mM;
5. Malachite green solution: 0.12% of malachite green was dissolved in 2.5 moles of a mixture of sulfuric acid, 7.5% ammonium molybdate and 11% Tween 20, the three components were mixed according to a ratio of 100:25:2 during the use.
6. Microsomes of porcine gastric mucosal (rich in $H^+/K^+$-ATPase) obtained by sucrose gradient centrifugation: a porcine stomach was washed with running water, and immersed into 3 mol/L of concentrated brine for 1-2 min, and then wiped dry; the gastric mucosas were separated, minced, then suspended in a solution of 0.25 mol/L of sucrose, 1 mmol/L of EDTA, and 10 mmol/L of Tris-HCl; homogenization treatment was performed (the ratio was 100 g:330 mL, and 300 mL was further added after the completion of full homogenization), and the resulting homogenate was centrifugalized at 20000G for 30 min to remove the precipitate; the supernatant fluid was taken and centrifugalized at 100000G for 90 min; the precipitate was taken and suspended in 0.25 mol/L of sucrose solution, 0.25 mol/L of sucrose, 7.5% of ficoll were added at the bottom and centrifugalized at 100000G for 5 h. The substances between two liquid surface layers were collected, and then washed with 0.25 mol/L of sucrose solution while being shaken, and the resulting microsomal enzymes were kept at −80° C. for preservation and later use.

II. Experimental Process

10 µL of microsomes of gastric mucosa ($H^+/K^+$-ATPase) were added to 79 µL of the buffer solution 2, followed by addition of 1 µL of the compound solutions with various concentrations, and then 10 µL of 2 mM ATP were added to start the reaction. It was reacted at 37° C. for 30 min. 30 µL of malachite green solution was added to terminate the reaction, and the reaction solution was kept at room temperature for 20 min, and then an OD value was read at 620 nm on a Victor3 microplate reader, and the inhibition rates of the compounds at various concentrations against $H^+/K^+$-ATPase were calculated.

Simultaneously, the reaction without addition of potassium chloride was taken as a background, which was subtracted when enzyme activity was calculated.

$IC_{50}$ values can be calculated from the inhibition rates of the test compounds at various concentrations.

III. Experimental Results $IC_{50}$ Values of Compounds

| Compound No. | $IC_{50}(H^+/K^+$-ATPase)/(nM) |
|---|---|
| Example 1 | 21 |
| Example 4 | 63 |
| Example 5 | 81 |
| Example 6 | 106 |
| Example 7 | 95 |
| Example 10 | 49 |
| Example 11 | 61 |

Conclusion: the compounds of the present invention have obvious inhibition activity against $H^+/K^+$-ATPase Test Example 2

Test of Inhibition Effect of Compounds of the Present Invention on Gastric Acid Secretion of Rats with Pyloric Ligation Induced Ulcer A rat gastric ulcer model, in which rat gastric acid secretion was promoted by pyloric ligation and histamine hydrochloride, was established in the following experiment, for evaluating the effect of the test compounds on inhibition of gastric acid secretion.

2.1 Experimental Animals and Feeding Conditions:

Sixteen 7-week-old Sprague-Dawley (SD) male rats with a weight of about 250 g were purchased form Sippr-BK (batch number: 2008001621913). The rats were fed by 4 rats/cage, 12/12 h light/dark cyclic regulation was performed, the temperature was constant at 23±1° C., the humidity was 50-60%, and the rats took food and water freely.

2.2 Experimental Drugs and Reagents:

The compound of Example 1, which was prepared into a solution/suspension with 0.5% of sodium carboxymethylcellulose (CMC-Na).

Histamine dihydrochloride (with the specification of 5 g, the batch number of F20100823 and the purity of >99%), urethane (with the specification of 500 g, the batch number of F20110214 and the purity of >98.0%) and a NaOH titration standard solution (with the specification of 0.1025 mol/L and 500 ml, the batch number of 20120208 and the quality guarantee period of 20120407) were all purchased from Sinopharm Chemical Reagent Co., Ltd.

2.3 Experimental Method:

The rats were fasted for about 4 h. 2 mg/kg of the compound of Example 1 or 0.5% of CMC-Na were administrated intragastrically (i. g.) to the rats, and then 1.2 g/kg of urethane was injected intraperitoneally within 1 h. After the rats were anesthetized, the part of the pylorus connected to the duodenum was ligated, muscles and skin were further sewn, histamine dihydrochloride (30 mg/kg/10 ml) was injected, while physiological saline was injected in a non-model group, and then the rats were sacrificed after 3 h of injection. The stomachs were taken to collect stomach contents. After centrifugalizing at 4000 rpm for 5 min, the supernatant fluid was sucked up, and the volume of each sample was measured accurately. After diluting a certain amount of gastric acid sample to the detection volume, the potentiometric titration was performed by using a NaOH standard solution on an automatic titration instrument to determine the acid content, and then the total acid value was calculated after 3 h of histamine stimulation according to the total volume of the sample, the gastric acid value of the non-model group was subtracted from the model group, and the effects of all the compounds at different concentrations on inhibition of gastric acid secretion were compared.

2.4 Experimental Instruments

Automatic titrator: which was provided by Shanghai INESA Scientific Instrument Co., Ltd., the type was ZDJ-5 and the number was 640411120019.

Refrigerated centrifuge: Beckman Coulter, 25R.

2.5 Data Expression and Statistical Treatment

Gastric acid titration: the mean value (mean±S.D.) was calculated in each group by Excel software, t test was performed on the total acid value of gastric acid from treatment groups and model group subjects/animals at each time point after drug administration to judge whether a significant difference existed or not.

The total acid value of gastric juice within 3 h after injection of histamine hydrochloride was as follows:

Acid output (mmol/3 h)=total volume of gastric acid/volume of gastric acid used for titration×volume of consumed NaOH standard solution×concentration of NaOH standard solution (0.1025 mol/L)×1000

Gastric acid secretion inhibition rate $$(I\%) = \left[1 - \frac{\text{Acid output (drug group-non-model group)}}{\text{Acid output (model group-non-model group)}}\right] \times 100\%$$

2.6. Results and Discussions

After 1 h of administration, the compound of Example 1 significantly inhibited gastric acid secretion of the rats with pyloric ligation induced gastric ulcer within 3 h, namely when the administration dosage was 2 mg/kg, the acid inhibition rate at 1 h was 89.3%, so that the acid inhibition effect for 1 h of the compound of Example 1 was significant.

Test Example 3

Test of Inhibition Effect of Compounds of the Present Invention on Gastric Acid Secretion of Rats with Pyloric Ligation Induced Ulcer A rat gastric ulcer model, in which rat gastric acid secretion was promoted by pyloric ligation and histamine hydrochloride, was established in the following experiment, for evaluating the effect of the test compounds on inhibition of the gastric acid secretion.

3.1 Experimental Animals and Feeding Conditions:

Twenty-four (24) 7-week-old SD male rats with a weight of about 250 g were purchased form Sippr-BK (batch number: 2008001621913). The rats were fed by 4 rats/cage, 12/12 h light/dark cyclic regulation was performed, the temperature was constant at 23±1° C., the humidity was 50-60%, and the rats took food and water freely.

3.2 Experimental Drugs and Reagents:

The compound of Example 1 was prepared into a solution/suspension with 0.5% of CMC-Na.

Histamine dihydrochloride (with the specification of 5 g, the batch number of F20100823 and a purity of >99%), urethane (with the specification of 500 g, the batch number of F20110214 and a purity of >98.0%) and a NaOH titration standard solution (with the specification of 0.1025 mol/L and 500 ml, the batch number of 20120208 and the quality guarantee period of 20120407) were all purchased from Sinopharm Chemical Reagent Co., Ltd.

3.3 Experimental Method:

The rats were fasted for about 24 h. 4 mg/kg and 8 mg/kg of the compound of Example 1 or 0.5% of CMC-Na were administrated intragastrically (i. g) to the rats, and then 1.2 g/kg of urethane was injected intraperitoneally within 24 h. After the rats were anesthetized, the part of the pylorus connected to the duodenum was ligated, muscles and skin were further sewn, histamine dihydrochloride (30 mg/kg/10 ml) was injected, while physiological saline was injected in a non-model group, and then the rats were sacrificed after 3 h of injection. The stomachs were taken to collect stomach contents. After centrifugalizing at 4000 rpm for 10 min, the supernatant fluid was sucked up, and the volume of each sample was measured accurately. After diluting a certain amount of gastric acid sample to the detection volume, the potentiometric titration was performed by using a NaOH standard solution on an automatic titration instrument to determine the acid content, and then the total acid value was calculated after 3 h of histamine stimulation according to the total volume of the sample, the gastric acid value of the non-model group was subtracted from the model group, and the effects of all the compounds at different concentrations on inhibition of gastric acid secretion were compared.

3.4 Experimental Instruments

Automatic titrator: which was provided by Shanghai INESA Scientific Instrument Co., Ltd., the type was ZDJ-5 and the number was 640411120019.

Refrigerated centrifuge: Beckman Coulter, 25R.

3.5 Data Expression and Statistical Treatment

Gastric acid titration: the mean value (mean±S.D.) was calculated in each group by Excel software, t test was performed on the total acid value of gastric acid from treatment groups and model group subjects/animals at each time point after drug administration to judge whether a significant difference existed or not.

The total acid value of gastric juice within 3 h after injection of histamine hydrochloride was as follows:

Acid output (mmol/3 h)=total volume of gastric acid/volume of gastric acid used for titration×volume of consumed NaOH standard solution×concentration of NaOH standard solution (0.1025 mol/L)×1000

Gastric acid secretion inhibition rate $$(I\%) = \left[1 - \frac{\text{Acid output (drug group-non-model group)}}{\text{Acid output (model group-non-model group)}}\right] \times 100\%$$

3.6. Results and Discussions

After 24 h of administration, the compound of Example 1 significantly inhibited the gastric acid secretion of the rats with pyloric ligation induced gastric ulcer within 3 h, namely when the administration dosages were 4 mg/kg and 8 mg/kg, the acid inhibition rates at 24 h were 89.6% and 99.4% respectively, so that the 24 h long-acting acid inhibition effect of the compound of Example 1 was significant.

What is claimed is:

1. A compound of formula (I), or a tautomer, mesomer, racemate, enantiomer, diastereoisomer or mixture thereof, or a pharmaceutically acceptable salt thereof:

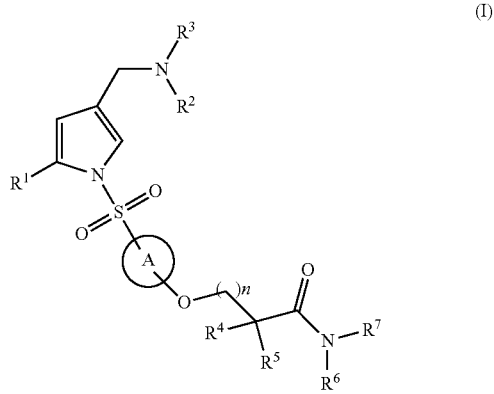

(I)

wherein:

$R^1$ is selected from the group consisting of phenyl and cyclohexenyl, wherein the phenyl and cyclohexenyl are each optionally substituted by one or more groups selected from the group consisting of halogen, cyano, $C_1$-$C_{20}$ alkyl, $C_1$-$C_{20}$ haloalkyl, $C_1$-$C_{20}$ hydroxyalkyl, $C_3$-$C_{20}$ cycloalkyl, $C_1$-$C_{20}$ alkoxy, heterocyclyl containing 3 to 20 ring atoms, 6 to 14-membered aryl, 5 to 14-membered heteroaryl, carboxyl and alkoxycarbonyl;

$R^2$ is selected from the group consisting of hydrogen atom, $C_1$-$C_{20}$ alkyl, $C_3$-$C_{20}$ cycloalkyl, heterocyclyl containing 3 to 20 ring atoms, 6 to 14-membered aryl and 5 to 14-membered heteroaryl, wherein the alkyl, cycloalkyl, heterocyclyl, aryl and heteroaryl are each optionally substituted by one or more groups selected from the group consisting of halogen, cyano, hydroxy, amino, $C_1$-$C_{20}$ alkyl, $C_1$-$C_{20}$ haloalkyl, $C_1$-$C_{20}$ hydroxyalkyl, $C_1$-$C_{20}$ alkoxy, $C_3$-$C_{20}$ cycloalkyl, heterocyclyl containing 3 to 20 ring atoms, 6 to 14-membered aryl, 5 to 14-membered heteroaryl, carboxyl and alkoxycarbonyl;

$R^3$ is selected from the group consisting of hydrogen atom and $C_1$-$C_{20}$ alkyl;

ring A is phenyl optionally substituted by one or more groups selected from the group consisting of halogen, cyano, $C_1$-$C_{20}$ alkyl, $C_1$-$C_{20}$ haloalkyl, $C_1$-$C_{20}$ hydroxyalkyl, $C_3$-$C_{20}$ cycloalkyl, $C_1$-$C_{20}$ alkoxy, heterocyclyl containing 3 to 20 ring atoms, 6 to 14-membered aryl, 5 to 14-membered heteroaryl, carboxyl and alkoxycarbonyl;

$R^4$ and $R^5$ are each independently selected from the group consisting of hydrogen atom, halogen, cyano, hydroxy, $C_1$-$C_{20}$ alkyl, $C_1$-$C_{20}$ haloalkyl, $C_1$-$C_{20}$ alkoxy, $C_1$-$C_{20}$ haloalkoxy, $C_3$-$C_{20}$ cycloalkyl, heterocyclyl containing 3 to 20 ring atoms, 6 to 14-membered aryl and 5 to 14-membered heteroaryl;

or R⁴ and R⁵ are taken together to form a $C_3$-$C_{20}$ cycloalkyl or heterocyclyl containing 3 to 20 ring atoms;

R⁶ and R⁷ are each independently selected from the group consisting of hydrogen atom, $C_1$-$C_{20}$ alkyl, $C_3$-$C_{20}$ cycloalkyl, heterocyclyl containing 3 to 20 ring atoms, 6 to 14-membered aryl and 5 to 14-membered heteroaryl, wherein the alkyl, cycloalkyl, heterocyclyl, aryl and heteroaryl are each independently and optionally substituted by one or more groups selected from the group consisting of halogen, cyano, hydroxy, amino, oxo, $C_1$-$C_{20}$ alkyl, $C_1$-$C_{20}$ haloalkyl, $C_1$-$C_{20}$ hydroxyalkyl, $C_1$-$C_{20}$ alkoxy, $C_3$-$C_{20}$ cycloalkyl, heterocyclyl containing 3 to 20 ring atoms, 6 to 14-membered aryl, 5 to 14-membered heteroaryl, carboxyl and alkoxycarbonyl; and n is 0, 1 or 2.

2. The compound of formula (I), or a tautomer, mesomer, racemate, enantiomer, diastereomer, or mixture thereof, or a pharmaceutically acceptable salt thereof according to claim 1, being a compound of formula (II), or a tautomer, mesomer, racemate, enantiomer, diastereomer, or mixture thereof, or a pharmaceutically acceptable salt thereof:

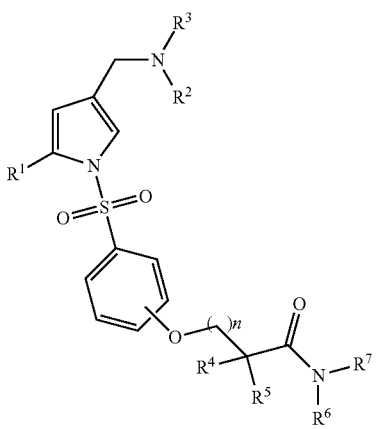

(II)

wherein:
R¹ is selected from the group consisting of phenyl and cyclohexenyl wherein the phenyl and cyclohexenyl are each optionally substituted by one or more groups selected from the group consisting of halogen, cyano, $C_1$-$C_{20}$ alkyl, $C_1$-$C_{20}$ haloalkyl, $C_1$-$C_{20}$ hydroxyalkyl, $C_3$-$C_{20}$ cycloalkyl, $C_1$-$C_{20}$ alkoxy, heterocyclyl containing 3 to 20 ring atoms, 6 to 14-membered aryl, 5 to 14-membered heteroaryl, carboxyl and alkoxycarbonyl;

R² is selected from the group consisting of $C_1$-$C_{20}$ alkyl;

R³ is selected from the group consisting of hydrogen atom and $C_1$-$C_{20}$ alkyl;

R⁴ and R⁵ are each independently selected from the group consisting of hydrogen atom, halogen, cyano, hydroxy, $C_1$-$C_{20}$ alkyl, $C_1$-$C_{20}$ haloalkyl, $C_1$-$C_{20}$ alkoxy, $C_1$-$C_{20}$ haloalkoxy, $C_3$-$C_{20}$ cycloalkyl, heterocyclyl containing 3 to 20 ring atoms, 6 to 14-membered aryl and 5 to 14-membered heteroaryl;

or R⁴ and R⁵ are taken together to form a $C_3$-$C_{20}$ cycloalkyl or heterocyclyl containing 3 to 20 ring atoms;

R⁶ and R⁷ are each independently selected from the group consisting of hydrogen atom, $C_1$-$C_{20}$ alkyl, $C_3$-$C_{20}$ cycloalkyl, heterocyclyl containing 3 to 20 ring atoms, 6 to 14-membered aryl and 5 to 14-membered heteroaryl, wherein the alkyl, cycloalkyl, heterocyclyl, aryl and heteroaryl are each independently and optionally substituted by one or more groups selected from the group consisting of halogen, cyano, hydroxy, amino, oxo, $C_1$-$C_{20}$ alkyl, $C_1$-$C_{20}$ haloalkyl, $C_1$-$C_{20}$ hydroxyalkyl, $C_1$-$C_{20}$ alkoxy, $C_3$-$C_{20}$ cycloalkyl, heterocyclyl containing 3 to 20 ring atoms, 6 to 14-membered aryl, 5 to 14-membered heteroaryl, carboxyl and alkoxycarbonyl; and n is 0, 1 or 2.

3. The compound of formula (I), or a tautomer, mesomer, racemate, enantiomer, diastereomer, or mixture thereof, or a pharmaceutically acceptable salt thereof according to claim 1, wherein R¹ is phenyl, and the phenyl is optionally substituted by one or more halogens.

4. The compound of formula (I), or a tautomer, mesomer, racemate, enantiomer, diastereomer, or mixture thereof, or a pharmaceutically acceptable salt thereof according to claim 1, wherein R⁴ is a hydrogen atom.

5. The compound of formula (I), or a tautomer, mesomer, racemate, enantiomer, diastereomer, or mixture thereof, or a pharmaceutically acceptable salt thereof according to claim 1, wherein R⁵ is a hydrogen atom.

6. The compound of formula (I), or a tautomer, mesomer, racemate, enantiomer, diastereomer, or mixture thereof, or a pharmaceutically acceptable salt thereof according to claim 1, wherein R⁴ and R⁵ are taken together to form a $C_3$-$C_{20}$ cycloalkyl.

7. The compound of formula (I), or a tautomer, mesomer, racemate, enantiomer, diastereomer, or mixture thereof, or a pharmaceutically acceptable salt thereof according to claim 1, wherein R⁶ and R⁷ are each independently selected from the group consisting of hydrogen atom, $C_1$-$C_{20}$ alkyl and $C_3$-$C_{20}$ cycloalkyl, wherein the alkyl and cycloalkyl are each independently and optionally substituted by one or more groups selected from the group consisting of halogen, hydroxy, amino, $C_1$-$C_{20}$ alkoxy, $C_3$-$C_{20}$ cycloalkyl, heterocyclyl containing 3 to 20 ring atoms, 6 to 14-membered aryl, 5 to 14-membered heteroaryl, carboxyl and alkoxycarbonyl.

8. The compound of formula (I), or a tautomer, mesomer, racemate, enantiomer, diastereomer, or mixture thereof, or a pharmaceutically acceptable salt thereof according to claim 1, wherein the compound is selected from the group consisting of:

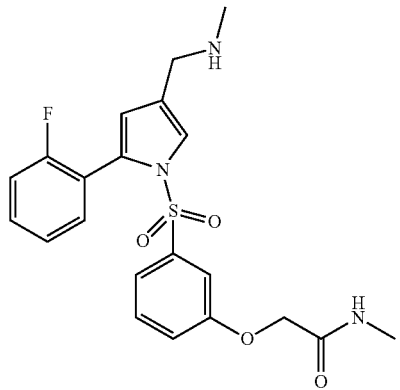

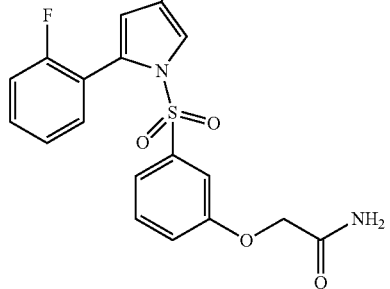
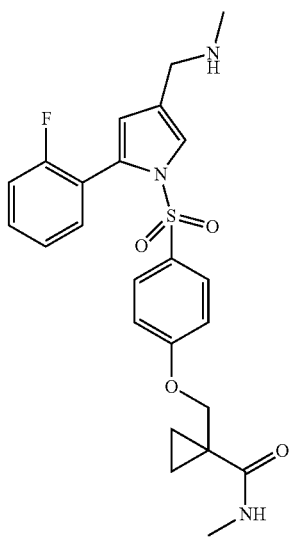
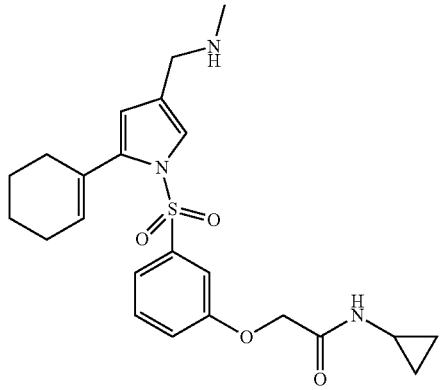
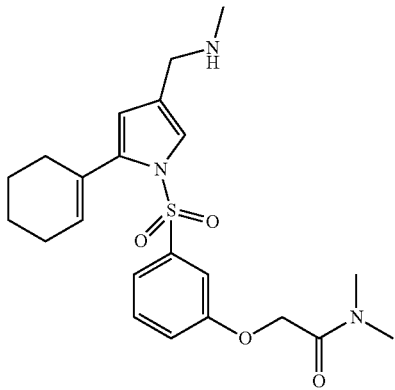
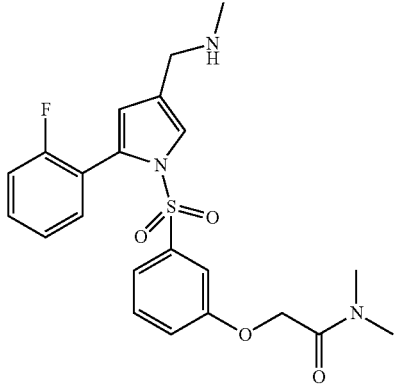

-continued

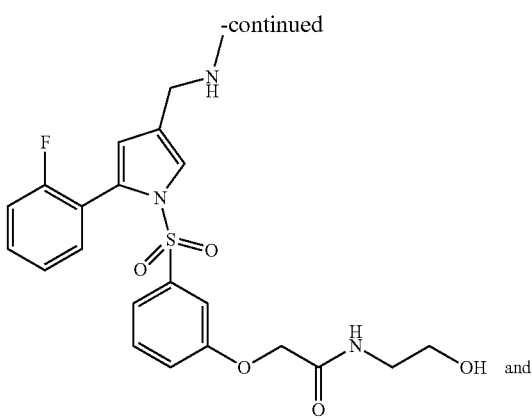

and

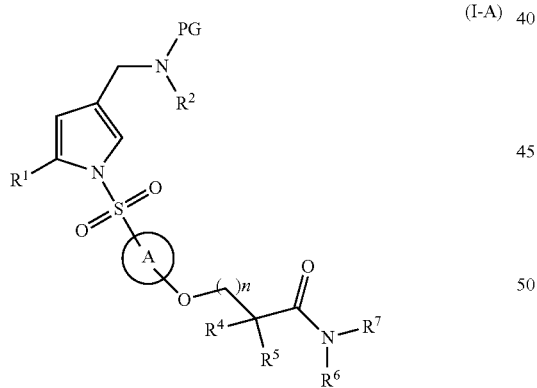

9. A compound of formula (I-A), or a tautomer, mesomer, racemate, enantiomer, diastereomer, or mixture thereof, or a pharmaceutically acceptable salt thereof:

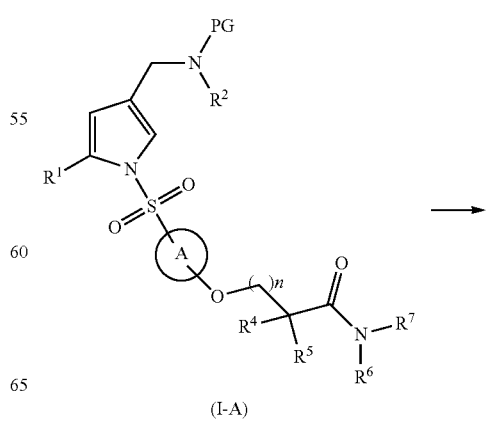

(I-A)

wherein:
  $R^1$ is selected from the group consisting of phenyl and cyclohexenyl, wherein the phenyl and cyclohexenyl is optionally substituted by one or more groups selected from the group consisting of halogen, cyano, $C_1$-$C_{20}$ alkyl, $C_1$-$C_{20}$ haloalkyl, $C_1$-$C_{20}$ hydroxyalkyl, $C_3$-$C_{20}$ cycloalkyl, $C_1$-$C_{20}$ alkoxy, heterocyclyl containing 3 to 20 ring atoms, 6 to 14-membered aryl, 5 to 14-membered heteroaryl, carboxyl and alkoxycarbonyl;
  $R^2$ is selected from the group consisting of hydrogen atom, $C_1$-$C_{20}$ alkyl, $C_3$-$C_{20}$ cycloalkyl, heterocyclyl containing 3 to 20 ring atoms, 6 to 14-membered aryl and 5 to 14-membered heteroaryl, wherein the alkyl, cycloalkyl, heterocyclyl, aryl and heteroaryl are each optionally substituted by one or more groups selected from the group consisting of halogen, cyano, hydroxy, amino, $C_1$-$C_{20}$ alkyl, $C_1$-$C_{20}$ haloalkyl, $C_1$-$C_{20}$ hydroxyalkyl, $C_1$-$C_{20}$ alkoxy, $C_3$-$C_{20}$ cycloalkyl, heterocyclyl containing 3 to 20 ring atoms, 6 to 14-membered aryl, 5 to 14-membered heteroaryl, carboxyl and alkoxycarbonyl;

ring A is phenyl optionally substituted by one or more groups selected from the group consisting of halogen, cyano, $C_1$-$C_{20}$ alkyl, $C_1$-$C_{20}$ haloalkyl, $C_1$-$C_{20}$ hydroxyalkyl, $C_3$-$C_{20}$ cycloalkyl, $C_1$-$C_{20}$ alkoxy, heterocyclyl containing 3 to 20 ring atoms, 6 to 14-membered aryl, 5 to 14-membered heteroaryl, carboxyl and alkoxycarbonyl;

$R^4$ and $R^5$ are each independently selected from the group consisting of hydrogen atom, halogen, cyano, hydroxy, $C_1$-$C_{20}$ alkyl, $C_1$-$C_{20}$ haloalkyl, $C_1$-$C_{20}$ alkoxy, $C_1$-$C_{20}$ haloalkoxy, $C_3$-$C_{20}$ cycloalkyl, heterocyclyl containing 3 to 20 ring atoms, 6 to 14-membered aryl and 5 to 14-membered heteroaryl;

or $R^4$ and $R^5$ are taken together to form a $C_3$-$C_{20}$ cycloalkyl or heterocyclyl containing 3 to 20 ring atoms;

$R^6$ and $R^7$ are each independently selected from the group consisting of hydrogen atom, $C_1$-$C_{20}$ alkyl, $C_3$-$C_{20}$ cycloalkyl, heterocyclyl containing 3 to 20 ring atoms, 6 to 14-membered aryl and 5 to 14-membered heteroaryl, wherein the alkyl, cycloalkyl, heterocyclyl, aryl and heteroaryl are each independently and optionally substituted by one or more groups selected from the group consisting of halogen, cyano, hydroxy, amino, oxo, $C_1$-$C_{20}$ alkyl, $C_1$-$C_{20}$ haloalkyl, $C_1$-$C_{20}$ hydroxyalkyl, $C_1$-$C_{20}$ alkoxy, $C_3$-$C_{20}$ cycloalkyl, heterocyclyl containing 3 to 20 ring atoms, 6 to 14-membered aryl, 5 to 14-membered heteroaryl, carboxyl and alkoxycarbonyl;

n is 0, 1 or 2; and

PG is an amino-protecting group.

10. A process for preparing the compound of formula (I), or a tautomer, mesomer, racemate, enantiomer, diastereomer, or mixture thereof, or a pharmaceutically acceptable salt thereof according to claim 1, comprising a step of:

(I-A)

-continued

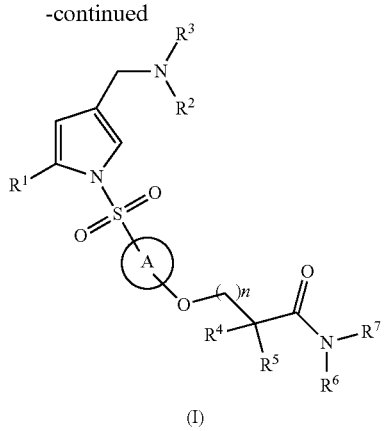

(I)

deprotecting a compound of formula (I-A) in a solvent under an acidic condition to obtain a compound of formula (I);

wherein PG is an amino-protecting group.

11. A pharmaceutical composition comprising a therapeutically effective amount of the compound of formula (I), or a tautomer, mesomer, racemate, enantiomer, diastereomer, or mixture thereof, or a pharmaceutically acceptable salt thereof according to claim 1, and a pharmaceutically acceptable carrier, a diluent or an excipient.

12. The compound of formula (I), or a tautomer, mesomer, racemate, enantiomer, diastereomer, or mixture thereof, or a pharmaceutically acceptable salt thereof according to claim 6, wherein $R^4$ and $R^5$ are taken together to form cyclopropyl.

13. The compound of formula (I-A), or a tautomer, mesomer, racemate, enantiomer, diastereomer, or mixture thereof, or a pharmaceutically acceptable salt thereof according to claim 9, wherein $R^2$ is a $C_1$-$C_{20}$ alkyl.

14. The compound of formula (I-A), or a tautomer, mesomer, racemate, enantiomer, diastereomer, or mixture thereof, or a pharmaceutically acceptable salt thereof according to claim 9, wherein PG is tert-butoxycarbonyl.

15. The process according to claim 10, wherein $R^3$ is hydrogen.

16. The process according to claim 10, wherein PG is tert-butoxycarbonyl.

17. A method of inhibiting gastric acid secretion in a subject in need thereof, the method comprising administering to the subject the pharmaceutical composition according to claim 11.

18. A method of inhibiting $H^+/K^+$-adenosine triphosphatase ($H^+/K^+$-ATPase) in a subject in need thereof, the method comprising administering to the subject the pharmaceutical composition according to claim 11.

19. A method of competitively inhibiting gastric acid secretion by blocking accession of potassium ion to its binding site on a gastric $H^+/K^+$-adenosine triphosphatase in a subject in need thereof, the method comprising administering to the subject the pharmaceutical composition according to claim 11.

20. A method of treating peptic ulcer, Zollinger-Ellison syndrome, gastritis, erosive esophagitis, reflux esophagitis, symptomatic gastroesophageal reflux disease, Barrett's esophagitis, functional dyspepsia, *helicobacter pylori* infection, gastric cancer, gastric MALT lymphoma, ulcer caused by a nonsteroidal anti-inflammatory drug or hyperacidity or ulcer caused by postoperative stress; or a method of inhibiting upper gastrointestinal bleeding caused by peptic ulcer, acute stress ulcer, hemorrhagic gastritis or invasive stress in a subject in need thereof, the method comprising administering to the subject the pharmaceutical composition according to claim 11.

21. The method according to claim 20, wherein the peptic ulcer is gastric ulcer, duodenal ulcer or stomal ulcer; and the symptomatic gastroesophageal reflux disease is non-erosive reflux disease or gastroesophageal reflux disease without oesophagitis.

* * * * *